(12) United States Patent
Brys et al.

(10) Patent No.: US 10,508,111 B2
(45) Date of Patent: Dec. 17, 2019

(54) 6-[5-AMINO-6-(2-ETHOXYETHOXY)-IMIDAZO[4,5-B]PYRIDIN-3-YL]-NICOTINONITRILE DERIVATIVES AND THEIR USE AS IRAK INHIBITORS

(71) Applicant: GALAPAGOS NV, Mechelen (BE)

(72) Inventors: Reginald Christophe Xavier Brys, Mechelen (BE); Raphaël Jean Joël Geney, Romainville (FR); Agnès Marie Joncour, Romainville (FR); Julien Georges Pierre-Olivier Doyon, Beerse (BE); Frédéric Gilbert Labéguère, Frouzins (FR); Jean-Michel Lefrançois, Romainville (FR); Oscar Mammoliti, Mechelen (BE); Benoît Antoine Schmitt, Mechelen (BE); Steven Emiel Van Der Plas, Mechelen (BE); Christel Jeanne Marie Menet, Brussels (BE)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 15/769,260

(22) PCT Filed: Oct. 14, 2016

(86) PCT No.: PCT/EP2016/074662
§ 371 (c)(1),
(2) Date: Apr. 18, 2018

(87) PCT Pub. No.: WO2017/067848
PCT Pub. Date: Apr. 27, 2017

(65) Prior Publication Data
US 2018/0305351 A1    Oct. 25, 2018

(30) Foreign Application Priority Data
Oct. 19, 2015   (GB) .................................. 1518456.7

(51) Int. Cl.
*A61K 45/06*    (2006.01)
*C07D 471/04*   (2006.01)
*A61P 37/00*    (2006.01)
*A61P 29/00*    (2006.01)

(52) U.S. Cl.
CPC ............ *C07D 471/04* (2013.01); *A61P 29/00* (2018.01); *A61P 37/00* (2018.01); *A61K 45/06* (2013.01); *A61K 2300/00* (2013.01)

(58) Field of Classification Search
CPC ........ C07D 471/04; A61P 37/00; A61P 29/00; A61K 45/06
USPC ...................................................... 514/303
See application file for complete search history.

(56) References Cited

FOREIGN PATENT DOCUMENTS

WO    WO 2015/103453 A1    7/2015

OTHER PUBLICATIONS

IRAK-4 deficiency, Genetics Home Reference , Ku Ci et al (Year: 2018).*
Curis anounces initiation trials for phase one Clinical trial of CA-4948 . . . (Year: 2017).*
Bain J. et al., "The specificities of protein kinase inhibitors: an update.," Biochemical Journal, 2003; vol. 371, No. 1, pp. 199-204.
Brehm M. A. et al., "Rapid Production of TNF-α following TCR Engagement of Naive CD8 T Cells," The Journal of Immunology, 2005; vol. 175, No. 8, pp. 5043-5049.
Broekman F. et al., "Tyrosine kinase inhibitors: Multi-targeted or single-targeted?," World Journal of Clinical Oncology, 2011; vol. 2, No. 2, pp. 80-93.
Carmi Y. et al., "The Role of IL-1β in the Early Tumor Cell—Induced Angiogenic Response," The Journal of Immunology, 2013; vol. 190, No. 7, pp. 3500-3509.
Chiang E. Y. et al., "Immune Complex-Mediated Cell Activation from Systemic Lupus Erythematosus and Rheumatoid Arthritis Patients Elaborate Different Requirements for IRAK1/4 Kinase Activity across Human Cell Types," The Journal of Immunology, 2011; vol. 186, No. 2, pp. 1279-1288.
Cohen P., "Targeting protein kinases for the development of anti-inflammatory drugs," Current Opinion in Cell Biology, 2009; vol. 21, No. 2, pp. 317-324.

(Continued)

*Primary Examiner* — Rita J Desai
(74) *Attorney, Agent, or Firm* — Arent Fox LLP

(57) ABSTRACT

The present invention discloses compounds according to Formula I:

wherein $R^1$, $R^2$, and Cy are as defined herein.
The present invention relates to compounds inhibiting IRAK family kinases, methods for their production, pharmaceutical compositions comprising the same, and methods of treatment using the same, for the prophylaxis and/or treatment of inflammatory diseases, autoimmune diseases and/or proliferative diseases by administering the compound of the invention.

15 Claims, No Drawings
Specification includes a Sequence Listing.

(56) References Cited

OTHER PUBLICATIONS

Dinarello C. A. et al., "Treating inflammation by blocking interleukin-1 in a broad spectrum of diseases," Nature reviews Drug discovery, 2012; vol. 11, No. 8, pp. 633-652.
Dy G. K. et al., "Understanding, recognizing, and managing toxicities of targeted anticancer therapies," CA: A Cancer Journal for Clinicians, 2013; vol. 63, No. 4, pp. 249-279.
Emea, Public statement on the increased risk of serious infection and neutropenia in patients treated concurrently with Kineret (anakinra) and Enbrel (etanercept), Feb. 5, 2003, 4 pages.
Fabian M. A.et al., "A small molecule-kinase interaction map for clinical kinase inhibitors," Nature Biotechnology, 2005; vol. 23, No. 3, pp. 329-336.
Force T. et al., "Cardiotoxicity of kinase inhibitors: the prediction and translation of preclinical models to clinical outcomes," Nature Reviews Drug Discovery, 2011; vol. 10, No. 2, pp. 111-126.
Genovese M. C. et al., "Combination therapy with etanercept and anakinra in the treatment of patients with rheumatoid arthritis who have been treated unsuccessfully with methotrexate," Arthritis & Rheumatism, 2004; vol. 50, No. 5, pp. 1412-1419.
International Search Report of the International Searching Authority for PCT/EP2016/074662 dated Jan. 25, 2017.
Koziczak-Holbro M. et al., "The critical role of kinase activity of interleukin-1 receptor—associated kinase 4 in animal models of joint inflammation," Arthritis & Rheumatism, 2009; vol. 60, No. 6, pp. 1661-1671.
Kroeger K. M. et al., "IL-18 and IL-33 elicit Th2 cytokines from basophils via a MyD88- and p38α-dependent pathway," Journal of Leukocyte Biology, 2009; vol. 86, No. 4, pp. 769-778.
Li D. et al., "IL-33 promotes ST2-dependent lung fibrosis by the induction of alternatively activated macrophages and innate lymphoid cells in mice," Journal of Allergy and Clinical Immunology, 2014; vol. 134, No. 6, pp. 1422-1432.
Li M. et al., "Topical vitamin D3 and low-calcemic analogs induce thymic stromal lymphopoietin in mouse keratinocytes and trigger an atopic dermatitis," Proceedings of the National Academy of Sciences, 2006; vol. 103, No. 31, pp. 11736-11741.
Li S. et al., "IRAK-4: A novel member of the IRAK family with the properties of an IRAK-kinase," Proceedings of the National Academy of Sciences of the United States of America, 2002; vol. 99, No. 8, pp. 5567-5572.
Li Z. et al., "Inhibition of IRAK1/4 sensitizes T cell acute lymphoblastic leukemia to chemotherapies," The Journal of Clinical Investigation, 2015; vol. 125, No. 3, pp. 1081-1097.
McHedlidze T. et al., "Interleukin-33-dependent innate lymphoid cells mediate hepatic fibrosis," Immunity, 2013; vol. 39, No. 2, pp. 357-371.
Nabe T., "Interleukin (IL)-33: New Therapeutic Target for Atopic Diseases," Journal of Pharmacological Sciences, 2014; vol. 126, No. 2, pp. 85-91.
Ngo V. N. et al., "Oncogenically active MYD88 mutations in human lymphoma," Nature, 2011; vol. 470, No. 7332, pp. 115-119.
Rankin A. L. et al., "IL-33 Induces IL-13—Dependent Cutaneous Fibrosis," The Journal of Immunology, 2010; vol. 184, No. 3, pp. 1526-1535.
Rhyasen G. W. et al., "IRAK signalling in cancer," British Journal of Cancer, 2015; vol. 112, No. 2, pp. 232-237.
Ringwood L. et al., "The involvement of the interleukin-1 Receptor-Associated Kinases (IRAKs) in cellular signaling networks controlling inflammation," Cytokine, 2008; vol. 42, No. 1, pp. 1-7.
Rizzo H. L. et al., "IL-23—Mediated Psoriasis-Like Epidermal Hyperplasia is Dependent on IL-17A," The Journal of Immunology, 2011; vol. 186, No. 3, pp. 1495-1502.
Salimi M. et al., "A role for IL-25 and IL-33—driven type-2 innate lymphoid cells in atopic dermatitis," The Journal of Experimental Medicine, 2013; vol. 210, No. 13, pp. 2939-2950.
Sherlock J. P. et al., "IL-23 induces spondyloarthropathy by acting on ROR-γt+ CD3+CD4-CD8-entheseal resident T cells," Nature Medicine, 2012; vol. 18, No. 7, pp. 1069-1076.
Staschke K. A. et al., "IRAK4 Kinase Activity is Required for Th17 Differentiation and Th17-Mediated Disease," The Journal of Immunology, 2009; vol. 183, No. 1, pp. 568-577.
Sundberg T. B. et al., "Small-molecule control of cytokine function: new opportunities for treating immune disorders," Current Opinion in Chemical Biology, 2014; vol. 23, pp. 23-30.
Treon S. P. et al., "MYD88 L265P Somatic Mutation in Waldenstrom's Macroglobulinemia," New England Journal of Medicine, 2012; vol. 367, No. 9, pp. 826-833.
Tumey L. N. et al., "Identification and optimization of indolo[2,3-c]quinoline inhibitors of IRAK4," Bioorganic & Medicinal Chemistry Letters, 2014; vol. 24, No. 9, pp. 2066-2072.
Van Der Fits L. et al., "Imiquimod-induced psoriasis-like skin inflammation in mice is mediated via the IL-23/IL-17 axis," The Journal of Immunology, 2009; vol. 182, No. 9, pp. 5836-5845.
Vidal-Vanaclocha F. et al., "IL-18 regulates IL-1β-dependent hepatic melanoma metastasis via vascular cell adhesion molecule-1," Proceedings of the National Academy of Sciences, 2000; vol. 97, No. 2, pp. 734-739.
Wang Z. et al., "IRAK-4 Inhibitors for Inflammation," Current Topics in Medicinal Chemistry, 2009; vol. 9, No. 8, pp. 724-737.
Yan C. et al., "C5a-regulated CCAAT/Enhancer-binding Proteins β and δ Are Essential in Fcγ Receptor-mediated Inflammatory Cytokine and Chemokine Production in Macrophages," Journal of Biological Chemistry, 2012; vol. 287, No. 5, pp. 3217-3230.
Yokogawa M. et al., "Epicutaneous Application of Toll-like Receptor 7 Agonists Leads to Systemic Autoimmunity in Wild-Type Mice: A New Model of Systemic Lupus Erythematosus," Arthritis & Rheumatology, 2014; vol. 66, No. 3, pp. 694-706.

* cited by examiner

6-[5-AMINO-6-(2-ETHOXYETHOXY)-IMIDAZO[4,5-B]PYRIDIN-3-YL]-NICOTINONITRILE DERIVATIVES AND THEIR USE AS IRAK INHIBITORS

CROSS REFERENCE TO RELATED APPLICATIONS

This application is a 35 U.S.C. 371 National Phase of PCT Application No. PCT/EP2016/074662, filed Oct. 14, 2016, which claims priority to GB Application No. 1518456.7, filed Oct. 19, 2015, the disclosure of each of which is hereby incorporated by reference.

FIELD OF THE INVENTION

The present invention relates to compounds useful in the prophylaxis and/or treatment of inflammatory diseases, autoimmune diseases, and/or proliferative diseases. In particular, the compounds of the invention may inhibit Interleukin-1 Receptor Associated Kinases (IRAKs), a family of kinases that are involved in inflammatory diseases, autoimmune diseases, and/or proliferative diseases, and more particularly IRAK-4. The present invention also provides methods for the production of the compounds of the invention, pharmaceutical compositions comprising the compounds of the invention, methods for the prophylaxis and/or treatment of inflammatory diseases, autoimmune diseases, and/or proliferative diseases by administering the compounds of the invention.

BACKGROUND OF THE INVENTION

Kinases are involved in many essential processes of cell physiology, for example protein phosphorylation. In particular, protein and lipid kinases are involved in the activation, growth, differentiation, and survival of cells. Protein kinases can be divided between those preferentially phosphorylating tyrosine residues, and those preferentially phosphorylating serine and/or threonine residues.

Over the years, kinases have grown to become very important targets for the development of anti-inflammatory drugs (Cohen 2009). In particular, IRAK kinases, and more particularly IRAK-4 have been identified as playing a role in inflammation and autoimmune diseases (Ringwood & Li 2008; Wang et al. 2009).

IRAKs are expressed in many cell types and mediate signals from various cell receptors including interleukin-1 (IL-1) and toll-like receptors (TLRs). In the IRAK family, 4 members have been identified namely IRAK 1-4 (Wang et al. 2009), and IRAK-4, the newest member of the family represents an attractive therapeutic target (Li et al. 2002). Indeed, IRAK-4 is believed to be the key protein kinase activated early downstream of the IL-1 receptor and TLRs (except TLR3), initiating signaling via rapid activation of IRAK-1 and IRAK-2, leading to innate immune responses. Also, other interleukins, such as IL-18 and IL-33, are dependent on IRAK-4 for signaling. As such, diseases for which these cytokines are involved in the pathogenic process (e.g., fibrosis (Li et al. 2014; McHedlidze et al. 2013; Rankin et al. 2010) and atopic dermatitis (Salimi et al. 2013)) are potential target diseases for treatment by IRAK-4 inhibitors.

In mice expressing an inactive IRAK-4 mutant instead of wild type, complete resistance to septic shock triggered by several TLR agonists as well as impaired response to IL-1 is observed. Furthermore, mice expressing an inactive IRAK-4 mutant instead of wild type are partially protected in several models of auto-immune diseases, such as rheumatoid arthritis (Koziczak-Holbro et al. 2009) and multiple sclerosis (Staschke et al. 2009). Interestingly, the serum of rheumatoid arthritis and systemic lupus erythematosus patients has been shown to activate plasmacytoid dendritic cells in an IRAK-4 dependent manner (Chiang et al. 2011). Finally, recurring pyogenic bacterial infection has been observed in children suffering from genetic defects leading to IRAK-4 inactivity. As these pyogenic infections are not observed in adults carrying inactivating IRAK-4 mutations, the IRAK-4 signaling system appears to be redundant for certain aspects of adult innate immunity.

The dysregulation of signaling components of the innate immune system is also increasingly being recognized as an important factor in cancer initiation and progression (Rhyasen & Starczynowski 2015). Indeed, there is evidence that IL-1 plays a direct role in tumor cell growth, angiogenesis, invasion, drug resistance, and metastasis (Carmi et al. 2013; Vidal-Vanaclocha et al. 2000). Additionally, TLRs are involved in a multitude of protumor responses, depending on the tumor cell context. As essential mediators of IL-1 receptor and TLRs signaling, IRAK family kinases represent promising cancer drug targets. In addition, several cancer types have been shown to be dependent on activated forms of MYD88, an adaptor molecule downstream of the TLR and IL-1R, which activates IRAK-4. Activating MYD88 mutations have been identified in e.g., diffuse large B-cell lymphomas (DLBCL) (Ngo et al. 2011), and in Waldenstrom macroglobulinemia (Treon et al. 2012). Another report supports the role of IRAK-4 in the field of oncology, T-cell acute lymphoblastic leukemia (T-ALL) in particular (Li et al. 2015). The pharmacological inhibition of IRAK-4 has been shown to enhance the sensitivity of T-ALL to chemotherapeutic agents.

IL-33 has been shown to play a role in the development of fibrotic and allergic diseases, asthma and atopic dermatitis in particular (Nabe 2014). As this cytokine signals through an IRAK-4 dependent pathway (Kroeger et al. 2009), these diseases might also represent a target for IRAK-4 inhibitors.

Finally, several auto-inflammatory diseases have been shown to be dependent on IL-1 activity and, as a consequence, IL-1 blocking biologicals show some benefit to these patients. Gout, juvenile idiopathic arthritis, Muckle-Wells disease, familial Mediterranean fever, Behçet's disease, adult onset Still's disease are examples of such auto-inflammatory diseases (Dinarello et al. 2012).

The inhibition of cytokine signaling with small molecules may help in reducing disease outcome in immune-inflammatory diseases (Sundberg et al. 2014). In particular, cytokines may play a role in the defense of organisms against pathogens and infections. However, when developing new therapies for immune-inflammatory diseases, it is crucial on one hand to select a target involved in a pathway that can be inhibited without compromising the adaptive and/or innate immune responses since the simultaneous inhibition of multiple cytokine response pathways may excessively weaken the immune system. However, drug selectivity towards kinases is difficult to achieve (Bain et al. 2003; Fabian et al. 2005), but is highly desirable in order to avoid off-target associated side effects, particularly in the context of chronic treatments (Broekman et al. 2011; Dy & Adjei 2013; Force & Kolaja 2011).

In particular, it was recently shown that concomitant use of an IL-1 blocking agent (Anakinra) and a TNFα blocker (Etanercept) resulted in increased risk of neutropenia and infection. (Genovese et al., 2003, EMEA public statement EMEA/31631/02, 5 Feb. 2003). This finding highlights that selectivity is a crucial element when developing new medicines, and therefore, it would be desirable to develop compounds that are able to selectively modulate a signaling pathway without affecting others, in particular compounds able to selectively modulate IL-1 response, without affecting TNF, signaling pathways.

The current therapies are not satisfactory and therefore there remains a need to identify further compounds with reduced off-target related side effects that may be of use in the prophylaxis and/or treatment of inflammatory diseases, autoimmune diseases and/or proliferative diseases.

SUMMARY OF THE INVENTION

The present invention is based on the identification of novel compounds, and their use in the prophylaxis and/or treatment of inflammatory diseases, autoimmune diseases and/or proliferative diseases. In particular, the compounds of the invention may be IRAK inhibitors, and more particularly IRAK-4 inhibitors. The present invention also provides methods for the production of these compounds, pharmaceutical compositions comprising these compounds and methods for the prophylaxis and/or treatment of inflammatory diseases, autoimmune diseases and/or proliferative diseases by administering the compounds of the invention.

Accordingly, in a first aspect of the invention, the compounds of the invention are provided having a Formula (I):

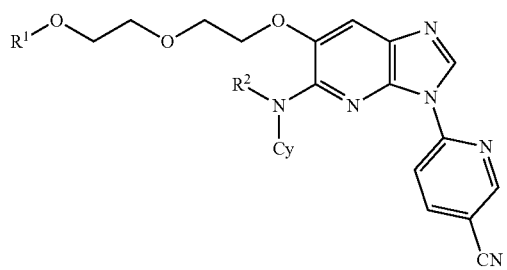

wherein
Cy is
  monocyclic $C_{3-7}$ cycloalkyl optionally substituted with one or more independently selected $R^3$, or
  4-7 membered monocyclic heterocycloalkyl comprising one or two heteroatoms independently selected from N, S, and O, optionally substituted with one or more independently selected $R^3$;
$R^1$ is
  H,
  —SO$_3$H,
  —P(=O)(OH)$_2$,
  $C_{1-4}$ alkyl,
  —C(=O)-(4-7 membered monocyclic heterocycloalkyl comprising one or two heteroatoms independently selected from N, S, and O), or
  —C(=O)C$_{1-6}$ alkyl, which C$_{1-6}$ alkyl is optionally substituted with one or more independently selected $R^4$ groups;
$R^2$ is H or $C_{1-4}$ alkyl;
each $R^3$ is independently selected from:
  OH,
  =O,
  halo, and
  $C_{1-4}$ alkyl;

each $R^4$ is independently selected from:
  —NR$^{5a}$R$^{5b}$,
  —C(=O)OH,
  4-7 membered monocyclic heterocycloalkyl comprising one or two heteroatoms independently selected from N, S, and O, optionally substituted with one or more independently selected $C_{1-4}$ alkyl, and
  —NHC(=O)—$C_{1-4}$ alkyl-NH$_2$; and
$R^{5a}$ and $R^{5b}$ are independently H or $C_{1-4}$ alkyl.

In one aspect, the compounds of the invention are provided for use in the prophylaxis and/or treatment of inflammatory diseases, autoimmune diseases and/or proliferative diseases. In a particular aspect, the compounds of the invention may inhibit the IRAK kinase family members, and more particularly IRAK-4. In another particular aspect, the compounds of the invention, compared to closely related analogs, may show improved selectivity towards IRAK family kinases, and more particularly IRAK-4, thus resulting in reduced off-target related toxicity. In a further aspect, the compounds of the invention may exhibit good metabolic stability, which may result in improved oral bioavailability.

In yet a further aspect, the compounds of the invention may show selectivity towards IRAK-4, which may result in improved safety and lower off-target related side effects. In a particular aspect, the compounds of the invention may be selective inhibitors of IL-1.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the prophylaxis and/or treatment of inflammatory diseases, autoimmune diseases, and/or proliferative diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory diseases, autoimmune diseases and/or proliferative diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory diseases, autoimmune diseases and/or proliferative diseases.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl (—CH$_3$), ethyl (—CH$_2$—CH$_3$), n-propyl (—CH$_2$—CH$_2$—CH$_3$), isopropyl (—CH(CH$_3$)$_2$), n-butyl (—CH$_2$—CH$_2$—CH$_2$—CH$_3$), tert-butyl (—CH$_2$—C(CH$_3$)$_3$), sec-butyl (—CH$_2$—CH(CH$_3$)$_2$), n-pentyl (—CH$_2$—CH$_2$—CH$_2$—CH$_2$—CH$_3$), n-hexyl (—CH$_2$—CH$_2$—CH$_2$—CH$_2$—CH$_2$—CH$_3$), and 1,2-dimethylbutyl (—CHCH$_3$)—C(CH$_3$)H$_2$—CH$_2$—CH$_3$). Particular alkyl groups have between 1 and 4 carbon atoms.

'Alkoxy' refers to the group O-alkyl, where the alkyl group has the number of carbon atoms specified. In particular the term refers to the group —O—C$_{1-6}$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$) and the like.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocycloalkyl, aryl, e.g., heteroaryl, and the like having from 1 to 4, and particularly from 1, 2 or 3 heteroatoms, more typically one or two heteroatoms, for example a single heteroatom.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g., 1-pyrrolidinyl, 2-pyrrolidinyl and 3-pyrrolidinyl), tetrahydrofuranyl (e.g., 1-tetrahydrofuranyl, 2-tetrahydrofuranyl and 3-tetrahydrofuranyl), tetrahydrothiophenyl (e.g., 1-tetrahydrothiophenyl, 2-tetrahydrothiophenyl and 3-tetrahydrothiophenyl), piperidinyl (e.g., 1-piperidinyl, 2-piperidinyl, 3-piperidinyl and 4-piperidinyl), tetrahydropyranyl (e.g., 4-tetrahydropyranyl), tetrahydrothiopyranyl (e.g., 4-tetrahydrothiopyranyl), morpholinyl, thiomorpholinyl, dioxanyl, or piperazinyl.

Particular examples of monocyclic rings are shown in the following illustrative examples:

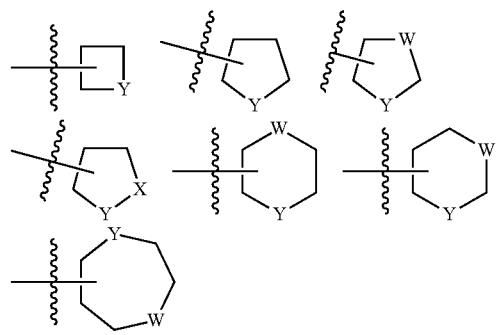

wherein each W and Y is independently selected from —CH$_2$—, —NH—, —O— and —S—.

Particular examples of fused bicyclic rings are shown in the following illustrative examples:

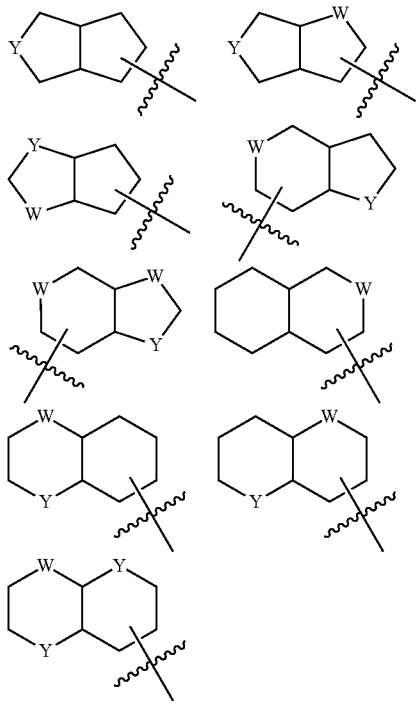

wherein each W and Y is independently selected from —CH₂—, —NH—, —O— and —S—.

Particular examples of bridged bicyclic rings are shown in the following illustrative examples:

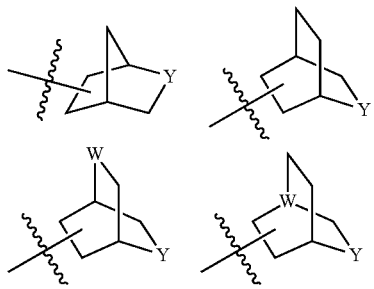

wherein each W and Y is independently selected from —CH₂—, —NH—, —O— and —S—.

Particular examples of spirocyclic rings are shown in the following illustrative examples:

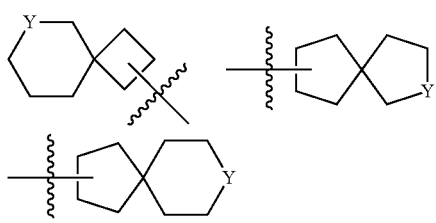

wherein each Y is selected from —CH₂—, —NH—, —O— and —S—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —SO₃H.

As used herein, the term 'substituted with one or more' refers to one to four substituents. In one embodiment it refers to one to three substituents. In further embodiments it refers to one or two substituents. In a yet further embodiment it refers to one substituent.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or state government, or the corresponding agency in countries other than the United States, or that is listed in the U.S. Pharmacopeia or other generally recognized pharmacopeias for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminium ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g., in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The 'effective amount' can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, 'treating' or 'treatment' relates to slowing the progression of the disease.

As used herein the term 'allergic disease(s)' refers to the group of conditions characterized by a hypersensitivity disorder of the immune system including, allergic airway disease (e.g., asthma, rhinitis), atopic dermatitis, sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'inflammatory disease(s)' refers to the group of conditions including rheumatoid arthritis, osteoarthritis, juvenile idiopathic arthritis, psoriasis, psoriatic arthritis, ankylosing spondylitis, allergic airway disease (e.g., asthma, rhinitis), chronic obstructive pulmonary disease (COPD), inflammatory bowel diseases (IBD, e.g., Crohn's disease, ulcerative colitis), irritable bowel syndrome, endotoxin-driven disease states (e.g., complications after bypass surgery or chronic endotoxin states contributing to e.g., chronic cardiac failure), adult-onset Still's disease, Muckle-Wells syndrome, familial cold autoinflammatory syndrome (FCAS), Beh9et's disease, familial Mediterranean fever, gout, neonatal onset multisystem inflammatory disease (NOMID), Schnitzler syndrome, and related diseases involving cartilage, such as that of the joints. Particularly the term refers to rheumatoid arthritis, juvenile idiopathic arthritis, psoriasis, osteoarthritis, allergic airway disease (e.g., asthma), chronic obstructive pulmonary disease (COPD) and inflammatory bowel diseases. More particularly the term refers to rheumatoid arthritis, juvenile idiopathic arthritis, psoriasis, chronic obstructive pulmonary disease (COPD) and inflammatory bowel diseases.

As used herein the term 'autoimmune disease(s)' refers to the group of diseases including obstructive airways disease, including conditions such as COPD, asthma (e.g., intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g., Crohn's disease and ulcerative colitis), atherosclerosis and amyotrophic lateral sclerosis. Particularly the term refers to COPD, asthma, systemic lupus erythematosus, type I diabetes mellitus and inflammatory bowel disease.

As used herein, the term 'fibrosis' refers to systemic sclerosis, idiopathic pulmonary fibrosis and other forms of lung fibrosis and interstitial lung diseases, alcoholic steatohepatitis, non-alcoholic steatohepatitis, renal fibrosis, and fibrosis of the colon as a consequence of inflammatory bowel diseases.

As used herein the term 'proliferative disease(s)' refers to conditions such as cancer (e.g., uterine leiomyosarcoma or prostate cancer), myeloproliferative disorders (e.g., polycythemia vera, essential thrombocytosis and myelofibrosis), leukemia (e.g., acute myeloid leukemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasize) to distant organs, for example to bone, liver, lung or the brain. As used herein the term cancer includes both metastatic tumor cell types (such as but not limited to, melanoma, lymphoma, leukemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-cell lymphoma, embryonal tumors, endometrial cancer, ependymoblastoma, ependymoma, esophageal cancer, Ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, Kaposi sarcoma, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilm's tumor As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukemia (AML), and acute lymphoblastic leukemia (ALL) and chronic lymphoblastic leukemia (CLL).

'Compound(s) of the invention', and equivalent expressions, are meant to embrace compounds of the Formula(e) as herein described, which expression includes the pharmaceutically acceptable salts, and the solvates, e.g., hydrates, and the solvates of the pharmaceutically acceptable salts, where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and $(C_{6-10}$ aryl)-$(C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers, respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

THE INVENTION

The present invention is based on the identification of novel compounds, their use in the prophylaxis and/or treatment of inflammatory diseases, autoimmune diseases and/or proliferative diseases. In particular, the compounds may inhibit IRAKs, and more particularly IRAK-4.

The present invention also provides methods for the production of these compounds, pharmaceutical compositions comprising these compounds and methods of prophylaxis and/or treatment of inflammatory diseases, autoimmune diseases and/or proliferative diseases by administering the compounds of the invention.

Accordingly, in a first aspect of the invention, the compounds of the invention are provided having a Formula (I):

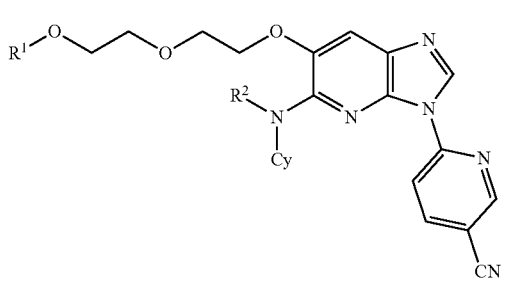

wherein
Cy is
    monocyclic $C_{3-7}$ cycloalkyl optionally substituted with one, two or three independently selected $R^3$, or
    4-7 membered monocyclic heterocycloalkyl comprising one or two heteroatoms independently selected from N, S, and O, optionally substituted with one, two or three independently selected $R^3$;

$R^1$ is
    —H,
    —$SO_3H$,
    —$P(=O)(OH)_2$,
    $C_{1-4}$ alkyl,
    —C(=O)-(4-7 membered monocyclic heterocycloalkyl comprising one or two heteroatoms independently selected from N, S, and O), or
    —C(=O)$C_{1-6}$ alkyl, which $C_{1-6}$ alkyl is optionally substituted with one or more independently selected $R^4$;
$R^2$ is H or $C_{1-4}$ alkyl;
each $R^3$ is independently selected from:
    —OH,
    =O,
    halo, and
    $C_{1-4}$ alkyl;
each $R^4$ is independently selected from:
    —$NR^{5a}R^{5b}$,
    —C(=O)OH,
    4-7 membered monocyclic heterocycloalkyl comprising one or two heteroatoms independently selected from N, S, and O, optionally substituted with one or more independently selected $C_{1-4}$ alkyl, and
    —NHC(=O)—$C_{1-4}$ alkyl-$NH_2$; and
$R^{5a}$ and $R^{5b}$ are independently H or $C_{1-4}$ alkyl.

In one embodiment, the compound of the invention is according to Formula I, wherein Cy is monocyclic $C_{3-7}$ cycloalkyl. In a particular embodiment, Cy is cyclohexyl.

In one embodiment, the compound of the invention is according to Formula I, wherein Cy is monocyclic $C_{3-7}$ cycloalkyl substituted with one, two or three independently selected $R^3$. In a particular embodiment, Cy is cyclohexyl substituted with one, two or three independently selected $R^3$. In another particular embodiment, Cy is monocyclic $C_{3-7}$ cycloalkyl substituted with one or two $R^3$. In a more particular embodiment, Cy is cyclohexyl substituted with one or two independently selected $R^3$.

In one embodiment, the compound of the invention is according to Formula I, wherein Cy is 4-7 membered monocyclic heterocycloalkyl comprising one or two heteroatoms independently selected from N, S, and O. In a particular embodiment, Cy is tetrahydropyranyl, or tetrahydrothiopyranyl. In a more particular embodiment, Cy is

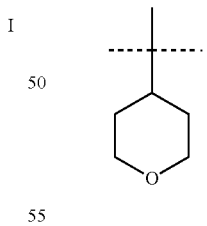

In one embodiment, the compound of the invention is according to Formula I, wherein Cy is monocyclic 4-7 membered monocyclic heterocycloalkyl comprising one or two heteroatoms independently selected from N, S, and O, substituted with one, two or three independently selected $R^3$. In another embodiment, Cy is tetrahydropyranyl or tetrahydrothiopyranyl, each of which is substituted with one, two or three independently selected $R^3$. In a particular embodiment, Cy is 4-7 membered monocyclic heterocycloalkyl comprising one or two heteroatoms independently selected from N, S, and O, substituted with one or two $R^3$. In another particular embodiment, Cy is tetrahydropyranyl, or tetrahydrothiopyranyl, each of which is substituted with one or two independently selected R³. In a more particular embodiment, Cy is

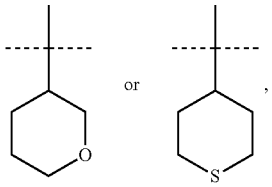

each of which is substituted with one or two independently selected R³.

In one embodiment, the compound of the invention is according to Formula I, wherein each R³ is selected from OH, =O, halo, and $C_{1-4}$ alkyl. In a particular, embodiment, each R³ is selected from OH, =O, F, and —CH₃. In a more particular embodiment, each R³ is selected from OH, and —CH₃. In another more particular embodiment, each R³ is F. In yet another more particular embodiment, each R³ is =O.

In one embodiment, the compound of the invention is according to Formula IIa, IIb, IIc, IId, IIe, or IIf:

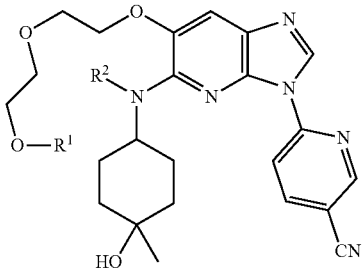

IIa

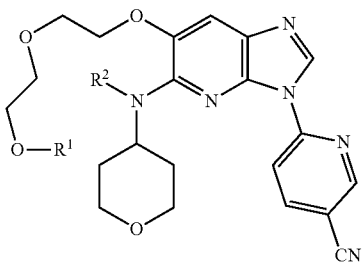

IIb

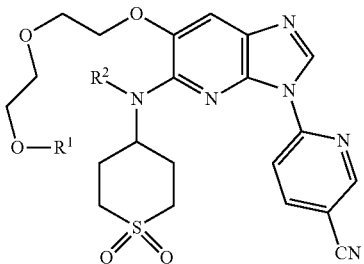

IIc

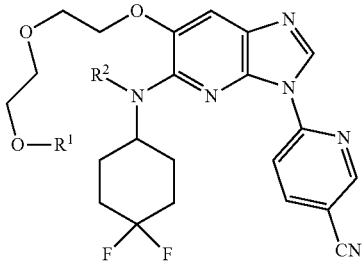

IId

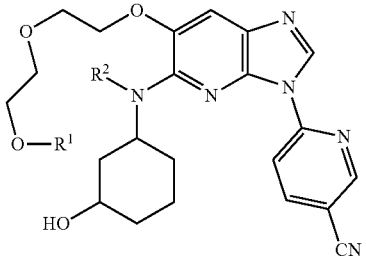

IIe

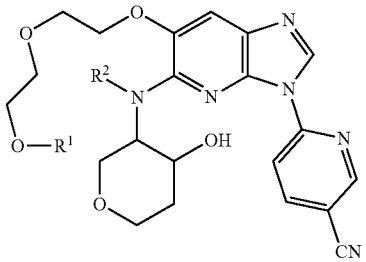

IIf wherein R¹ and R² are as described above.

In one embodiment, the compound of the invention is according to any one of Formulae I-IIf, wherein R¹ is H, —SO₃H, or —P(=O)(OH)₂.

In one embodiment, the compound of the invention is according to any one of Formulae I-IIf, wherein R¹ is $C_{1-4}$ alkyl. In a particular embodiment, R¹ is —CH₃, —CH₂CH₃, or —CH(CH₃)₂. In a more particular embodiment, R¹ is —CH₃.

In one embodiment, the compound of the invention is according to any one of Formulae I-IIf, wherein R¹ is —C(=O)-(4-7 membered monocyclic heterocycloalkyl comprising one or two heteroatoms independently selected from N, S, and O). In a particular embodiment, R¹ is —C(=O)-pyrrolidinyl.

In one embodiment, the compound of the invention is according to any one of Formulae I-IIf, wherein R¹ is —C(=O)$C_{1-6}$ alkyl. In a particular embodiment, R¹ is —C(=O)$C_{1-6}$ alkyl, which $C_{1-6}$ alkyl is selected from —CH₃, —CH₂CH₃, —CH₂CH₂CH₃, or —CH₂(CH(CH₃)₂).

In one embodiment, the compound of the invention is according to any one of Formulae I-IIf, wherein R¹ is —C(=O)$C_{1-6}$ alkyl, which $C_{1-6}$ alkyl is substituted with one or more independently selected R⁴. In a particular embodiment, R¹ is —C(=O)$C_{1-6}$ alkyl, which $C_{1-6}$ alkyl is selected from —CH₃, —CH₂CH₃, —CH₂CH₂CH₃, or —CH₂(CH(CH₃)₂), each of which is substituted with one or more independently selected R⁴. In another particular embodiment, R¹ is —C(=O)$C_{1-6}$ alkyl, which $C_{1-6}$ alkyl is substituted with one or two independently selected R⁴. In a more particular embodiment, R¹ is —C(=O)$C_{1-6}$ alkyl, which $C_{1-6}$ alkyl is selected from —CH₃, —CH₂CH₃, —CH₂CH₂CH₃, or —CH₂(CH(CH₃)₂), each of which is substituted with one or two independently selected $R^4$.

In one embodiment, the compound of the invention is according to any one of Formulae I-IIf, and $R^4$ is —$NR^{5a}R^{5b}$, wherein each $R^{5a}$ and $R^{5b}$ is independently H or $C_{1-4}$ alkyl. In a particular embodiment, each $R^{5a}$ and $R^{5b}$ is independently H, —CH₃, or —CH₂CH₃. In a more particular embodiment, $R^{5a}$ is H, and $R^{5b}$ is H, —CH₃, or —CH₂CH₃. In a most particular embodiment, $R^4$ is —NH₂, —NHCH₃, or —N(CH₃)₂.

In one embodiment, the compound of the invention is according to any one of Formulae I-IIf, wherein $R^4$ is —C(=O)OH.

In one embodiment, the compound of the invention is according to any one of Formulae I-IIf, wherein $R^4$ is 4-7 membered monocyclic heterocycloalkyl comprising one or two heteroatoms independently selected from N, S, and O, optionally substituted with one or more independently selected $C_{1-4}$ alkyl. In a particular embodiment, $R^4$ is morpholinyl, piperidinyl, or piperazinyl, each of which is optionally substituted with one or more independently selected $C_{1-4}$ alkyl. In another particular embodiment, $R^4$ is 4-7 membered monocyclic heterocycloalkyl comprising one or two heteroatoms independently selected from N, S, and O, optionally substituted with one $C_{1-4}$ alkyl. In a more particular embodiment, $R^4$ is 4-7 membered monocyclic heterocycloalkyl comprising one or two heteroatoms independently selected from N, S, and O, optionally substituted with one —CH₃. In another more particular embodiment, $R^4$ is morpholinyl, piperidinyl, or piperazinyl, each of which is optionally substituted with one or more —CH₃. In a most particular embodiment, $R^4$ is morpholinyl, piperidinyl, or piperazinyl, each of which is optionally substituted with one —CH₃.

In one embodiment, the compound of the invention is according to any one of Formulae I-IIf, wherein $R^4$ is —NHC(=O)—$C_{1-4}$ alkyl-NH₂. In a particular embodiment, $R^4$ is —NHC(=O)—CH₂—NH₂.

In one embodiment, the compound of the invention is according to any one of Formulae I-IIf, wherein $R^1$ is —C(=O)CH₂NH₂, —C(=O)CH₂NHCH₃, —C(=O)CH₂N(CH₃)₂, —C(=O)CH₂CH₂N(CH₃)₂, —C(=O)CH(NH₂)CH(CH₃)₂, —C(=O)CH₂CH₂C(=O)OH, —C(=O)CH(NH₂)CH₂C(=O)OH, —C(=O)CH(NH₂)CH₂CH₂C(=O)OH, —C(=O)CH(CH(CH₃)₂)NHC(=O)CH₂NH₂,

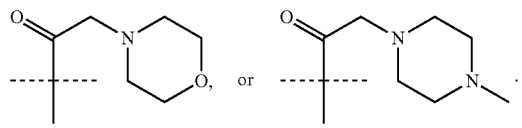

In one embodiment, the compound of the invention is according to any one of Formulae I-IIf, wherein $R^2$ is H.

In one embodiment, the compound of the invention is according to any one of Formulae I-IIf, wherein $R^2$ is $C_{1-4}$ alkyl. In a particular embodiment, $R^2$ is —CH₃.

In one embodiment, the compound of the invention is according to Formula I, wherein the compound is selected from:
6-[6-[2-(2-hydroxy-ethoxy)-ethoxy]-5-(tetrahydro-pyran-4-ylamino)-imidazo[4,5-b]pyridin-3-yl]-nicotinonitrile,
6-{5-(1,1-dioxo-tetrahydro-2H-thiopyran-4-ylamino)-6-[2-(2-hydroxy-ethoxy)-ethoxy]-imidazo[4,5-b]pyridin-3-yl}-nicotinonitrile,
6-{6-[2-(2-hydroxy-ethoxy)-ethoxy]-5-[((cis-1,4)-4-hydroxy-4-methyl-cyclohexyl)-methyl-amino]-imidazo[4,5-b]pyridin-3-yl}-nicotinonitrile,
6-{6-[2-(2-methoxy-ethoxy)-ethoxy]-5-[methyl-(tetrahydro-pyran-4-yl)-amino]-imidazo[4,5-b]pyridin-3-yl}-nicotinonitrile,
6-[6-[2-(2-methoxy-ethoxy)-ethoxy]-5-(tetrahydro-pyran-4-ylamino)-imidazo[4,5-b]pyridin-3-yl]-nicotinonitrile,
6-{5-(3-hydroxy-cyclohexylamino)-6-[2-(2-hydroxy-ethoxy)-ethoxy]-imidazo[4,5-b]pyridin-3-yl}-nicotinonitrile,
6-{5-(4,4-difluoro-cyclohexylamino)-6-[2-(2-hydroxy-ethoxy)-ethoxy]-imidazo[4,5-b]pyridin-3-yl}-nicotinonitrile,
sulfuric acid mono-(2-{2-[3-(5-cyano-pyridin-2-yl)-5-(tetrahydro-pyran-4-ylamino)-3H-imidazo[4,5-b]pyridin-6-yloxy]-ethoxy}-ethyl) ester,
(S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester,
(S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester oxalic acid salt,
6-[6-[2-(2-hydroxyethoxy)ethoxy]-5-[[(cis-3,4)-4-hydroxytetrahydropyran-3-yl]amino]imidazo[4,5-b]pyridin-3-yl]pyridine-3-carbonitrile,
6-[6-[2-(2-hydroxyethoxy)ethoxy]-5-[((cis-1,4)-4-hydroxy-4-methylcyclohexyl)amino]imidazo[4,5-b]pyridin-3-yl]pyridine-3-carbonitrile,
6-[5-[((cis-1,4)-4-hydroxy-4-methyl-cyclohexyl)-methyl-amino]-6-[2-(2-methoxyethoxy)ethoxy]imidazo[4,5-b]pyridin-3-yl]pyridine-3-carbonitrile,
6-[5-[((cis-1,4)-4-hydroxy-4-methylcyclohexyl)amino]-6-[2-(2-methoxyethoxy)ethoxy]imidazo[4,5-b]pyridin-3-yl]pyridine-3-carbonitrile,
2-[2-[3-(5-cyano-2-pyridyl)-5-(tetrahydropyran-4-ylamino)imidazo[4,5-b]pyridin-6-yl]oxyethoxy]ethyl 2-(dimethylamino)acetate,
2-[2-[3-(5-cyano-2-pyridyl)-5-(tetrahydropyran-4-ylamino)imidazo[4,5-b]pyridin-6-yl]oxyethoxy]ethyl 2-aminoacetate,
2-[2-[3-(5-cyano-2-pyridyl)-5-(tetrahydropyran-4-ylamino)imidazo[4,5-b]pyridin-6-yl]oxyethoxy]ethyl 2-(methylamino)acetate,
2-[2-[3-(5-cyano-2-pyridyl)-5-(tetrahydropyran-4-ylamino)imidazo[4,5-b]pyridin-6-yl]oxyethoxy]ethyl (2S)-pyrrolidine-2-carboxylate,
2-[2-[3-(5-cyano-2-pyridyl)-5-(tetrahydropyran-4-ylamino)imidazo[4,5-b]pyridin-6-yl]oxyethoxy]ethyl (2S)-2-[(2-aminoacetyl)amino]-3-methyl-butanoate,
2-[2-[3-(5-cyano-2-pyridyl)-5-(tetrahydropyran-4-ylamino)imidazo[4,5-b]pyridin-6-yl]oxyethoxy]ethyl 2-morpholinoacetate,
2-[2-[3-(5-cyano-2-pyridyl)-5-(tetrahydropyran-4-ylamino)imidazo[4,5-b]pyridin-6-yl]oxyethoxy]ethyl 2-(4-methylpiperazin-1-yl)acetate,
2-[2-[3-(5-cyano-2-pyridyl)-5-(tetrahydropyran-4-ylamino)imidazo[4,5-b]pyridin-6-yl]oxyethoxy]ethyl 3-(dimethylamino)propanoate,
2-[2-[3-(5-cyano-2-pyridyl)-5-(tetrahydropyran-4-ylamino)imidazo[4,5-b]pyridin-6-yl]oxyethoxy]ethyl 2-(dimethylamino)acetate oxalic acid salt,
2-[2-[3-(5-cyano-2-pyridyl)-5-(tetrahydropyran-4-ylamino)imidazo[4,5-b]pyridin-6-yl]oxyethoxy]ethyl 2-aminoacetate oxalic acid salt, 2-[2-[3-(5-cyano-2-pyridyl)-5-(tetrahydropyran-4-ylamino) imidazo[4,5-b]pyridin-6-yl]oxyethoxy]ethyl 2-(methylamino)acetate oxalic acid salt, 2-[2-[3-(5-cyano-2-pyridyl)-5-(tetrahydropyran-4-ylamino) imidazo[4,5-b]pyridin-6-yl]oxyethoxy]ethyl (2S)-pyrrolidine-2-carboxylate oxalic acid salt, (3 S)-3-amino-4-[2-[2-[3-(5-cyano-2-pyridyl)-5-(tetrahydropyran-4-ylamino)imidazo[4,5-b]pyridin-6-yl]oxyethoxy]ethoxy]-4-oxo-butanoic acid hydrochloric acid salt, (4S)-4-amino-5-[2-[2-[3-(5-cyano-2-pyridyl)-5-(tetrahydropyran-4-ylamino)imidazo[4,5-b]pyridin-6-yl]oxyethoxy] ethoxy]-5-oxo-pentanoic acid hydrochloric acid salt, 2-[2-[3-(5-cyano-2-pyridyl)-5-(tetrahydropyran-4-ylamino) imidazo[4,5-b]pyridin-6-yl]oxyethoxy]ethyl (2S)-2-[(2-aminoacetyl)amino]-3-methyl-butanoate oxalic acid salt, 2-[2-[3-(5-cyano-2-pyridyl)-5-(tetrahydropyran-4-ylamino) imidazo[4,5-b]pyridin-6-yl]oxyethoxy]ethyl 2-morpholinoacetate oxalic acid salt, 2-[2-[3-(5-cyano-2-pyridyl)-5-(tetraydropyran-4-ylamino) imidazo[4,5-b]pyridin-6-yl]oxyethoxy]ethyl 2-(4-methylpiperazin-1-yl)acetate oxalic acid salt, 2-[2-[3-(5-cyano-2-pyridyl)-5-(tetrahydropyran-4-ylamino) imidazo[4,5-b]pyridin-6-yl]oxyethoxy]ethyl 3-(dimethylamino)propanoate oxalic acid salt, and 4-[2-[2-[3-(5-cyano-2-pyridyl)-5-(tetrahydropyran-4-ylamino)imidazo[4,5-b]pyridin-6-yl]oxyethoxy]ethoxy]-4-oxo-butanoic acid.

In one embodiment, the compound of the invention is according to Formula I, wherein the compound is 6-[6-[2-(2-hydroxy-ethoxy)-ethoxy]-5-(tetrahydro-pyran-4-ylamino)-imidazo[4,5-b]pyridin-3-yl]-nicotinonitrile.

In one embodiment, the compound of the invention is according to Formula I, wherein the compound is not 6-[6-[2-(2-hydroxy-ethoxy)-ethoxy]-5-(tetrahydro-pyran-4-ylamino)-imidazo[4,5-b]pyridin-3-yl]-nicotinonitrile.

In one embodiment, the compound of the invention is according to Formula I, wherein the compound is (S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester.

In one embodiment, the compound of the invention is according to Formula I, wherein the compound is not (S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primojel®, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g), methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of inflammatory diseases, autoimmune diseases and/or proliferative diseases.

In another embodiment, the present invention provides compounds of the invention, or pharmaceutical compositions comprising a compound of the invention for use in the manufacture of a medicament for use in the prophylaxis and/or treatment of inflammatory diseases, autoimmune diseases and/or proliferative diseases.

In additional method of treatment aspects, this invention provides methods of prophylaxis and/or treatment of a mammal afflicted with inflammatory diseases, autoimmune diseases and/or proliferative diseases, which methods comprise the administration of an effective amount of a compound of the invention or one or more of the pharmaceutical compositions herein described for the treatment or prophylaxis of said condition.

In one embodiment, the present invention provides pharmaceutical compositions comprising a compound of the invention, and another therapeutic agent. In a particular embodiment, the other therapeutic agent is an agent for the prophylaxis and/or treatment of inflammatory diseases, autoimmune diseases and/or proliferative diseases.

In one embodiment, the present invention provides compounds of the invention or pharmaceutical compositions comprising a compound of the invention, for use in the prophylaxis and/or treatment of inflammatory diseases. In a particular embodiment, the inflammatory disease is selected from rheumatoid arthritis, osteoarthritis, juvenile idiopathic arthritis, psoriasis, psoriatic arthritis, ankylosing spondylitis, allergic airway diseases (e.g., asthma, rhinitis), chronic obstructive pulmonary disease (COPD), inflammatory bowel diseases (e.g., Crohn's disease, ulcerative colitis), endotoxin-driven disease states (e.g., complications after bypass surgery or chronic endotoxin states contributing to e.g., chronic cardiac failure), and related diseases involving cartilage, such as that of the joints. More particularly, the inflammatory disease is psoriasis or juvenile idiopathic arthritis.

In another embodiment, the present invention provides compounds of the invention, or pharmaceutical compositions comprising a compound of the invention for use in the manufacture of a medicament for use in the prophylaxis and/or treatment of inflammatory diseases. In a particular embodiment, the inflammatory disease is selected from rheumatoid arthritis, osteoarthritis, juvenile idiopathic arthritis, psoriasis, psoriatic arthritis, ankylosing spondylitis, allergic airway diseases (e.g., asthma, rhinitis), chronic obstructive pulmonary disease (COPD), inflammatory bowel diseases (e.g., Crohn's disease, ulcerative colitis), endotoxin-driven disease states (e.g., complications after bypass surgery or chronic endotoxin states contributing to e.g., chronic cardiac failure), and related diseases involving cartilage, such as that of the joints. More particularly, the inflammatory disease is psoriasis or juvenile idiopathic arthritis.

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In a particular embodiment, the inflammatory disease is selected from rheumatoid arthritis, osteoarthritis, juvenile idiopathic arthritis, psoriasis, psoriatic arthritis, ankylosing spondylitis, allergic airway diseases (e.g., asthma, rhinitis), chronic obstructive pulmonary disease (COPD), inflammatory bowel diseases (e.g., Crohn's disease, ulcerative colitis), endotoxin-driven disease states (e.g., complications after bypass surgery or chronic endotoxin states contributing to e.g., chronic cardiac failure), and related diseases involving cartilage, such as that of the joints. More particularly, the inflammatory disease is psoriasis or juvenile idiopathic arthritis.

In one embodiment, the present invention provides compounds of the invention or pharmaceutical compositions comprising a compound of the invention, for use in the prophylaxis and/or treatment of autoimmune diseases. In a particular embodiment, the autoimmune disease is selected from obstructive airways disease, including conditions such as COPD, asthma (e.g., intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g., Crohn's disease and ulcerative colitis), atherosclerosis and amyotrophic lateral sclerosis. More particularly, the autoimmune disease is systemic lupus erythematosus.

In another embodiment, the present invention provides compounds of the invention, or pharmaceutical compositions comprising a compound of the invention for use in the manufacture of a medicament for use in the prophylaxis and/or treatment of autoimmune diseases. In a particular embodiment, the autoimmune disease is selected from obstructive airways disease, including conditions such as COPD, asthma (e.g., intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g., Crohn's disease and ulcerative colitis), atherosclerosis and amyotrophic lateral sclerosis. More particularly, the autoimmune disease is systemic lupus erythematosus.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In a particular embodiment, the autoimmune disease is selected from obstructive airways disease, including conditions such as COPD, asthma (e.g., intrinsic asthma, extrinsic asthma, dust asthma, infantile asthma) particularly chronic or inveterate asthma (for example late asthma and airway hyperresponsiveness), bronchitis, including bronchial asthma, systemic lupus erythematosus (SLE), cutaneous lupus erythematosus, lupus nephritis, dermatomyositis, Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g., Crohn's disease and ulcerative colitis), atherosclerosis and amyotrophic lateral sclerosis. More particularly, the autoimmune disease is systemic lupus erythematosus.

In one embodiment, the present invention provides compounds of the invention or pharmaceutical compositions comprising a compound of the invention, for use in the prophylaxis and/or treatment of proliferative diseases. In a particular embodiment, the proliferative disease is selected from cancer (e.g., uterine leiomyosarcoma or prostate cancer), myeloproliferative disorders (e.g., polycythemia vera, essential thrombocytosis and myelofibrosis), leukemia (e.g., acute myeloid leukemia, acute and chronic lymphoblastic leukemia), multiple myeloma, psoriasis, restenosis, scleroderma or fibrosis.

In another embodiment, the present invention provides compounds of the invention, or pharmaceutical compositions comprising a compound of the invention for use in the manufacture of a medicament for use in the prophylaxis and/or treatment of proliferative diseases. In a particular embodiment, the proliferative disease is selected from cancer (e.g., uterine leiomyosarcoma or prostate cancer), myeloproliferative disorders (e.g., polycythemia vera, essential thrombocytosis and myelofibrosis), leukemia (e.g., acute myeloid leukemia, acute and chronic lymphoblastic leukemia), multiple myeloma, psoriasis, restenosis, scleroderma or fibrosis.

In additional method of treatment aspects, this invention provides methods of prophylaxis and/or treatment of a mammal afflicted with a proliferative disease, which methods comprise the administration of an effective amount of a compound of the invention or one or more of the pharmaceutical compositions herein described for the treatment or prophylaxis of said condition. In a particular embodiment, the proliferative disease is selected from cancer (e.g., uterine leiomyosarcoma or prostate cancer), myeloproliferative disorders (e.g., polycythemia vera, essential thrombocytosis and myelofibrosis), leukemia (e.g., acute myeloid leukemia, acute and chronic lymphoblastic leukemia), multiple myeloma, psoriasis, restenosis, scleroderma or fibrosis.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g., azathioprine, corticosteroids (e.g., prednisolone or dexamethasone), cyclophosphamide, cyclosporin A, tacrolimus, mycophenolate, mofetil, muromonab-CD3 (OKT3, e.g., Orthoclone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g., rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: nintedanib, pirfenidone, methotrexate, leucovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g., Herceptin™), capecitabine, raloxifene hydrochloride, EGFR inhibitors (e.g., Iressa®, Tarceva™, Erbitux™), VEGF inhibitors (e.g., Avastin™), proteasome inhibitors (e.g., Velcade™), Glivec® and hsp90 inhibitors (e.g., 17-AAG). Additionally, the compound of the invention according to Formula I may be administered in combination with other therapies including, but not limited to, radiotherapy or surgery. In a specific embodiment the proliferative disorder is selected from fibrosis, cancer, myeloproliferative disorders or leukemia.

In one embodiment, a compound of the invention is co-administered with another therapeutic agent for the treatment and/or prophylaxis of autoimmune diseases, particular agents include but are not limited to: glucocorticoids, cytostatic agents (e.g., purine analogs), alkylating agents, (e.g., nitrogen mustards (cyclophosphamide), nitrosoureas, platinum coordination complexes), antimetabolites (e.g., methotrexate, azathioprine and mercaptopurine), cytotoxic antibiotics (e.g., dactinomycin, anthracyclines, mitomycin C, bleomycin, and mithramycin), antibodies (e.g., anti-CD20, anti-CD25 or anti-CD3 (OTK3) monoclonal antibodies, Atgam® and Thymoglobulin®), cyclosporin, tacrolimus, rapamycin (sirolimus), interferons (e.g., IFN-β), TNF-binding proteins (e.g., infliximab, etanercept, or adalimumab), mycophenolate, fingolimod and myriocin.

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g., salbutamol, levalbuterol, terbutaline and bitolterol), epinephrine (inhaled or tablets), anticholinergics (e.g., ipratropium bromide), and glucocorticoids (oral or inhaled). Long-acting β2-agonists (e.g., salmeterol, formoterol, bambuterol, and sustained-release oral albuterol), combinations of inhaled steroids and long-acting bronchodilators (e.g., fluticasone/salmeterol, budesonide/formoterol), leukotriene antagonists and synthesis inhibitors (e.g., montelukast, zafirlukast and zileuton), inhibitors of mediator release (e.g., cromoglycate and ketotifen), biological regulators of IgE response (e.g., omalizumab), antihistamines (e.g., cetirizine, cinnarizine, fexofenadine) and vasoconstrictors (e.g., oxymetazoline, xylometazoline, naphazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g., ipratropium), systemic steroids (oral or intravenous, e.g., prednisone, prednisolone, methylprednisolone, dexamethasone, or hydrocortisone), intravenous salbutamol, non-specific beta-agonists, injected or inhaled (e.g., epinephrine, isoetarine, isoproterenol, metaproterenol), anticholinergics (IV or nebulized, e.g., glycopyrrolate, atropine, ipratropium), methylxanthines (theophylline, aminophylline, bamiphylline), inhalation anesthetics that have a bronchodilatory effect (e.g., isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g., prednisone, budesonide) synthetic disease modifying, immunomodulatory agents (e.g., methotrexate, leflunomide, sulfasalazine, mesalazine, azathioprine, 6-mercaptopurine and cyclosporin) and biological disease modifying, immunomodulatory agents (infliximab, adalimumab, certolizumab, etrolizumab, vedolizumab, ustekinumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta®)), disease-modifying antirheumatic drugs (DMARDs) such as antimalarials (e.g., Plaquenil®, hydroxychloroquine), immunosuppressants (e.g., methotrexate and azathioprine), cyclophosphamide and mycophenolic acid, immunosuppressive drugs and analgesics, such as nonsteroidal anti-inflammatory drugs, opiates (e.g., dextropropoxyphene and co-codamol), opioids (e.g., hydrocodone, oxycodone, MS Contin®, or methadone) and the Duragesic® fentanyl transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (an IL-12 and IL-23 blocker). Additionally, a compound of the invention may be administered in combination with other therapies including, but not limited to phototherapy, or photochemotherapy (e.g., psoralen and ultraviolet A phototherapy (PUVA)).

In one embodiment, a compound of the invention is co-administered with another therapeutic agent for the treatment and/or prophylaxis of allergic reaction; particular agents include but are not limited to: antihistamines (e.g., cetirizine, diphenhydramine, fexofenadine, levocetirizine), glucocorticoids (e.g., prednisone, betamethasone, beclomethasone, dexamethasone), epinephrine, theophylline or anti-leukotrienes (e.g., montelukast or zafirlukast), anticholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

A compound of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Wiley-Blackwell; 4th Revised edition (2006), and references cited therein (Wuts & Greene 2006).

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica standard (30-70 μm). Thin layer chromatography is carried out using pre-coated silica gel 60 F-254 plates (thickness 0.25 mm). $^1$H NMR spectra are recorded on a 400 MHz Bruker Avance spectrometer or a 300 MHz Bruker Avance DPX spectrometer. Chemical shifts (δ) for $^1$H NMR spectra are reported in parts per million (ppm) relative to tetramethylsilane (δ 0.00) or the appropriate residual solvent peak as internal reference. Multiplicities are given as singlet (s), doublet (d), triplet (t), quartet (q), quintet (quin), multiplet (m) and broad (br). Electrospray MS spectra are obtained on a Waters platform LC/MS spectrometer or with a Waters Acquity UPLC with Waters Acquity PDA detector and SQD mass spectrometer. Columns used: UPLC BEH C18 1.7 μm, 2.1×5 mm VanGuard pre-column with Acquity UPLC BEH C18 1.7 μm, 2.1×30 mm column or Acquity UPLC BEH C18 1.7 μm, 2.1×50 mm column. All the methods are using MeCN/H$_2$O gradients. MeCN and H$_2$O contain either 0.1% formic acid or 0.05% NH$_3$. Preparative LCMS: columns used, Waters XBridge Prep C18 5 μm ODB 30×100 mm (preparative column) and Waters XBridge C18 5 μm, 4.6 mm×100 mm (analytical column). All the methods are using MeCN/H$_2$O gradients. MeCN and H$_2$O contain either 0.1% formic acid or 0.1% diethylamine.

TABLE I

List of abbreviations used in the experimental section.

| | |
|---|---|
| AcOH | acetic acid |
| APMA | 4-aminophenylmercuric acetate |
| aq. | aqueous |
| atm | atmosphere |
| BINAP | (+/−)-2,2'-bis(diphenylphosphino)-1,1'-binaphthyl |
| Boc | tert-butyloxy-carbonyl |
| br | broad signal |
| BSA | bovine serum albumin |
| Calc | calculated |
| Cpd | compound |
| d | doublet |
| δ | chemical shift |
| DCM | dichloromethane |
| dd | doublet of doublets |
| DIPEA | diisopropylethylamine |
| DMAP | dimethylaminopyridine |
| DMF | dimethylformamide |
| DMSO | dimethylsulfoxide |
| dt | doublet of triplets |
| DTT | dithiothreitol |
| EDCI | N-(3-dimethylaminopropyl)-N'-ethylcarbodiimide hydrochloride |
| EDTA | ethylenediaminetetraacetic acid |
| eq. | equivalent |
| ES− | electrospray negative |
| ES+ | electrospray positive |
| Et$_2$O | diethyl ether |
| EtOAc | ethyl acetate |
| EtOH | ethanol |
| g | gram |
| h | hour |
| HPLC | high performance liquid chromatography |
| Hz | hertz |
| Int | intermediate |
| iPrOH | isopropanol |
| LiOMe | lithium methoxide |
| LiOtBu | lithium tert-butoxide |

TABLE I-continued

List of abbreviations used in the experimental section.

| | |
|---|---|
| m | multiplet |
| MeCN | acetonitrile |
| MeOH | methanol |
| mg | milligram |
| MgOAc | magnesium acetate |
| MHz | megahertz |
| min | minute |
| mL | millilitre |
| mmol | millimole |
| mol | mole |
| MOPS | 3-(N-morpholino)propanesulfonic acid |
| MS | mass spectrometry |
| MW | molecular weight |
| N | normality |
| NaBH(OAc)$_3$ | sodium triacetoxyborohydride |
| NaOtBu | sodium tert-butylate |
| NBS | N-bromosuccinimide |
| NMR | nuclear magnetic resonance |
| Obsvd | observed |
| PBS | phosphate-buffered saline |
| PBST | phosphate-buffered saline with Tween 20 |
| Pd(OAc)$_2$ | palladium diacetate |
| Pd/C | palladium on carbon |
| ppm | part-per-million |
| q | quadruplet |
| qd | quadruplet of doublets |
| quin | quintet |
| r.t. | room temperature |
| s | singlet |
| sat. | saturated |
| SEM | standard error of the mean |
| t | triplet |
| td | triplet of doublets |
| TEA | triethylamine |
| TFA | trifluoroacetic acid |
| THF | tetrahydrofurane |
| UPLC | ultra-performance liquid chromatography |

Synthetic Preparation of the Compounds of the Invention

Example 1. General Synthetic Methods 1.1. Synthetic Methods Overview

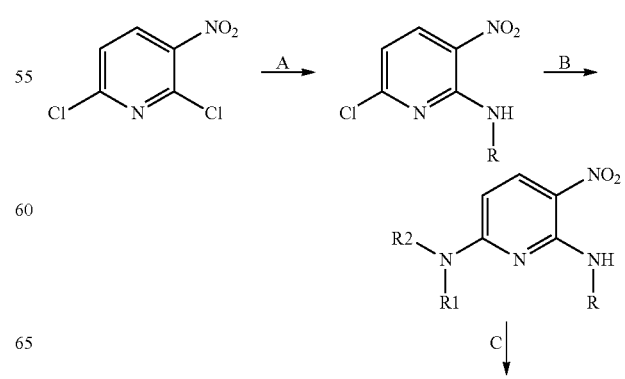

31
-continued

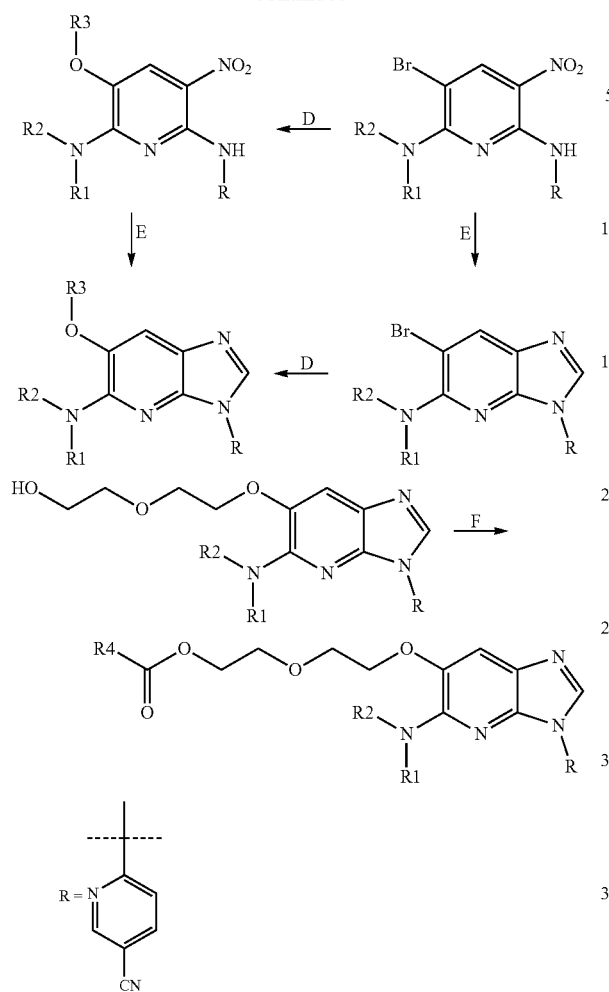

1.2. General Methods 1.2.1. General Method A

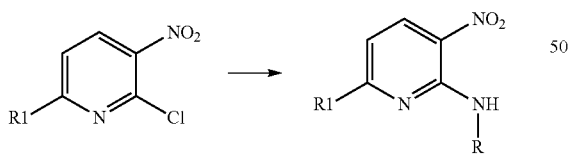

To a solution of NaH (2 eq., 60% in mineral oil) in dry THF cooled at 0° C. is added the corresponding 6-amino-nicotinonitrile (1.1 to 1.2 eq.). After 30 min at 0° C., the 2-chloro-3-nitropyridine (1 eq.) is added and the reaction is stirred at r.t. and monitored by UPLC-MS. If the reaction is not complete, the reaction is not complete, the reaction is cooled again at 0° C. and more NaH is added followed by more amine. The reaction mixture is poured into icy water and stirred for 2 h. The precipitate is filtered off, washed with $H_2O$, and air dried under vacuum to afford the desired compound.

32
Illustrative Synthesis of General Method A 6-(6-chloro-3-nitro-pyridin-2-ylamino)-nicotinonitrile (Int 1)

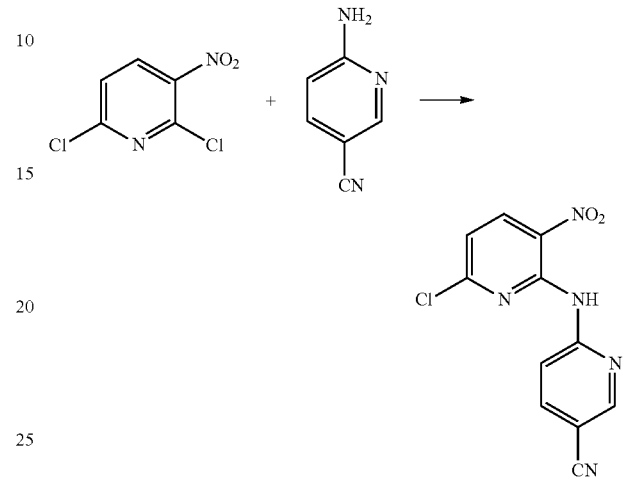

To a solution of NaH (2.07 g, 51.81 mmol, 2 eq., 60% in mineral oil) in dry THF (50 mL) cooled at 0° C. is added 6-amino-nicotinonitrile (3.4 g, 28.5 mmol, 1.1 eq.). After 30 min at 0° C., 2,6-dichloro-3-nitro-pyridine (5 g, 25.91 mmol, 1 eq.) is added and the reaction is stirred at r.t. for 16 h. The reaction is cooled to 0° C., NaH (0.5 g, 13 mmol, 0.5 eq.) is added and the reaction is stirred for 1 h at 0° C. then for 2 h at r.t. The reaction mixture is poured into icy water and stirred for 2 h. The precipitate is filtered off, washed with $H_2O$, and air dried under vacuum. The obtained solid is taken up in MeCN (75 mL), stirred at r.t. for 1 h 30 min and at 0° C. for 1 h. It is then filtered and washed with MeOH to afford the desired compound.

$^1$H NMR (400 MHz, DMSO-$d_6$) δ 10.81 (1H, br s), 8.73 (1H, dd), 8.61 (1H, d), 8.31 (1H, dd), 8.01 (1H, dd), 7.36 (1H, d).

1.2.2. General Method B

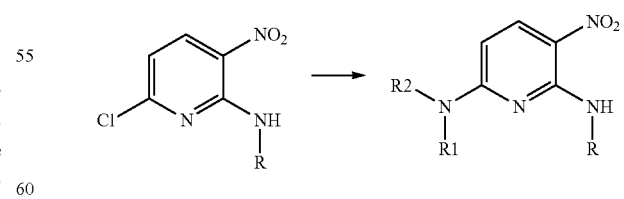

To 6-chloro-3-nitro-pyridin-2-ylamino derivative (1 eq.) in DMSO is added the corresponding amine (1.1 eq.) and DIPEA (2 eq.), the reaction mixture is then microwaved at 110-130° C. until completion of the reaction. The mixture is diluted with $H_2O$, the precipitate is filtered off and air dried under vacuum to give the desired compound.

Illustrative Synthesis of General Method B

6-[3-nitro-6-(tetrahydro-pyran-4-ylamino)-pyridin-2-ylamino]-nicotinonitrile (Int 8)

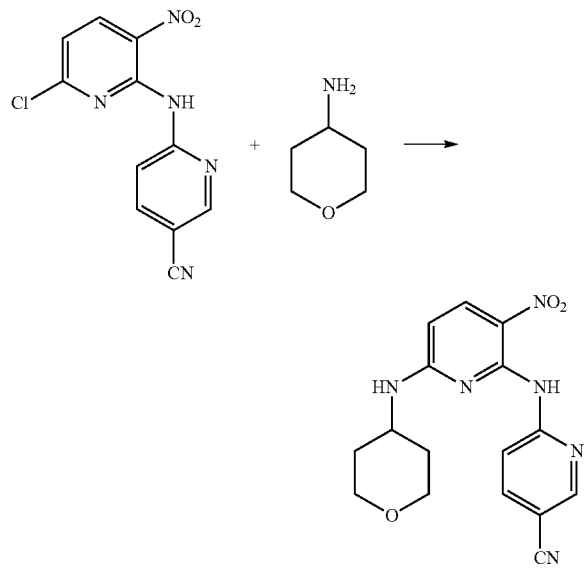

To 6-(6-chloro-3-nitro-pyridin-2-ylamino)-nicotinonitrile (Int 1, 4 g, 14.51 mmol, 1 eq.) in DMSO (20 mL) is added tetrahydro-pyran-4-ylamine (1.65 mL, 15.96 mmol, 1.1 eq.) and DIPEA (5.05 mL, 29.02 mmol, 2 eq.), the reaction mixture is then microwaved at 130° C. for 20 min. The mixture is diluted with H$_2$O and Et$_2$O, the precipitate is filtered off and air dried under vacuum to give the desired compound.

$^1$H NMR (300 MHz, DMSO-d$_6$) δ 11.38 (1H, s), 8.78 (1H, d), 8.47-8.63 (2H, m), 8.39 (1H, dd), 8.17 (1H, d), 6.27 (1H, d), 3.98-4.12 (1H, m), 3.91 (2H, d), 3.52 (2H, t), 1.94 (2H, d), 1.33-1.67 (2H, m).

1.2.3. General Method C

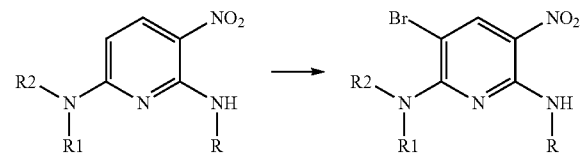

NBS (1.1 to 2 eq.) is added to a solution of 3-nitro-pyridine-2,6-diamino derivative (1 eq.) in dry MeCN, the reaction is stirred at r.t. and monitored by UPLC-MS. If full completion is not reached, additional NBS is added until no starting material is left. The precipitate formed is filtered off, washed with Et$_2$O and air dried under vacuum to provide the desired compound.

Illustrative Synthesis of General Method C

6-[5-bromo-3-nitro-6-(tetrahydro-pyran-4-ylamino)-pyridin-2-ylamino]-nicotinonitrile (Int 11)

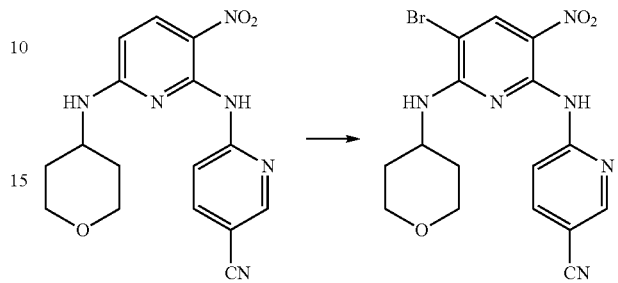

NBS (2.04 g, 11.46 mmol, 1.3 eq.) is added to a solution of 6-[3-nitro-6-(tetrahydro-pyran-4-ylamino)-pyridin-2-ylamino]-nicotinonitrile (Int 8, 3 g, 8.81 mmol, 1 eq.) in dry MeCN (150 mL) and the reaction is stirred at r.t. for 4 h. NBS (0.31 g, 1.76 mmol, 0.2 eq.) is added and the reaction is stirred at r.t. for another 16 h. The precipitate formed is filtered off, washed with Et$_2$O and air dried under vacuum to provide the desired compound.

$^1$H NMR (300 MHz, DMSO-d$_6$) δ 11.10 (1H, br s), 8.80 (1H, m), 8.34-8.50 (3H, m), 7.72 (1H, d), 4.05-4.25 (1H, m), 3.93 (2H, m), 3.38-3.55 (2H, m), 1.70-1.87 (4H, m).

1.2.4. General Method D

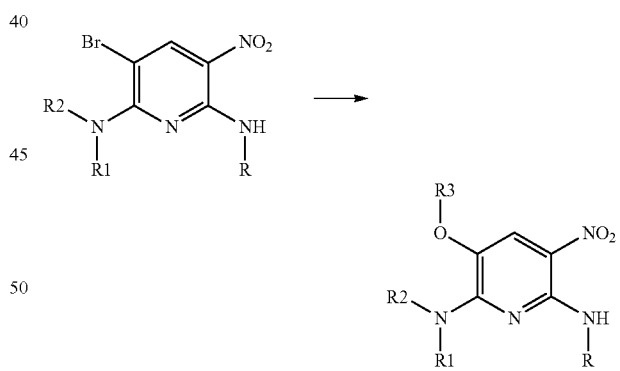

LiOtBu (3 eq.) is added portionwise to a solution of the corresponding alcohol (5 eq.) in dry 1,4-dioxane, or in the corresponding alcohol used as the solvent. 2-amino-3-bromo pyridine derivative (1 eq.) is then added followed by CuI (0.6 eq.). The reaction is heated to 80-120° C., or at 110-150° C. under microwaves irradiation, until completion of the reaction. The mixture is poured into icy water or a 1 N aqueous solution of HCl is added. The precipitate is filtered off and air dried under vacuum. The residue is then purified by flash chromatography on silica gel to obtain the desired compound.

Illustrative Synthesis of General Method D

6-[5-[2-(2-hydroxy-ethoxy)-ethoxy]-3-nitro-6-(tetrahydro-pyran-4-ylamino)-pyridin-2-ylamino]-nicotinonitrile (Int 19)

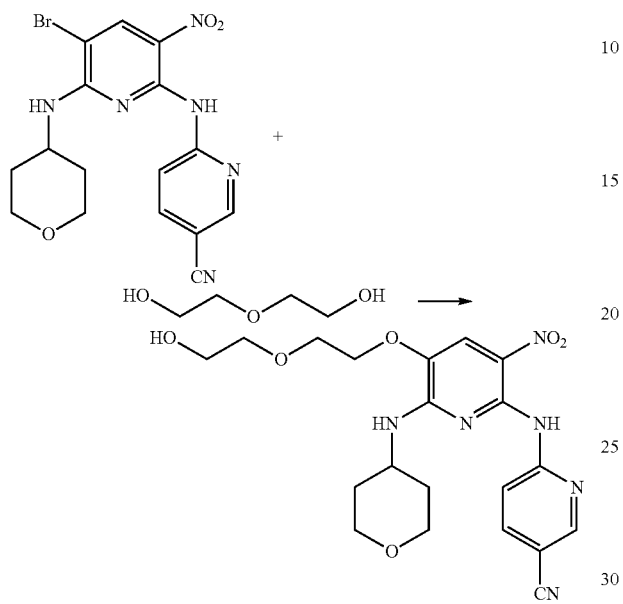

LiOtBu (2.87 g, 35.8 mmol, 3 eq.) is added portionwise to a solution of 2-(2-hydroxy-ethoxy)-ethanol (5.7 mL, 59.7 mmol, 5 eq.) in dry 1,4-dioxane (50 mL). 6-[5-bromo-3-nitro-6-(tetrahydro-pyran-4-ylamino)-pyridin-2-ylamino]-nicotinonitrile (Int 11, 5.0 g, 11.9 mmol, 1 eq.) is added followed by CuI (1.36 g, 7.2 mmol, 0.6 eq.). The reaction is then heated to 120° C. for 4 h. The mixture is cooled to 0° C., a 1 N aqueous solution of HCl (50 mL) is added and the resulting mixture is stirred at r.t. for 20 min. The precipitate is filtered and dried under vacuum. The residue is then purified by flash chromatography on silica gel, eluting from 0 to 5% of MeOH in DCM to give the desired compound.
MW (calcd): 444.45; MW (obsd): 445.18 ES+.
$^1$H NMR (400 MHz, DMSO-$d_6$) δ 11.42 (1H, s), 8.75-8.79 (1H, m), 8.47-8.50 (1H, m), 8.38 (1H, dd), 7.87 (1H, d), 7.69 (1H, s), 4.58-4.72 (1H, m), 4.21-4.26 (2H, m), 4.11-4.21 (1H, m), 3.94 (2H, dd), 3.82 (2H, dd), 3.44-3.57 (6H, m), 1.81-1.90 (2H, m), 1.74 (2H, qd).

1.2.5. General Method E

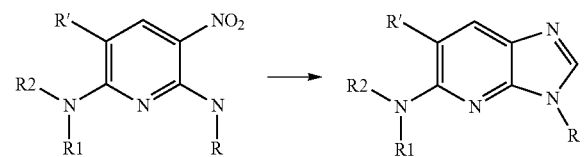

To a solution of 2,6-diamino-5-nitro-pyridin derivative (1 eq.) in dry MeOH are added trimethylorthoformate (roughly 0.1 mL for 0.1 mmol of 2,6-diamino-5-nitro-pyridin derivative) and formic acid (roughly 0.1 mL for 0.1 mmol of 2,6-diamino-5-nitro-pyridin derivative). NH$_4$Cl (4 eq.) and Zn (4 to 5 eq.) are then added and the mixture is heated to 70° C. until completion of the reaction. The reaction mixture is then cooled to r.t.

If upon cooling precipitation is observed, the solid is filtered and submitted to aqueous work-up with DCM/CHCl$_3$ and a 2% formic acid aqueous solution to afford the desired compound.

If upon cooling no precipitation occurs, solvents are evaporated and the residue is then purified by flash chromatography on silica gel to obtain the desired compound.

Illustrative Synthesis of General Method E

6-[6-[2-(2-hydroxy-ethoxy)-ethoxy]-5-(tetrahydro-pyran-4-ylamino)-imidazo[4,5-b]pyridin-3-yl]-nicotinonitrile (Compound 1)

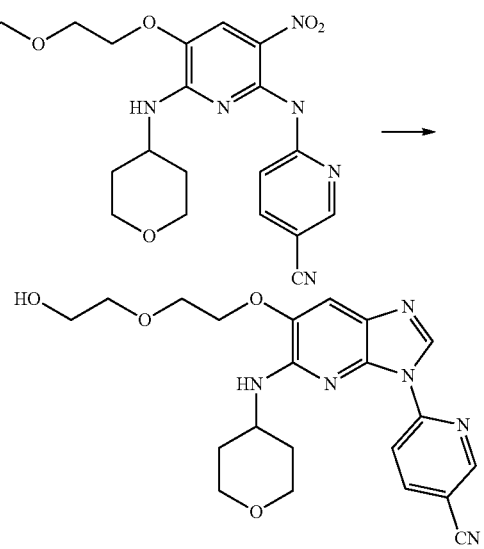

To a solution of 6-[5-[2-(2-hydroxy-ethoxy)-ethoxy]-3-nitro-6-(tetrahydro-pyran-4-ylamino)-pyridin-2-ylamino]-nicotinonitrile (Int 19, 2.3 g, 5.2 mmol, 1 eq.) in dry MeOH (60 mL) is added trimethylorthoformate (10 mL) and formic acid (10 mL). NH$_4$Cl (1.1 g, 20.7 mmol, 4 eq.) and Zn (1.4 g, 20.7 mmol, 4 eq.) are then added and the mixture is heated to reflux for 2 h. MeOH (30 mL) is added and the reaction mixture is heated to reflux for 1 h.

The mixture is cooled to r.t., the precipitate formed is filtered and dried under vacuum. MeOH (100 mL) and formic acid (2 mL) are added and the resulting mixture is stirred under reflux for 1 h. The mixture is cooled to r.t., poured into icy water and the precipitate formed is filtered and dried under vacuum. The solid is suspended in a mixture of DCM and CHCl$_3$, filtered through celite and the filtrate is washed with a 2% formic acid aqueous solution. The organic phase is dried over Na$_2$SO$_4$, filtered and concentrated to dryness to afford the desired compound.
MW (calcd): 424.46; MW (obsd): 425.40 ES+
$^1$H NMR (400 MHz, DMSO-$d_6$) δ 9.00 (1H, dd), 8.89-8.95 (1H, m), 8.75 (1H, s), 8.62 (1H, dd), 7.59 (1H, s), 6.04 (1H, d), 4.61-4.69 (1H, m), 4.22 (2H, dd), 4.05-4.17 (1H, m), 3.90-3.98 (2H, m), 3.83 (2H, dd), 3.50-3.60 (6H, m), 1.99 (2H, m), 1.55-1.70 (2H, m).

1.2.6. General Method F

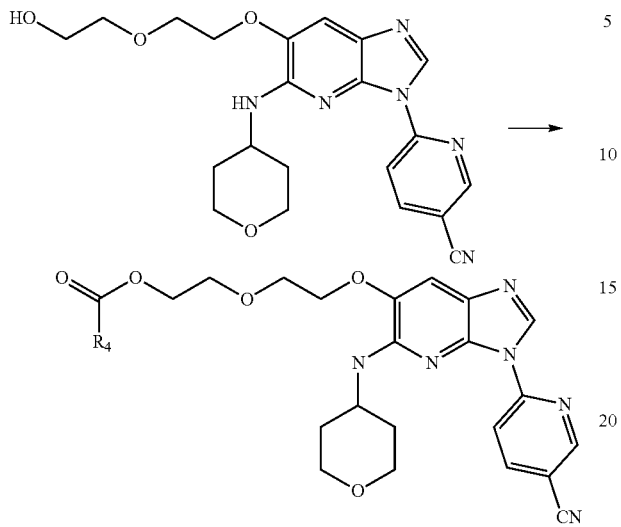

A mixture of Compound 1, corresponding carboxylic acid (1.5 eq.), DMAP (1.5 eq.) and EDCI (2.25 eq.) are stirred in DCM at r.t. until completion of the reaction. The reaction is quenched with H₂O, extracted with DCM, and then the organic layer is dried over MgSO₄ and evaporated to dryness. The residue is purified by flash chromatography on silica gel to obtain the desired compound.

Illustrative Synthesis of General Method F (S)-2-tert-butoxycarbonylamino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester (Int 30)

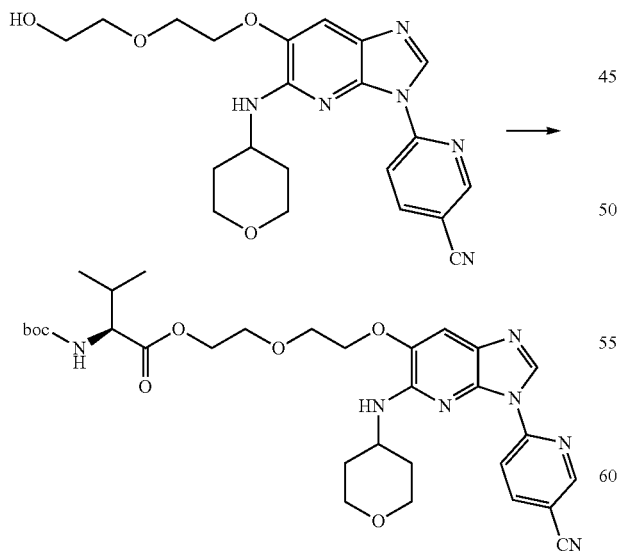

A mixture of Compound 1 (42 mg, 0.1 mmol, 1 eq.), boc-(S)-valine (33 mg, 0.15 mmol, 1.5 eq.), DMAP (19 mg, 0.15 mmol, 1.5 eq.), and EDCI (45 mg, 0.225 mmol, 2.25 eq.) is stirred in DCM (5 mL) at r.t. for 3 h. The reaction is quenched with H₂O, extracted with DCM, then the organic layer is dried over MgSO₄ and evaporated to dryness. The residue is purified by flash chromatography on silica gel, eluting from 0 to 100% of EtOAc in heptanes to give the desired compound.

1.2.7. General Method G: Salification Method

The starting material is dissolved in hot EtOAc or in a hot mixture of EtOAc and MeOH (5/1). Oxalic acid (0.2 M in EtOAc, 1 eq.) is added to the hot solution. A precipitate forms, which is filtered, rinsed with Et₂O and dried to afford the desired compound as the oxalic acid salt of the starting material.

Illustrative Synthesis of General Method G (S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl Ester Oxalic Acid Salt (Compound 10)

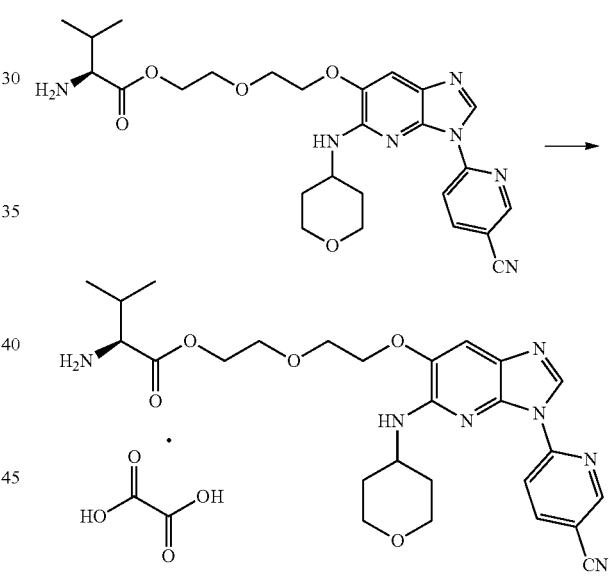

Compound 9 (100 mg, 0.19 mmol, 1 eq.) is dissolved in hot EtOAc (10 mL) and oxalic acid (0.2 M in EtOAc, 0.96 mL, 0.19 mmol, 1 eq.) is added to the hot solution. The formed precipitate is filtered, rinsed with Et₂O and dried to afford the desired compound.

1.2.8. Synthesis of (3,4 cis)-3-Amino-tetrahydro-pyran-4-ol (Int 28)

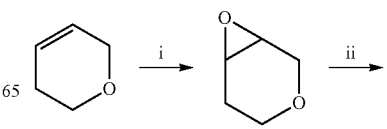

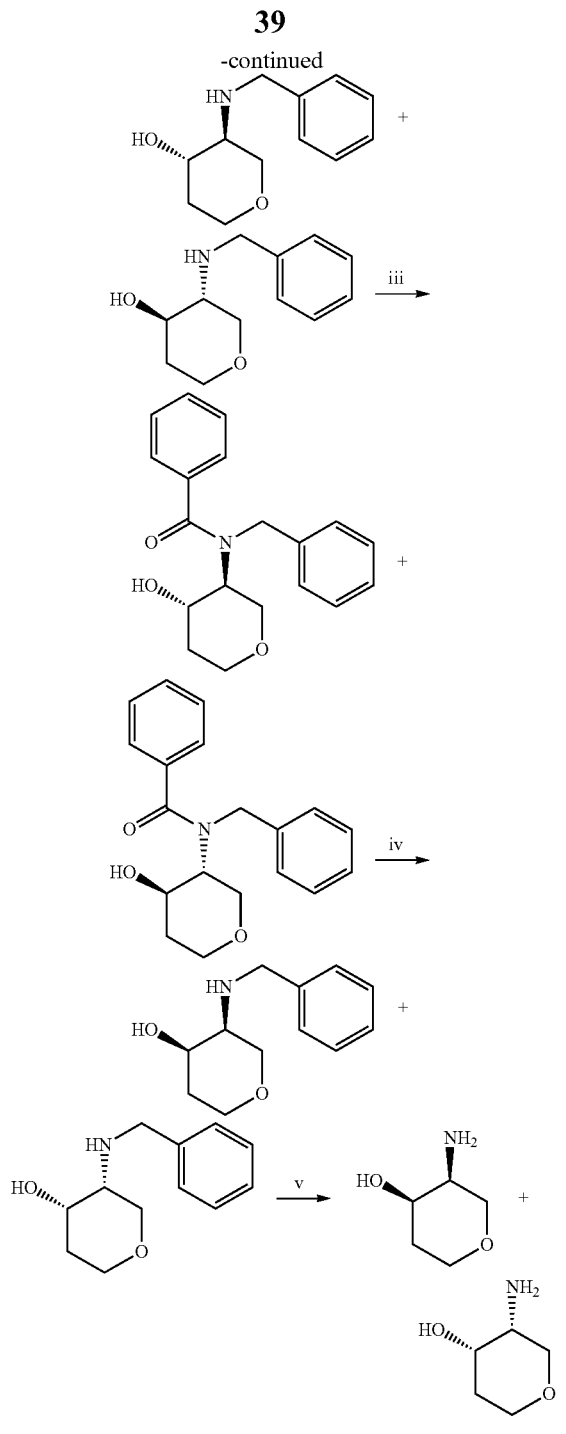

Step ii): (3,4 trans)-3-Benzylamino-tetrahydro-pyran-4-ol

A mixture of 3,7-dioxa-bicyclo[4.1.0]heptane (2.7 mmol, 1 eq.) and benzylamine (300 μL, 2.7 mmol, 1 eq.) in EtOH (10 mL) is heated at reflux temperature for 18 h. EtOH is then evaporated and the crude is purified by column chromatography on silica gel, eluting with DCM:MeOH:NH₄OH 10:1:0.1, to give the desired compound.

Step iii): N-Benzyl-N-((3,4 trans)-4-hydroxy-tetrahydro-pyran-3-yl)-benzamide Benzoyl chloride (78 μL, 0.68 mmol, 1 eq.) is added dropwise to an ice-cooled solution of (3,4 anti)-3-benzylamino-tetrahydro-pyran-4-ol from previous step (140 mg, 0.68 mmol, 1 eq.) and TEA (280 μL, 2.03 mmol, 3 eq.) in DCM (2 mL). The reaction mixture is stirred at r.t. for 1 h. The mixture is then washed twice with a 2 N aqueous HCl solution. The aqueous layers are extracted with DCM, and the combined organic layers are then dried over Na₂SO₄, filtered and concentrated in vacuo to afford the desired compound.

Step iv): (3,4 cis)-3-Benzylamino-tetrahydro-pyran-4-ol

A solution of N-benzyl-N-((3,4 trans)-4-hydroxy-tetrahydro-pyran-3-yl)-benzamide (220 mg, 0.71 mmol, 1 eq.) in DCM (2.5 mL) is added dropwise to thionyl chloride (195 μL, 2.68 mmol, 3.8 eq.) at 0° C. The reaction mixture is stirred at r.t. for 4 h, and then concentrated in vacuo. To the residue is added a 6 N aqueous HCl solution (2 mL), and the resulting mixture is heated at reflux temperature for 18 h. After cooling, a precipitate is filtered off, washed with water, and the filtrate is extracted with EtOAc. To the aqueous layer is added Et₂O and a 2 N NaOH aqueous solution is added to make the mixture alkaline. The phases are separated and the aqueous phase is extracted with DCM and EtOAc. The combined organic layers are then dried over Na₂SO₄, filtered and concentrated in vacuo to afford the desired compound.

Step v): (3,4 cis)-3-Amino-tetrahydro-pyran-4-ol

A solution of (3,4 cis)-3-benzylamino-tetrahydro-pyran-4-ol (100 mg, 0.48 mmol, 1 eq.) in MeOH (3 mL) is hydrogenated over 10% Pd/C (40 mg) for 1.5 h at r.t. under 1 atm of H₂. The catalyst is removed by filtration through celite, washed with MeOH and the filtrate is evaporated to give the desired compound.

1.2.9. Synthesis of (cis-1,4)-1-methyl-4-methylamino-cyclohexanol (Int 29)

Step i): 3,7-dioxa-bicyclo[4.1.0]heptane

To a solution of m-chloroperbenzoic acid (23.51 g, 136.2 mmol, 2 eq.) in DCM (15 mL) is added a solution of 3,6-dihydro-2H-pyran (5.73 g, 68.1 mmol, 1 eq.) in DCM (10 mL). The reaction mixture is allowed to stir at r.t. for 6 h, after which m-chloroperbenzoic acid (11.76 g, 68.1 mmol, 1 eq.) is added. The reaction mixture is stirred at r.t. for 16 h and filtered off. The filtrate is washed with saturated solutions of Na₂SO₃, NaHCO₃, and water. The organic layer is then dried over Na₂SO₄, filtered and concentrated in vacuo to afford the desired compound, used in the next step without further purification.

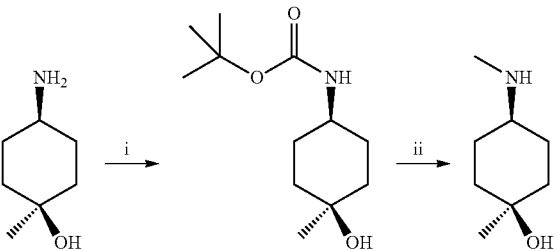

Step i): (cis-1,4)-(4-hydroxy-4-methyl-cyclohexyl)-carbamic Acid Tert-butyl Ester To a suspension of cis-4-amino-1-methylcyclohexanol (1.0 g, 7.74 mmol, 1 eq.) in MeCN (15 mL) is added di-tert-butyl dicarbonate (1.85 g, 8.47 mmol, 1.1 eq.) and the mixture is stirred at r.t. for 16 h. The precipitate is filtered, washed with hexane and dried to afford the desired compound.

Step ii): (cis-1,4)-1-methyl-4-methylamino-cyclohexanol

To a 2.0 M solution of LiAlH$_4$ in THF (7 mL, 14.0 mmol, 4.9 eq.) is added portionwise (cis-1,4)-(4-hydroxy-4-methyl-cyclohexyl)-carbamic acid tert-butyl ester (660 mg, 2.9 mmol, 1 eq.) at r.t. The reaction mixture is stirred at r.t. for 1 h and at reflux for 45 min. The reaction mixture is cooled to r.t., then water and THF are added. The precipitate is filtered off and washed with THF. The filtrate is concentrated to dryness, affording the desired compound.

1.2.10. Intermediate 34: 2-[2-[3-(5-cyano-2-pyridyl)-5-(tetrahydropyran-4-ylamino)imidazo[4,5-b]pyridin-6-yl]oxyethoxy]ethyl (2S)-2-[[2-(tert-butoxycarbonylamino)acetyl]amino]-3-methyl-butanoate

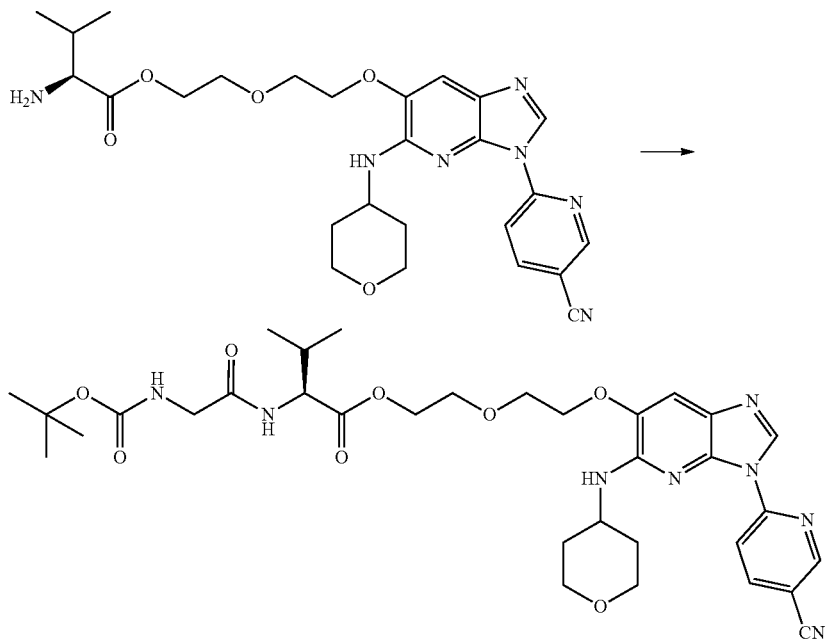

Compound 9 (170 mg, 0.40 mmol, 1 eq.), 2-(tert-butoxycarbonylamino)acetic acid (Boc-Gly-OH, 105 mg, 0.60 mmol, 1.5 eq.), EDCI (173 mg, 0.90 mmol, 2.25 eq.) and DMAP (73 mg, 0.6 mmol, 1.5 eq.) are mixed in DCM (4 mL) and stirred at r.t. overnight. The reaction is quenched with brine, extracted with DCM and the combined organic phases are evaporated to give the desired compound.

TABLE II

Intermediates used towards the compounds of the invention.

| Int # | Structures | Name | SM | Mtd | MW | MS Mes'd |
|---|---|---|---|---|---|---|
| 1 | 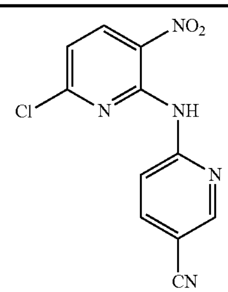 | 6-[(6-chloro-3-nitro-2-pyridyl)amino]pyridine-3-carbonitrile | 2,6-dichloro-3-nitropyridine | A | 275.7 | 276.3 |

TABLE II-continued

Intermediates used towards the compounds of the invention.

| Int # | Structures | Name | SM | Mtd | MW | MS Mes'd |
|---|---|---|---|---|---|---|
| 2 | 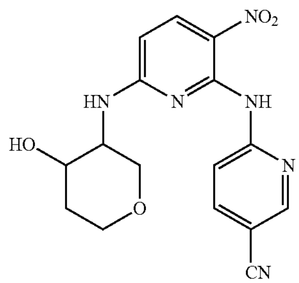 [SMILES: N#Cc1ccc(Nc2nc(NC3COCCC3O)ccc2[N+](=O)[O-])nc1] | 6-[[6-[[(cis-3,4)-4-hydroxytetrahydro-pyran-3-yl]amino]-3-nitro-2-pyridyl]amino]pyridine-3-carbonitrile | Int 1 + Int 28 | B | 356.3 | 357.4 |
| 3 | 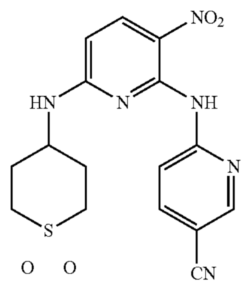 | 6-[[6-[(1,1-dioxothian-4-yl)amino]-3-nitro-2-pyridyl]amino]pyridine-3-carbonitrile | Int 1 | B | 388.4 | 389.2 |
| 4 | 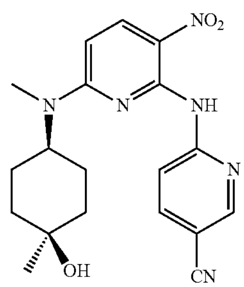 [SMILES: CN(c1ccc([N+](=O)[O-])c(Nc2ccc(C#N)cn2)n1)[C@H]1CC[C@@](C)(O)CC1] | 6-[[6-[((cis-1,4)-4-hydroxy-4-methyl-cyclohexyl)-methyl-amino]-3-nitro-2-pyridyl]amino]pyridine-3-carbonitrile | Int 1 + Int 29 | B | 382.4 | — |
| 5 | 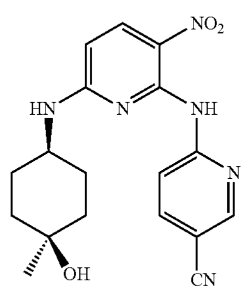 [SMILES: C[C@]1(O)CC[C@@H](Nc2ccc([N+](=O)[O-])c(Nc3ccc(C#N)cn3)n2)CC1] | 6-[[6-[((cis1,4)-4-hydroxy-4-methyl-cyclohexyl)amino]-3-nitro-2-pyridyl]amino]pyridine-3-carbonitrile | Int 1 | B | 368.4 | — |
| 6 | 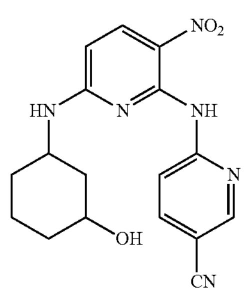 [SMILES: N#Cc1ccc(Nc2nc(NC3CCCC(O)C3)ccc2[N+](=O)[O-])nc1] | 6-[[6-[(3-hydroxycyclohexyl)amino]-3-nitro-2-pyridyl]amino]pyridine-3-carbonitrile | Int 1 | B | 354.4 | 355.4 |

TABLE II-continued

Intermediates used towards the compounds of the invention.

| Int # | Structures | Name | SM | Mtd | MW | MS Mes'd |
|---|---|---|---|---|---|---|
| 7 | 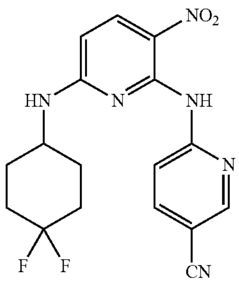 [SMILES: N#Cc1ccc(Nc2nc(NC3CCC(F)(F)CC3)ccc2[N+](=O)[O-])nc1] | 6-[[6-[(4,4-difluorocyclohexyl)amino]-3-nitro-2-pyridyl]amino]pyridine-3-carbonitrile | Int 1 | B | 374.4 | 375.4 |
| 8 | 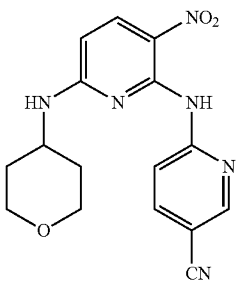 [SMILES: N#Cc1ccc(Nc2nc(NC3CCOCC3)ccc2[N+](=O)[O-])nc1] | 6-[[3-nitro-6-(tetrahydropyran-4-ylamino)-2-pyridyl]amino]pyridine-3-carbonitrile | Int 1 | B | 340.3 | 341.4 |
| 9 | 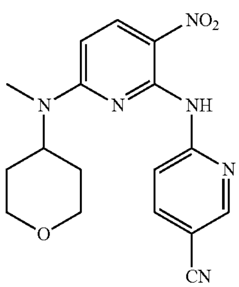 [SMILES: CN(c1ccc([N+](=O)[O-])c(Nc2ccc(C#N)cn2)n1)C1CCOCC1] | 6-[[6-[methyl(tetrahydropyran-4-yl)amino]-3-nitro-2-pyridyl]amino]pyridine-3-carbonitrile | Int 1 | B | 354.4 | — |
| 10 | 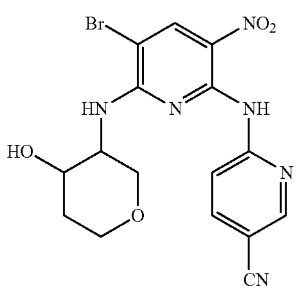 [SMILES: N#Cc1ccc(Nc2nc(NC3COCCC3O)c(Br)cc2[N+](=O)[O-])nc1] | 6-[[5-bromo-6-[[(cis-3,4)-4-hydroxytetrahydropyran-3-yl]amino]-3-nitro-2-pyridyl]amino]pyridine-3-carbonitrile | Int 2 | C | 435.2 | 435.4 437.3 |
| 11 | 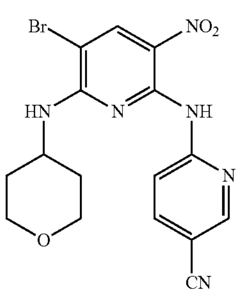 [SMILES: N#Cc1ccc(Nc2nc(NC3CCOCC3)c(Br)cc2[N+](=O)[O-])nc1] | 6-[[5-bromo-3-nitro-6-(tetrahydropyran-4-ylamino)-2-pyridyl]amino]pyridine-3-carbonitrile | Int 8 | C | 419.2 | 419.5 421.4 |

TABLE II-continued

Intermediates used towards the compounds of the invention.

| Int # | Structures | Name | SM | Mtd | MW | MS Mes'd |
|---|---|---|---|---|---|---|
| 12 | 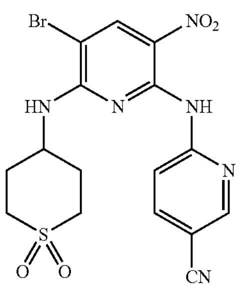 [SMILES: N#Cc1ccc(Nc2nc(NC3CCS(=O)(=O)CC3)c(Br)cc2[N+](=O)[O-])nc1] | 6-[[5-bromo-6-[(1,1-dioxothian-4-yl)amino]-3-nitro-2-pyridyl]amino]pyridine-3-carbonitrile | Int 3 | C | 467.3 | 467.2 469.3 |
| 13 | 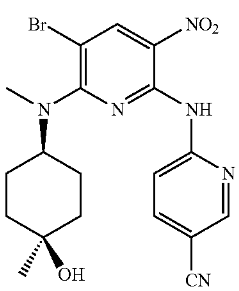 [SMILES: CN(c1nc(Nc2ccc(C#N)cn2)c([N+](=O)[O-])cc1Br)[C@H]1CC[C@@](C)(O)CC1] | 6-[[5-bromo-6-[(4-hydroxy-4-methyl-cyclohexyl)-methyl-amino]-3-nitro-2-pyridyl]amino]pyridine-3-carbonitrile | Int 4 | C | 461.3 | — |
| 14 | 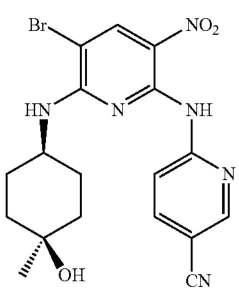 [SMILES: C[C@]1(O)CC[C@@H](Nc2nc(Nc3ccc(C#N)cn3)c([N+](=O)[O-])cc2Br)CC1] | 6-[[5-bromo-6-[((cis1,4)-4-hydroxy-4-methyl-cyclohexyl)amino]-3-nitro-2-pyridyl]amino]pyridine-3-carbonitrile | Int 5 | C | 447.3 | — |
| 15 | 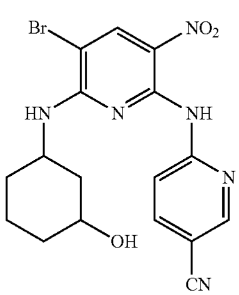 [SMILES: N#Cc1ccc(Nc2nc(NC3CCCC(O)C3)c(Br)cc2[N+](=O)[O-])nc1] | 6-[[5-bromo-6-[(3-hydroxycyclohexyl)amino]-3-nitro-2-pyridyl]amino]pyridine-3-carbonitrile | Int 6 | C | 433.3 | 433.4 435.4 |
| 16 | 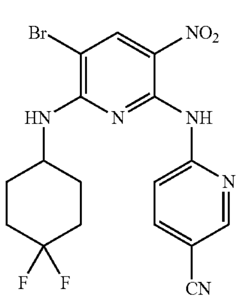 [SMILES: N#Cc1ccc(Nc2nc(NC3CCC(F)(F)CC3)c(Br)cc2[N+](=O)[O-])nc1] | 6-[[5-bromo-6-[(4,4-difluorocyclohexyl)amino]-3-nitro-2-pyridyl]amino]pyridine-3-carbonitrile | Int 7 | C | 453.3 | 453.3 455.3 |

TABLE II-continued

Intermediates used towards the compounds of the invention.

| Int # | Structures | Name | SM | Mtd | MW | MS Mes'd |
|---|---|---|---|---|---|---|
| 17 | 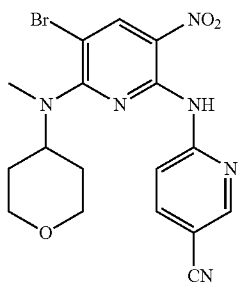 [SMILES: CN(c1nc(Nc2ccc(C#N)cn2)c([N+](=O)[O-])cc1Br)C1CCOCC1] | 6-[[5-bromo-6-[methyl(tetrahydropyran-4-yl)amino]-3-nitro-2-pyridyl]amino]pyridine-3-carbonitrile | Int 9 | C | 433.3 | 433.4 435.4 |
| 18 | 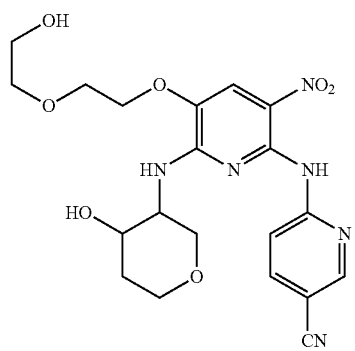 [SMILES: N#Cc1ccc(Nc2nc(NC3COCCC3O)c(OCCOCCO)cc2[N+](=O)[O-])nc1] | 6-[[5-[2-(2-hydroxyethoxy)ethoxy]-6-[[(cis-3,4)-4-hydroxytetrahydropyran-3-yl]amino]-3-nitro-2-pyridyl]amino]pyridine-3-carbonitrile | Int 10 | D | 460.5 | — |
| 19 | 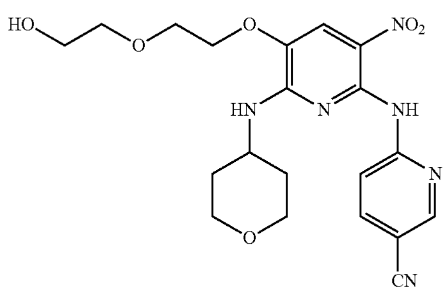 [SMILES: N#Cc1ccc(Nc2nc(NC3CCOCC3)c(OCCOCCO)cc2[N+](=O)[O-])nc1] | 6-[[5-[2-(2-hydroxyethoxy)ethoxy]-3-nitro-6-(tetrahydropyran-4-ylamino)-2-pyridyl]amino]pyridine-3-carbonitrile | Int 11 | D | 444.5 | 445.2 |
| 20 | 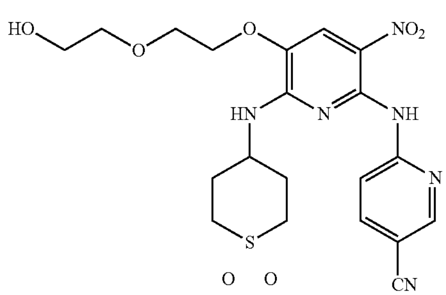 | 6-[[6-[(1,1-dioxothian-4-yl)amino]-5-[2-(2-hydroxyethoxy)ethoxy]-3-nitro-2-pyridyl]amino]pyridine-3-carbonitrile | Int 12 | D | 492.5 | 493.6 |
| 21 | 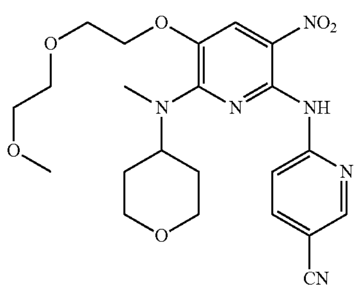 [SMILES: COCCOCCOc1cc([N+](=O)[O-])c(Nc2ccc(C#N)cn2)nc1N(C)C1CCOCC1] | 6-[[5-[2-(2-methoxyethoxy)ethoxy]-6-[methyl(tetrahydropyran-4-yl)amino]-3-nitro-2-pyridyl]amino]pyridine-3-carbonitrile | Int 17 | D | 472.5 | 473.6 |

TABLE II-continued

Intermediates used towards the compounds of the invention.

| Int # | Structures | Name | SM | Mtd | MW | MS Mes'd |
|---|---|---|---|---|---|---|
| 22 | 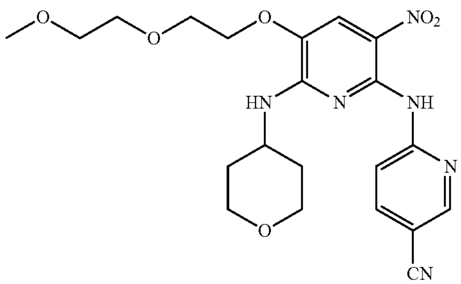 [SMILES: COCCOCCOc1cc([N+](=O)[O-])c(Nc2ccc(C#N)cn2)nc1NC1CCOCC1] | 6-[[5-[2-(2-methoxyethoxy)ethoxy]-3-nitro-6-(tetrahydropyran-4-ylamino)-2-pyridyl]amino]pyridine-3-carbonitrile | Int 11 | D | 458.5 | 459.5 |
| 23 | 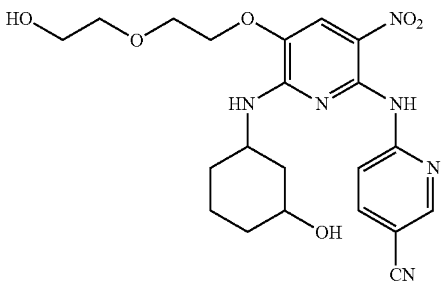 [SMILES: N#Cc1ccc(Nc2nc(NC3CCCC(O)C3)c(OCCOCCO)cc2[N+](=O)[O-])nc1] | 6-[[6-[(3-hydroxycyclohexyl)amino]-5-[2-(2-hydroxyethoxy)ethoxy]-3-nitro-2-pyridyl]amino]pyridine-3-carbonitrile | Int 15 | D | 458.5 | 459.5 |
| 24 | 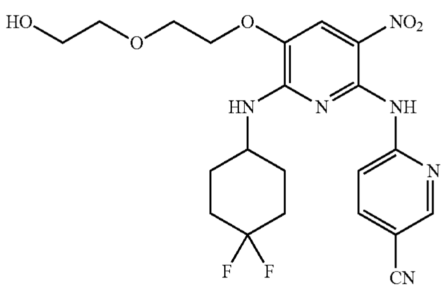 [SMILES: N#Cc1ccc(Nc2nc(NC3CCC(F)(F)CC3)c(OCCOCCO)cc2[N+](=O)[O-])nc1] | 6-[[6-[(4,4-difluorocyclohexyl)amino]-5-[2-(2-hydroxyethoxy)ethoxy]-3-nitro-2-pyridyl]amino]pyridine-3-carbonitrile | Int 16 | D | 478.5 | 479.5 |
| 25 | 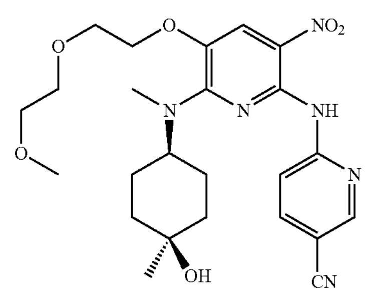 [SMILES: COCCOCCOc1cc([N+](=O)[O-])c(Nc2ccc(C#N)cn2)nc1N(C)[C@H]1CC[C@@](C)(O)CC1] | 6-[[6-[((cis1,4)-4-hydroxy-4-methyl-cyclohexyl)-methyl-amino]-5-[2-(2-methoxyethoxy)ethoxy]-3-nitro-2-pyridyl]amino]pyridine-3-carbonitrile | Int 13 | D | 500.6 | — |
| 26 | 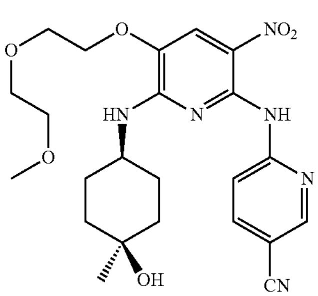 [SMILES: COCCOCCOc1cc([N+](=O)[O-])c(Nc2ccc(C#N)cn2)nc1N[C@H]1CC[C@@](C)(O)CC1] | 6-[[6-[((cis1,4)-4-hydroxy-4-methyl-cyclohexyl)amino]-5-[2-(2-methoxyethoxy)ethoxy]-3-nitro-2-pyridyl]amino]pyridine-3-carbonitrile | Int 14 | D | 486.5 | — |

TABLE II-continued

Intermediates used towards the compounds of the invention.

| Int # | Structures | Name | SM | Mtd | MW | MS Mes'd |
|---|---|---|---|---|---|---|
| 27 | 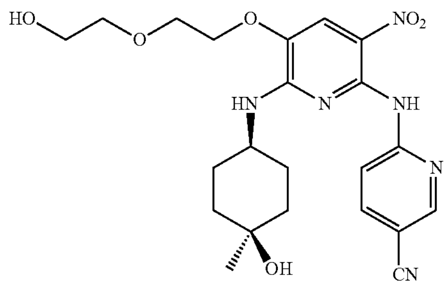 [SMILES: C[C@]1(O)CC[C@@H](Nc2nc(Nc3ccc(C#N)cn3)c([N+](=O)[O-])cc2OCCOCCO)CC1] | 6-[[5-[2-(2-hydroxyethoxy)ethoxy]-6-[((cis1,4)-4-hydroxy-4-methyl-cyclohexyl)amino]-3-nitro-2-pyridyl]amino]pyridine-3-carbonitrile | Int 14 | D | 472.5 | — |
| 28 | 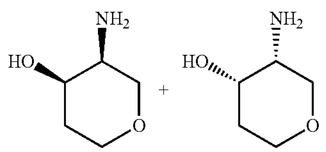 [SMILES: N[C@H]1COCC[C@H]1O ; N[C@@H]1COCC[C@@H]1O] | (3,4-cis)-3-Amino-tetrahydro-pyran-4-ol | 3,6-dihydro-2H-pyran | Example 1.2.8 | 117.2 | — |
| 29 | 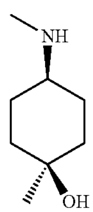 | (cis-1,4)-1-methyl-4-methylamino-cyclohexanol | cis-4-amino-1-methyl-cyclohexanol | Example 1.2.9 | 143.2 | — |
| 30 | 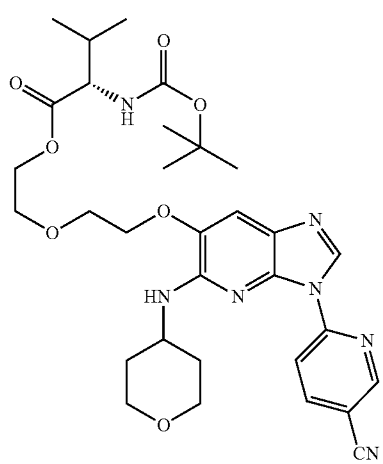 [SMILES: CC(C)[C@H](NC(=O)OC(C)(C)C)C(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl (2S)-2-(tert-butoxycarbonylamino)-3-methyl-butanoate | Cpd 1 | F | 623.7 | 624.9 |
| 31 | 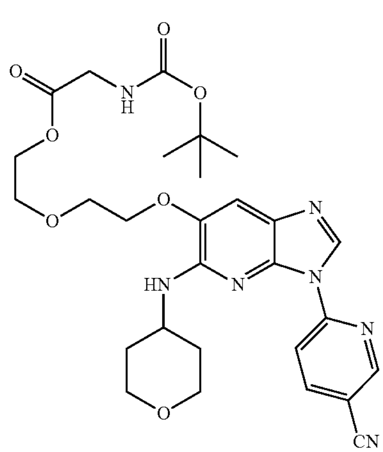 [SMILES: CC(C)(C)OC(=O)NCC(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl 2-(tert-butoxycarbonylamino)acetate | Cpd 1 | F | 581.6 | 582.7 |

TABLE II-continued

Intermediates used towards the compounds of the invention.

| Int # | Structures | Name | SM | Mtd | MW | MS Mes'd |
|---|---|---|---|---|---|---|
| 32 | 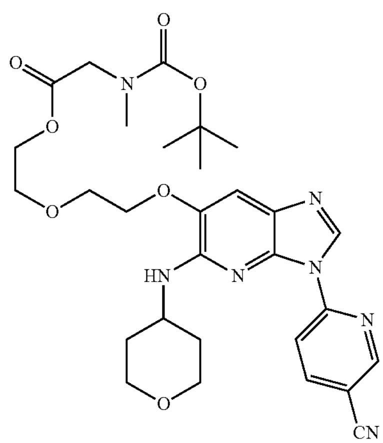 [SMILES: CN(CC(=O)OCCOCCOc1cc2ncn(-c3ccc(C#N)cn3)c2nc1NC1CCOCC1)C(=O)OC(C)(C)C] | 2-[2-[3-(5-cyano-2-pyridyl)-5-(tetrahydropyran-4-ylamino)imidazo[4,5-b]pyridin-6-yl]oxyethoxy]ethyl 2-[tert-butoxycarbonyl(methyl)amino]acetate | Cpd 1 | F | 595.7 | 596.7 |
| 33 | 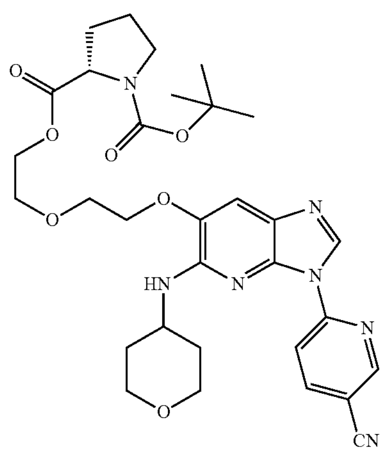 [SMILES: CC(C)(C)OC(=O)N1CCC[C@H]1C(=O)OCCOCCOc1cc2ncn(-c3ccc(C#N)cn3)c2nc1NC1CCOCC1] | O1-tert-butyl O2-[2-[2-[3-(5-cyano-2-pyridyl)-5-(tetrahydropyran-4-ylamino)imidazo[4,5-b]pyridin-6-yl]oxyethoxy]ethyl] (2S)-pyrrolidine-1,2-dicarboxylate | Cpd 1 | F | 621.6 | 622.8 |
| 34 | 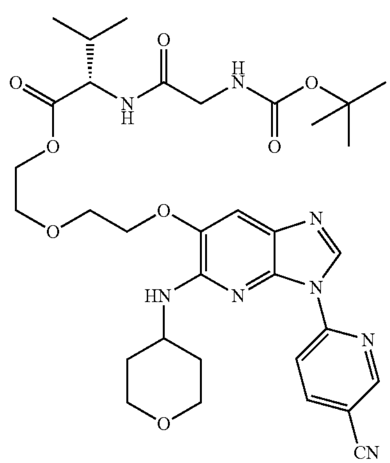 [SMILES: CC(C)[C@H](NC(=O)CNC(=O)OC(C)(C)C)C(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl (2S)-2-[[2-(tert-butoxycarbonylamino)acetyl]amino]-3-methyl-butanoate | Cpd 9 | Example 1.2.10 | 680.8 | 681.8 |

TABLE II-continued

Intermediates used towards the compounds of the invention.

| Int # | Structures | Name | SM | Mtd | MW | MS Mes'd |
|---|---|---|---|---|---|---|
| 35 | 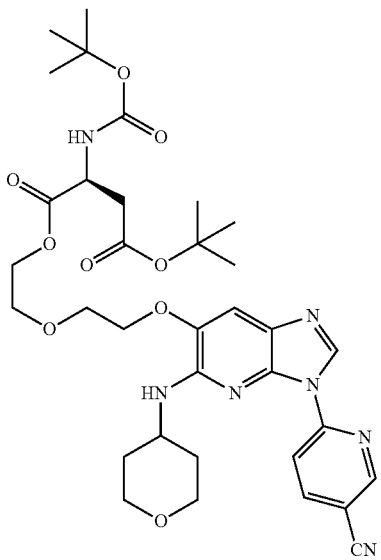 [SMILES: CC(C)(C)OC(=O)C[C@H](NC(=O)OC(C)(C)C)C(=O)OCCOCCOc1cc2ncn(-c3ccc(C#N)cn3)c2nc1NC1CCOCC1] | O4-tert-butyl O1-[2-[2-[3-(5-cyano-2-pyridyl)-5-(tetrahydropyran-4-ylamino)imidazo[4,5-b]pyridin-6-yl]oxyethoxy]ethyl] (2S)-2-(tert-butoxycarbonylamino)butanedioate | Cpd 1 | F | 695.8 | 696.9 |
| 36 | 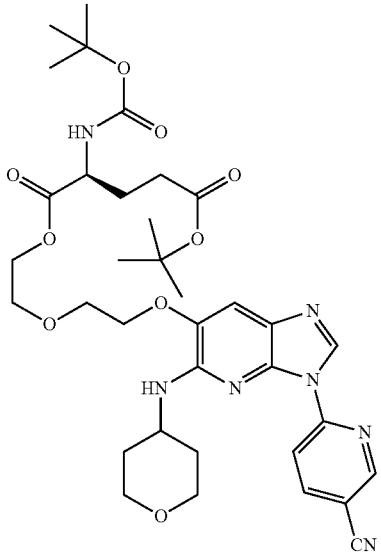 [SMILES: CC(C)(C)OC(=O)CC[C@H](NC(=O)OC(C)(C)C)C(=O)OCCOCCOc1cc2ncn(-c3ccc(C#N)cn3)c2nc1NC1CCOCC1] | O5-tert-butyl O1-[2-[2-[3-(5-cyano-2-pyridyl)-5-(tetrahydropyran-4-ylamino)imidazo[4,5-b]pyridin-6-yl]oxyethoxy]ethyl] (2S)-2-(tert-butoxycarbonylamino)pentanedioate | Cpd 1 | F | 709.8 | 710.8 |

TABLE II-continued

Intermediates used towards the compounds of the invention.

| Int # | Structures | Name | SM | Mtd | MW | MS Mes'd |
|---|---|---|---|---|---|---|
| 37 | (structure) | O4-tert-butyl O1-[2-[2-[3-(5-cyano-2-pyridyl)-5-(tetrahydropyran-4-ylamino)imidazo[4,5-b]pyridin-6-yl]oxyethoxy]ethyl] butanedioate | Cpd 1 | F | 580.6 | 581.7 |

SM = Starting Material,
Mtd = Method,
MS Mes'd = Mesured mass

Example 2. Preparation of the Compounds of the Invention

2.1. Compound 3: 6-{6-[2-(2-hydroxy-ethoxy)-ethoxy]-5-[((cis-1,4)-4-hydroxy-4-methyl-cyclohexyl)-methyl-amino]-imidazo[4,5-b]pyridin-3-yl}-nicotinonitrile

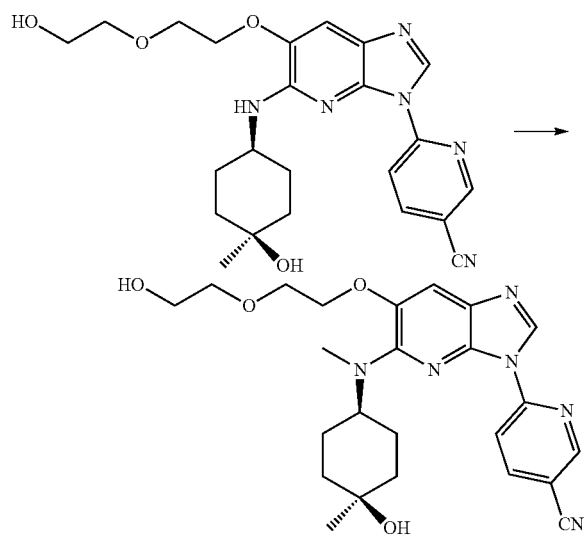

Formaldehyde (3.1 µL, 0.11 mmol, 1 eq.) is added to a solution of Compound 12 (50 mg, 0.11 mmol, 1 eq.) in a mixture of TFA/DCM (2 mL, 1/1). After stirring at r.t. for 30 min, NaBH(OAc)₃ (47 mg, 0.22 mmol, 2 eq.) is added and the reaction is stirred for 1 h at r.t. The reaction mixture is then evaporated to dryness and the crude product is purified by preparative HPLC-MS to obtain the desired compound.

2.2. Compound 8: Sulfuric Acid Mono-(2-{2-[3-(5-cyano-pyridin-2-yl)-5-(tetrahydro-pyran-4-ylamino)-3H-imidazo[4,5-b]pyridin-6-yloxy]-ethoxy}-ethyl) Ester

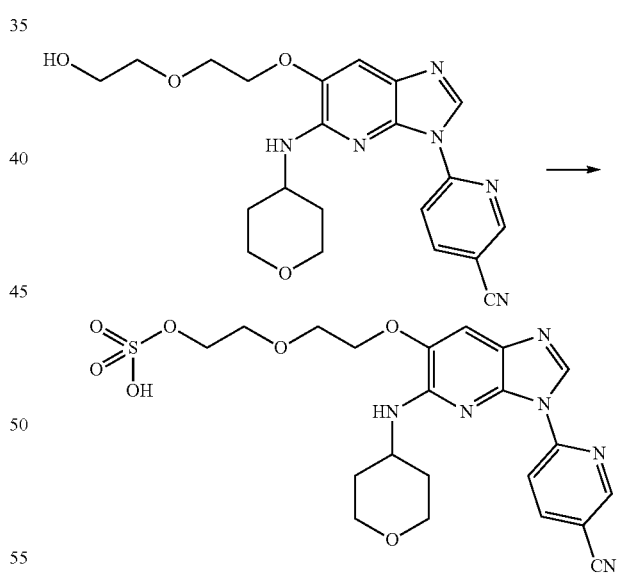

Compound 1 (84 mg, 0.2 mmol, 1 eq.) is added to a solution of pyridine-SO₃ complex (127 mg, 0.8 mmol, 4 eq.) in pyridine (5 mL) and the reaction is heated to reflux for 16 h. The mixture is then evaporated to dryness and purified by flash chromatography on silica gel, eluting from 100% EtOAc to 100% (DCM/MeOH/AcOH/H₂O: 90/10/1/1) then to 100% (DCM/MeOH/AcOH/H₂O: 85/15/2/2) to give the desired compound.

2.3. Compound 9: (S)-2-amino-3-methyl-butyric Acid 2-{2-[3-(5-cyano-pyridin-2-yl)-5-(tetrahydro-pyran-4-ylamino)-3H-imidazo[4,5-b]pyridin-6-yloxy]-ethoxy}-ethyl Ester

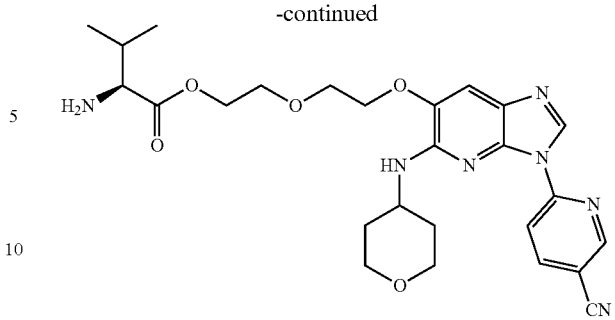

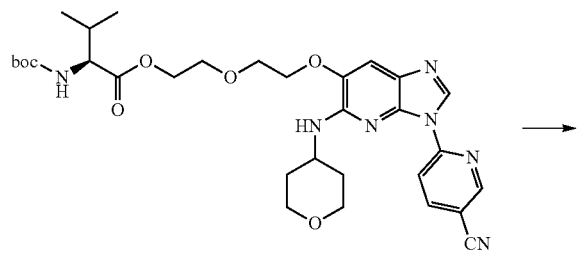

TFA (0.5 mL) is added to a solution of Int 30 (20 mg, 0.032 mmol, 1 eq.) in DCM (10 mL), and the mixture is stirred for 1 h at r.t. The reaction is quenched with a sat. aq. solution of NaHCO₃ and extracted with EtOAc. The organic layer is dried over MgSO₄ and evaporated to dryness. The residue is recrystallized from the solvent system DCM/Et₂O in pentane to provide the desired compound.

2.4. Compound 16: 2-[2-[3-(5-cyano-2-pyridyl)-5-(tetrahydropyran-4-ylamino)imidazo[4,5-b]pyridin-6-yl]oxyethoxy]ethyl 2-aminoacetate

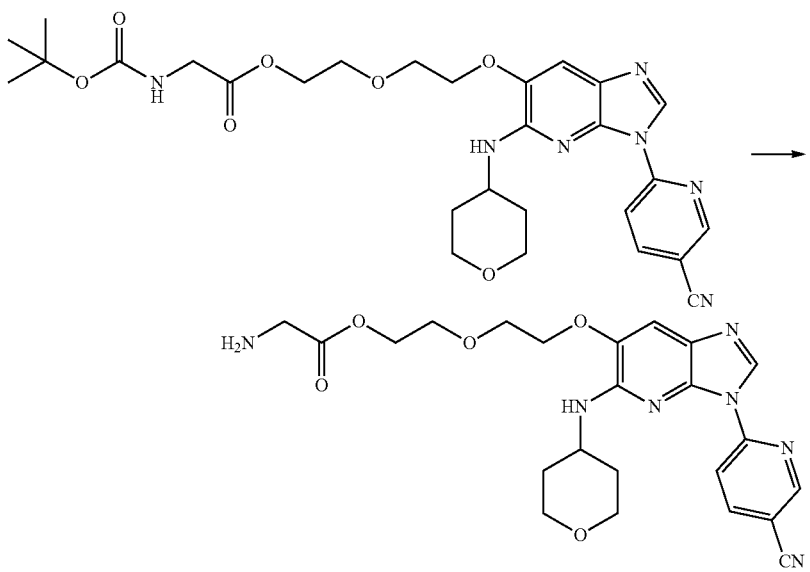

Int 31 (195 mg, 0.34 mmol, 1 eq.) is placed in a TFA/DCM mixture (1/5 mL) and the reaction is stirred at r.t. for 2 h. The reaction mixture is then diluted with toluene and evaporated to dryness. The residue is taken up in DCM, washed with a sat. aq. NaHCO₃ solution and the organic phase is evaporated to dryness. The residue is dissolved in the minimal amount of DCM, a large volume of Et₂O is added and the formed solid is allowed to settle at the bottom of the flask. Solvents are carefully removed, leaving the solid in the flask, pentane is added and the solid is filtered to give the desired compound.

2.5. Compound 17: 2-[2-[3-(5-cyano-2-pyridyl)-5-(tetrahydropyran-4-ylamino)imidazo[4,5-b]pyridin-6-yl]oxyethoxy]ethyl 2-(methylamino)acetate

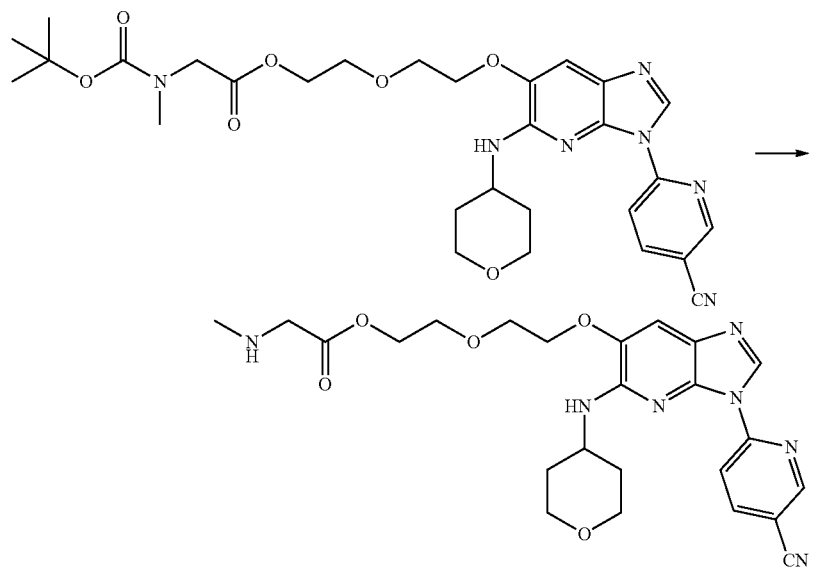

Int 32 (205 mg, 0.34 mmol, 1 eq.) is placed in a TFA/DCM mixture (1/5 mL) and the reaction is stirred at r.t. for 2 h. The reaction mixture is then diluted with toluene and evaporated to dryness. The residue is taken up in DCM, washed with a sat. aq. NaHCO$_3$ solution and the organic phase is evaporated to dryness. The residue is dissolved in the minimal amount of DCM, a large volume of Et$_2$O is added and the formed solid is allowed to settle at the bottom of the flask. Solvents are carefully removed, leaving the solid in the flask, pentane is added and the solid is filtered to give the desired compound.

2.6. Compound 18: 2-[2-[3-(5-cyano-2-pyridyl)-5-(tetrahydropyran-4-ylamino)imidazo[4,5-b]pyridin-6-yl]oxyethoxy]ethyl (2S)-pyrrolidine-2-carboxylate

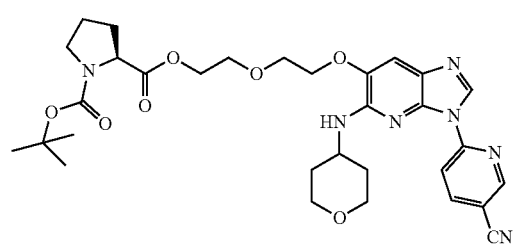

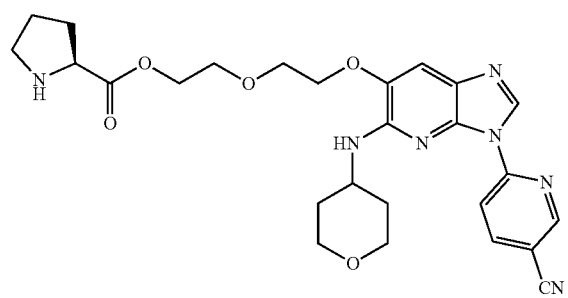

Int 33 (211 mg, 0.34 mmol, 1 eq.) is placed in a TFA/DCM mixture (1/5 mL) and the reaction is stirred at r.t. for 2 h. The reaction mixture is then diluted with toluene and evaporated to dryness. The residue is taken up in DCM, washed with a sat. aq. NaHCO$_3$ solution and the organic phase is evaporated to dryness. The residue is dissolved in the minimal amount of DCM, a large volume of Et$_2$O is added and the formed solid is allowed to settle at the bottom of the flask. Solvents are carefully removed, leaving the solid in the flask, pentane is added and the solid is filtered to give the desired compound.

2.7. Compound 19: 2-[2-[3-(5-cyano-2-pyridyl)-5-(tetrahydropyran-4-ylamino)imidazo[4,5-b]pyridin-6-yl]oxyethoxy]ethyl (2S)-2-[(2-aminoacetyl)amino]-3-methyl-butanoate

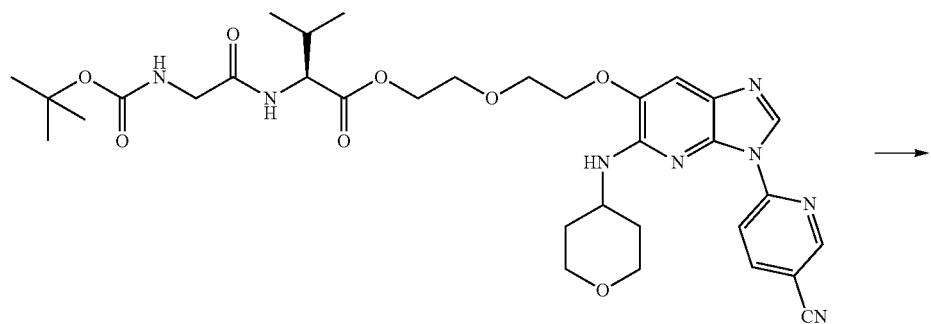

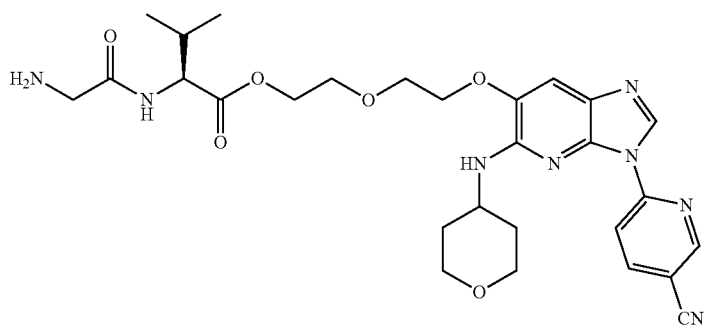

Int 34 (212 mg, 0.31 mmol, 1 eq.) is placed in a TFA/DCM mixture (1/5 mL) and the reaction is stirred at r.t. for 2 h. Toluene is then added and the solvents evaporated to dryness. The residue is dissolved in DCM and after addition of a sat. aq. NaHCO₃ solution a solid precipitates. It is filtered and dried to afford the desired compound.

2.8. Compound 27: (3S)-3-amino-4-[2-[2-[3-(5-cyano-2-pyridyl)-5-(tetrahydropyran-4-ylamino)imidazo[4,5-b]pyridin-6-yl]oxyethoxy]ethoxy]-4-oxo-butanoic Acid Hydrochloric Acid Salt

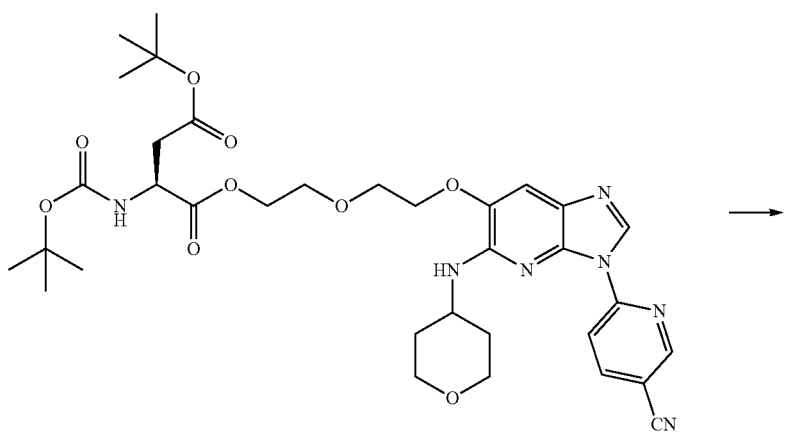

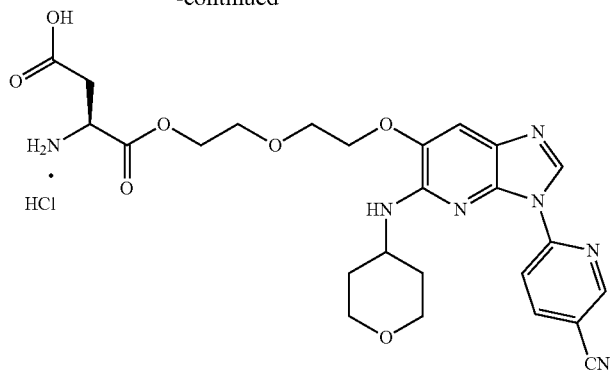

A solution of HCl in 1,4-dioxane (4 M, 0.4 mL, 1.6 mmol, 5 eq.) is added to Int 35 (222 mg, 0.32 mmol, 1 eq.) in 1,4-dioxane (4 mL). The mixture is stirred at r.t. for 3 h and then is evaporated to dryness. The residue is taken up in an HCl solution in 1,4-dioxane (4 M, 6 mL), the reaction is stirred at r.t. for 2 h and more HCl solution in 1,4-dioxane (4 M, 2 mL) is added. After 1 h stirring at r.t. the solvents are evaporated to dryness to give the desired compound.

2.9. Compound 28: 4S)-4-amino-5-[2-[2-[3-(5-cyano-2-pyridyl)-5-(tetrahydropyran-4-ylamino)imidazo[4,5-b]pyridin-6-yl]oxyethoxy]ethoxy]-5-oxo-pentanoic Acid Hydrochloric Acid Salt

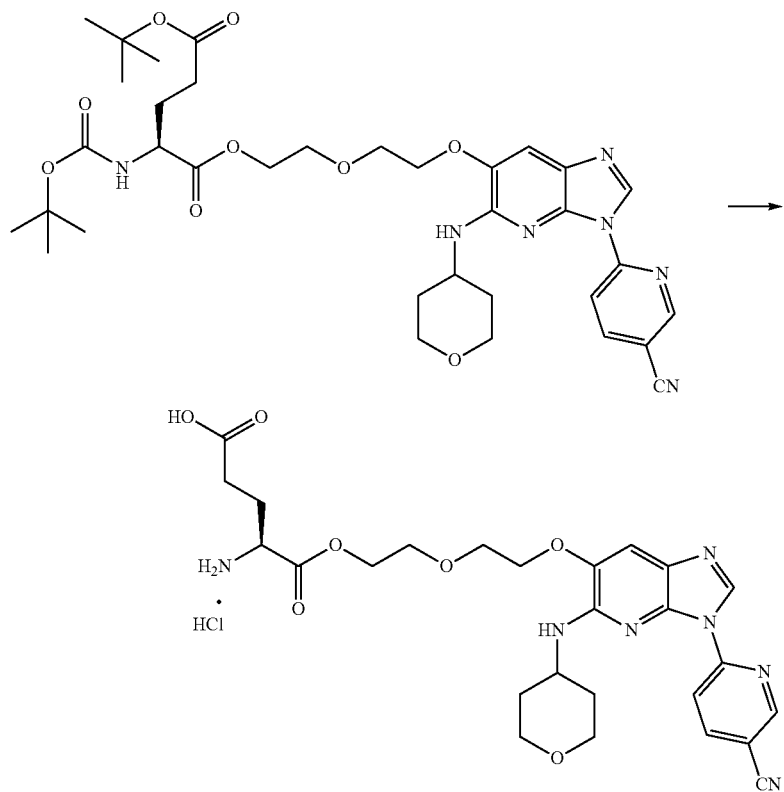

A solution of HCl in 1,4-dioxane (4 M, 0.41 mL, 1.63 mmol, 5 eq.) is added to Int 36 (232 mg, 0.33 mmol, 1 eq.) in 1,4-dioxane (4 mL). The mixture is stirred at r.t. for 3 h and then is evaporated to dryness. The residue is taken up in an HCl solution in 1,4-dioxane (4 M, 6 mL) and the reaction is stirred at rt for 2 h. The solvents are evaporated to dryness to give the desired compound.

2.10. Compound 33: 4-[2-[2-[3-(5-cyano-2-pyridyl)-5-(tetrahydropyran-4-ylamino)imidazo[4,5-b]pyridin-6-yl]oxyethoxy]ethoxy]-4-oxo-butanoic Acid

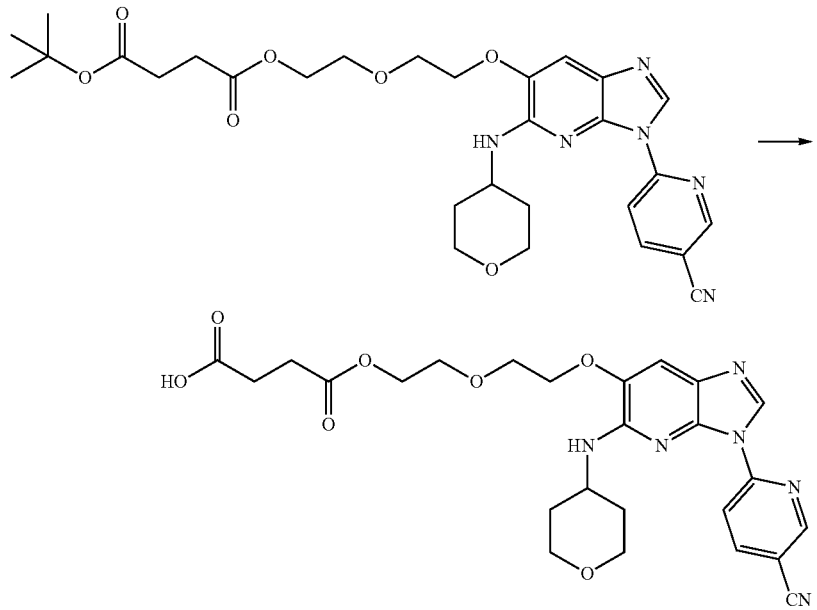

Int 37 (90 mg, 0.16 mmol, 1 eq.) is placed in a TFA/DCM mixture (1/5 mL) and the reaction is stirred at r.t. for 2 h. Toluene is then added and the solvents are evaporated to dryness. The residue is purified by flash chromatography on silica gel, eluting from 0 to 6% MeOH in DCM, and the obtained product is precipitated from MeOH to afford after filtration the desired compound.

TABLE III

Illustrative compounds of the invention.

| Cpd # | Structure | Name | SM | Method | MW | MS Mes'd |
|---|---|---|---|---|---|---|
| 1 | 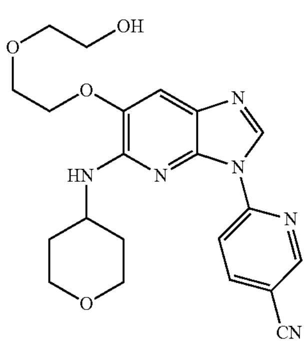 [SMILES: N#Cc1ccc(-n2cnc3cc(OCCOCCO)c(NC4CCOCC4)nc32)nc1] | 6-[6-[2-(2-hydroxy-ethoxy)-ethoxy]-5-(tetrahydro-pyran-4-ylamino)-imidazo[4,5-b]pyridin-3-yl]-nicotinonitrile | Int 19 | E | 424.5 | ES+ 425.4 |

TABLE III-continued

Illustrative compounds of the invention.

| Cpd # | Structure | Name | SM | Method | MW | MS Mes'd |
|---|---|---|---|---|---|---|
| 2 | 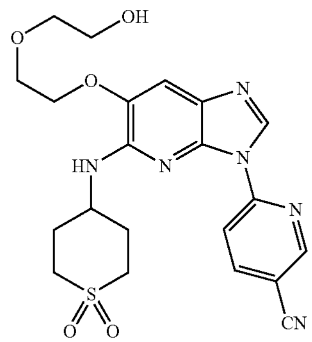 [SMILES: N#Cc1ccc(-n2cnc3cc(OCCOCCO)c(NC4CCS(=O)(=O)CC4)nc32)nc1] | 6-{5-(1,1-dioxo-tetrahydro-2H-thiopyran-4-ylamino)-6-[2-(2-hydroxy-ethoxy)-ethoxy]-imidazo[4,5-b]pyridin-3-yl}-nicotinonitrile | Int 20 | E | 472.5 | ES+ 473.6 ES– 471.5 |
| 3 | 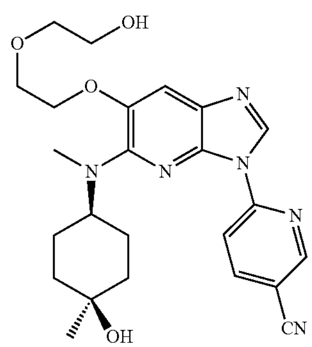 [SMILES: CN(c1nc2c(cc1OCCOCCO)ncn2-c1ccc(C#N)cn1)[C@H]1CC[C@@](C)(O)CC1] | 6-{6-[2-[2-hydroxy-ethoxy)-ethoxy]-5-[((cis-1,4)-4-hydroxy-4-methyl-cyclohexyl)-methyl-amino]-imidazo[4,5-b]pyridin-3-yl}-nicotinonitrile | Cpd 12 | Example 2.1 | 466.5 | ES+ 467.6 |
| 4 | 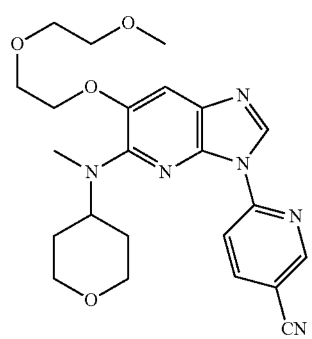 [SMILES: COCCOCCOc1cc2ncn(-c3ccc(C#N)cn3)c2nc1N(C)C1CCOCC1] | 6-{6-[2-(2-methoxy-ethoxy)-ethoxy]-5-[methyl-(tetrahydro-pyran-4-yl)-amino]-imidazo[4,5-b]pyridin-3-yl}-nicotinonitrile | Int 21 | E | 452.5 | 453.6 |
| 5 | 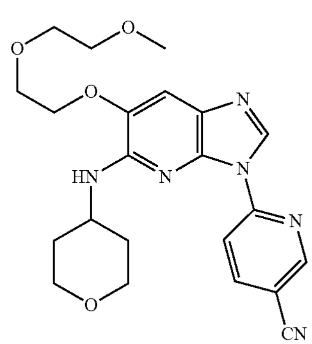 [SMILES: COCCOCCOc1cc2ncn(-c3ccc(C#N)cn3)c2nc1NC1CCOCC1] | 6-[6-[2-(2-methoxy-ethoxy)-ethoxy]-5-(tetrahydro-pyran-4-ylamino)-imidazo[4,5-b]pyridin-3-yl]-nicotinonitrile | Int 22 | E | 438.5 | ES+ 439.5 ES– 437.5 |

TABLE III-continued

Illustrative compounds of the invention.

| Cpd # | Structure | Name | SM | Method | MW | MS Mes'd |
|---|---|---|---|---|---|---|
| 6 | 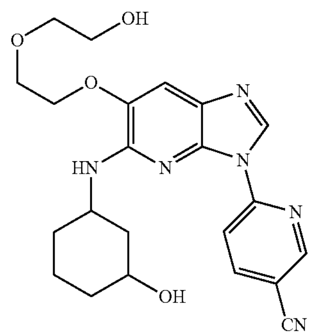 [SMILES: N#Cc1ccc(-n2cnc3cc(OCCOCCO)c(NC4CCCC(O)C4)nc32)nc1] | 6-{5-(3-hydroxy-cyclohexylamino)-6-[2-(2-hydroxy-ethoxy)-ethoxy]-imidazo[4,5-b]pyridin-3-yl}-nicotinonitrile | Int 23 | E | 438.5 | ES+ 439.49 |
| 7 | 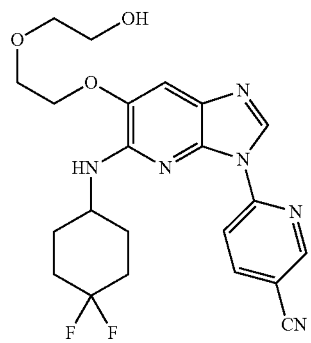 [SMILES: N#Cc1ccc(-n2cnc3cc(OCCOCCO)c(NC4CCC(F)(F)CC4)nc32)nc1] | 6-{5-(4,4-difluoro-cyclohexylamino)-6-[2-(2-hydroxy-ethoxy)-ethoxy]-imidazo[4,5-b]pyridin-3-yl}-nicotinonitrile | Int 24 | E | 458.5 | ES+ 459.5 ES− 457.4 |
| 8 | 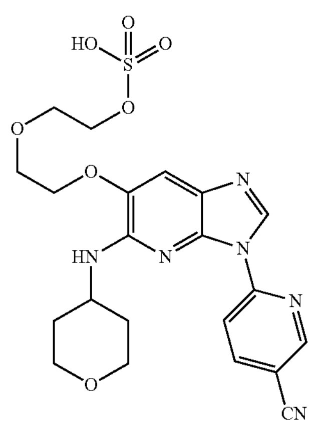 [SMILES: N#Cc1ccc(-n2cnc3cc(OCCOCCOS(=O)(=O)O)c(NC4CCOCC4)nc32)nc1] | sulfuric acid mono-(2-{2-[3-(5-cyano-pyridin-2-yl)-5-(tetrahydro-pyran-4-ylamino)-3H-imidazo[4,5-b]pyridin-6-yloxy]-ethoxy}-ethyl) ester | Cpd 1 | Example 2.2 | 504.5 | ES+ 505.4 ES− 503.4 |
| 9 | 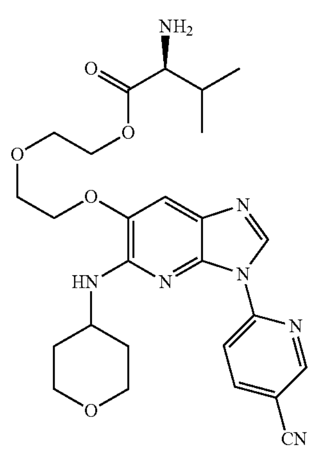 [SMILES: CC(C)[C@H](N)C(=O)OCCOCCOc1cc2ncn(-c3ccc(C#N)cn3)c2nc1NC1CCOCC1] | (S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester | Int 30 | Example 2.3 | 523.6 | ES+ 524.6 ES− 522.6 |

TABLE III-continued

Illustrative compounds of the invention.

| Cpd # | Structure | Name | SM | Method | MW | MS Mes'd |
|---|---|---|---|---|---|---|
| 10 | 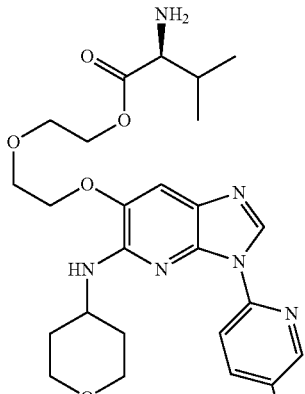 | (S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester oxalic acid salt | Cpd 9 | G | 613.6 | 524.4 |
| 11 | 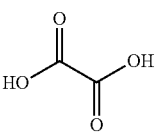 | 6-[6-[2-(2-hydroxyethoxy)eth-oxy]-5-[[(cis-3,4)-4-hydroxytetrahydropyran-3-yl]amino]imidazo[4,5-b]pyridin-3-yl]pyridine-3-carbonitrile | Int 18 | E | 440.5 | 441.3 |
| 12 | 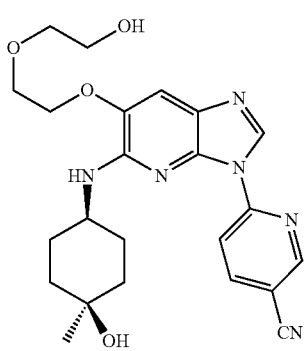 [SMILES: C[C@]1(O)CC[C@@H](Nc2nc3c(cc2OCCOCCO)ncn3-c2ccc(C#N)cn2)CC1] | 6-[6-[2-(2-hydroxyethoxy)eth-oxy]-5-[[(cis-1,4)-4-hydroxy-4-methylcyclohexyl)amino]imidazo[4,5-b]pyridin-3-yl]pyridine-3-carbonitrile | Int 27 | E | 452.5 | 453.0 |

TABLE III-continued

Illustrative compounds of the invention.

| Cpd # | Structure | Name | SM | Method | MW | MS Mes'd |
|---|---|---|---|---|---|---|
| 13 | 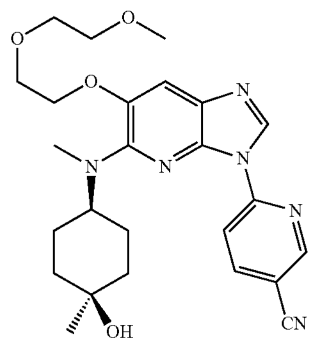 [SMILES: COCCOCCOc1cc2ncn(-c3ccc(C#N)cn3)c2nc1N(C)[C@H]1CC[C@@](C)(O)CC1] | 6-[5-[((cis-1,4)-4-hydroxy-4-methyl-cyclohexyl)-methyl-amino]-6-[2-(2-methoxyethoxy)eth-oxy]imidazo[4,5-b]pyridin-3-yl]pyridine-3-carbonitrile | Int 25 | E | 480.6 | 481.4 |
| 14 | 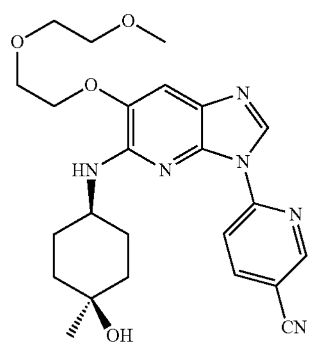 [SMILES: COCCOCCOc1cc2ncn(-c3ccc(C#N)cn3)c2nc1N[C@H]1CC[C@@](C)(O)CC1] | 6-[5-[((cis-1,4)-4-hydroxy-4-methylcyclohexyl)amino]-6-[2-(2-methoxyethoxy)eth-oxy]imidazo[4,5-b]pyridin-3-yl]pyridine-3-carbonitrile | Int 26 | E | 466.5 | 467.3 |
| 15 | 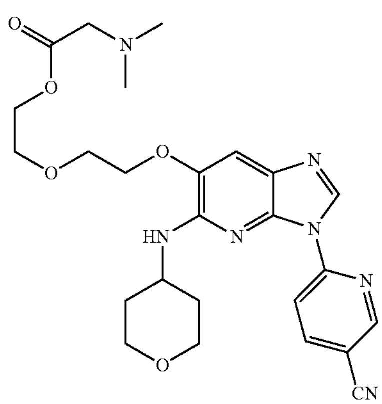 [SMILES: CN(C)CC(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl 2-(dimethylamino)acetate | Cpd 1 | F | 509.6 | 510.4 |
| 16 | 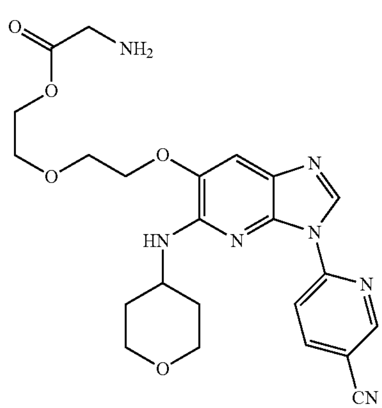 [SMILES: N#Cc1ccc(-n2cnc3cc(OCCOCCOC(=O)CN)c(NC4CCOCC4)nc32)nc1] | 2-[2-[3-(5-cyano-2-pyridyl)-5-(tetrahydropyran-4-ylamino)imidazo[4,5-b]pyridin-6-yl]oxyethoxy]ethyl 2-aminoacetate | Int 31 | Example 2.4 | 481.5 | 482.4 |

TABLE III-continued

Illustrative compounds of the invention.

| Cpd # | Structure | Name | SM | Method | MW | MS Mes'd |
|---|---|---|---|---|---|---|
| 17 | 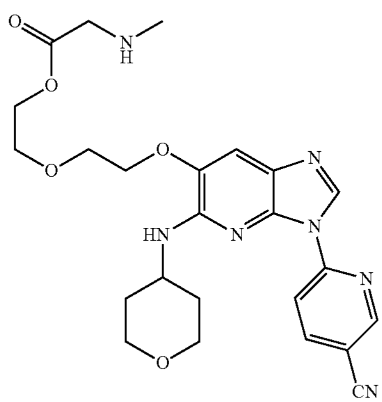 [SMILES: CNCC(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl 2-(methylamino)acetate | Int 32 | Example 2.5 | 495.5 | 496.3 |
| 18 | 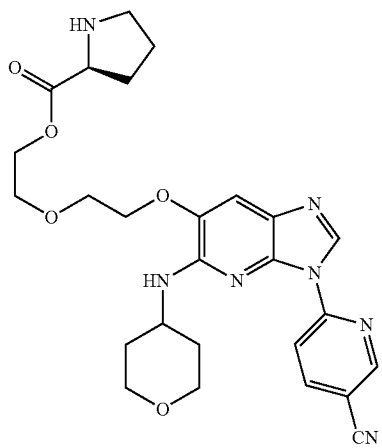 [SMILES: N#Cc1ccc(-n2cnc3cc(OCCOCCOC(=O)[C@@H]4CCCN4)c(NC4CCOCC4)nc32)nc1] | 2-[2-[3-(5-cyano-2-pyridyl)-5-(tetrahydropyran-4-ylamino)imidazo[4,5-b]pyridin-6-yl]oxyethoxy]ethyl (2S)-pyrrolidine-2-carboxylate | Int 33 | Example 2.6 | 521.6 | 522.5 |
| 19 | 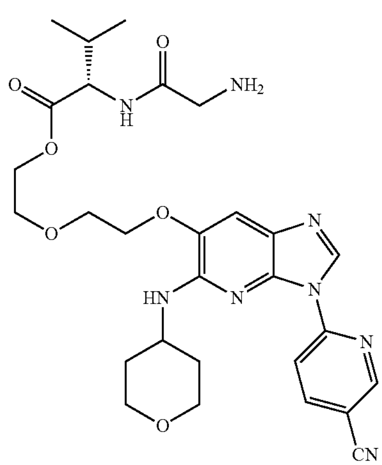 [SMILES: CC(C)[C@H](NC(=O)CN)C(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl (2S)-2-[(2-aminoacetyl)amino]-3-methyl-butanoate | Int 34 | Example 2.7 | 580.6 | 603.4 (M + Na) |

TABLE III-continued

Illustrative compounds of the invention.

| Cpd # | Structure | Name | SM | Method | MW | MS Mes'd |
|---|---|---|---|---|---|---|
| 20 | 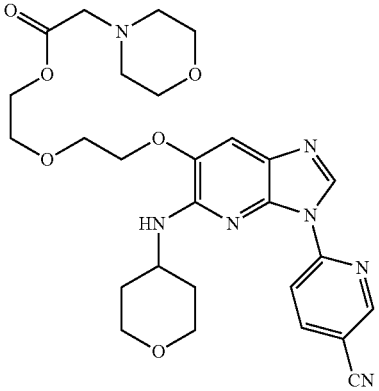 [SMILES: N#Cc1ccc(-n2cnc3cc(OCCOCCOC(=O)CN4CCOCC4)c(NC4CCOCC4)nc32)nc1] | 2-[2-[3-(5-cyano-2-pyridyl)-5-(tetrahydropyran-4-ylamino)imidazo[4,5-b]pyridin-6-yl]oxyethoxy]ethyl 2-morpholinoacetate | Cpd 1 | F | 551.6 | 552.4 |
| 21 | 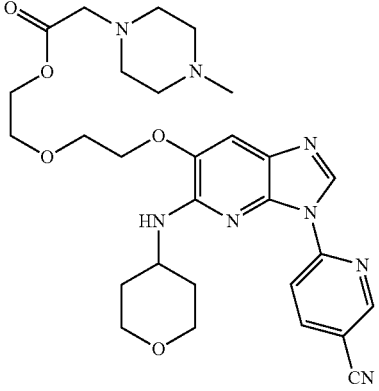 [SMILES: CN1CCN(CC(=O)OCCOCCOc2cc3ncn(-c4ccc(C#N)cn4)c3nc2NC2CCOCC2)CC1] | 2-[2-[3-(5-cyano-2-pyridyl)-5-(tetrahydropyran-4-ylamino)imidazo[4,5-b]pyridin-6-yl]oxyethoxy]ethyl 2-(4-methylpiperazin-1-yl)acetate | Cpd 1 | F | 564.6 | 565.3 |
| 22 | 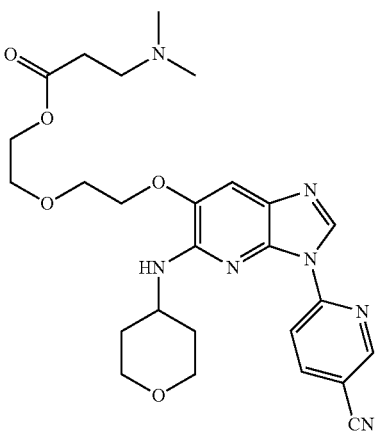 [SMILES: CN(C)CCC(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl 3-(dimethylamino)propanoate | Cpd 1 | F | 523.6 | 524.3 |

TABLE III-continued

Illustrative compounds of the invention.

| Cpd # | Structure | Name | SM | Method | MW | MS Mes'd |
|---|---|---|---|---|---|---|
| 23 | 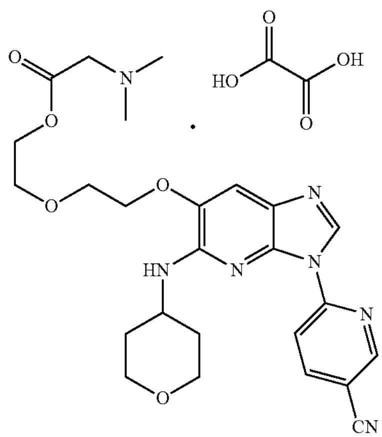 [SMILES: CN(C)CC(=O)OCCOCCOc1cc2ncn(-c3ccc(C#N)cn3)c2nc1NC1CCOCC1 ; O=C(O)C(=O)O] | 2-[2-[3-(5-cyano-2-pyridyl)-5-(tetrahydropyran-4-ylamino)imidazo[4,5-b]pyridin-6-yl]oxyethoxy]ethyl 2-(dimethylamino)acetate oxalic acid salt | Cpd 15 | G | 599.6 | ES+ 510.3 |
| 24 | 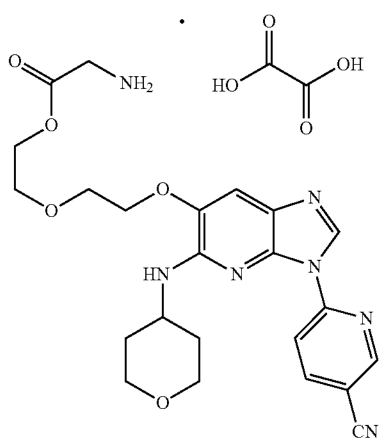 [SMILES: N#Cc1ccc(-n2cnc3cc(OCCOCCOC(=O)CN)c(NC4CCOCC4)nc32)nc1 ; O=C(O)C(=O)O] | 2-[2-[3-(5-cyano-2-pyridyl)-5-(tetrahydropyran-4-ylamino)imidazo[4,5-b]pyridin-6-yl]oxyethoxy]ethyl 2-aminoacetate oxalic acid salt | Cpd 16 | G | 571.6 | ES+ 482.3 |
| 25 | 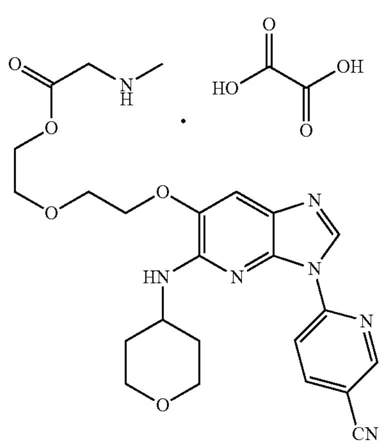 [SMILES: CNCC(=O)OCCOCCOc1cc2ncn(-c3ccc(C#N)cn3)c2nc1NC1CCOCC1 ; O=C(O)C(=O)O] | 2-[2-[3-(5-cyano-2-pyridyl)-5-(tetrahydropyran-4-ylamino)imidazo[4,5-b]pyridin-6-yl]oxyethoxy]ethyl 2-(methylamino)acetate oxalic acid salt | Cpd 17 | G | 585.6 | ES+ 496.3 |

TABLE III-continued

Illustrative compounds of the invention.

| Cpd # | Structure | Name | SM | Method | MW | MS Mes'd |
|---|---|---|---|---|---|---|
| 26 | 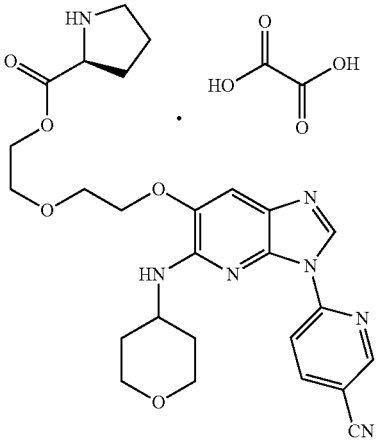 [SMILES: N#Cc1ccc(-n2cnc3cc(OCCOCCOC(=O)[C@@H]4CCCN4)c(NC4CCOCC4)nc32)nc1 ; O=C(O)C(=O)O] | 2-[2-[3-(5-cyano-2-pyridyl)-5-(tetrahydropyran-4-ylamino)imidazo[4,5-b]pyridin-6-yl]oxyethoxy]ethyl (2S)-pyrrolidine-2-carboxylate oxalic acid salt | Cpd 18 | G | 611.6 | ES+ 522.3 |
| 27 | 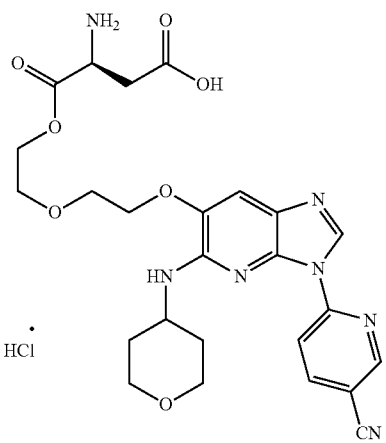 [SMILES: N#Cc1ccc(-n2cnc3cc(OCCOCCOC(=O)[C@@H](N)CC(=O)O)c(NC4CCOCC4)nc32)nc1] | (3S)-3-amino-4-[2-[2-[3-(5-cyano-2-pyridyl)-5-(tetrahydropyran-4-ylamino)imidazo[4,5-b]pyridin-6-yl]oxyethoxy]ethoxy]-4-oxo-butanoic acid hydrochloric acid salt | Int 35 | Example 2.8 | 576.0 | ES+ 540.5 |
| 28 | 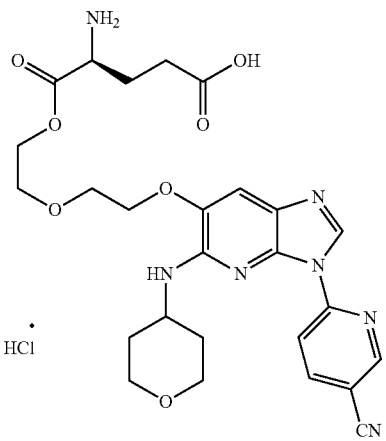 [SMILES: N#Cc1ccc(-n2cnc3cc(OCCOCCOC(=O)[C@@H](N)CCC(=O)O)c(NC4CCOCC4)nc32)nc1] | (4S)-4-amino-5-[2-[2-[3-(5-cyano-2-pyridyl)-5-(tetrahydropyran-4-ylamino)imidazo[4,5-b]pyridin-6-yl]oxyethoxy]ethoxy]-5-oxo-pentanoic acid hydrochloric acid salt | Int 36 | Example 2.9 | 590.0 | ES+ 554.6 |

TABLE III-continued

Illustrative compounds of the invention.

| Cpd # | Structure | Name | SM | Method | MW | MS Mes'd |
|---|---|---|---|---|---|---|
| 29 | 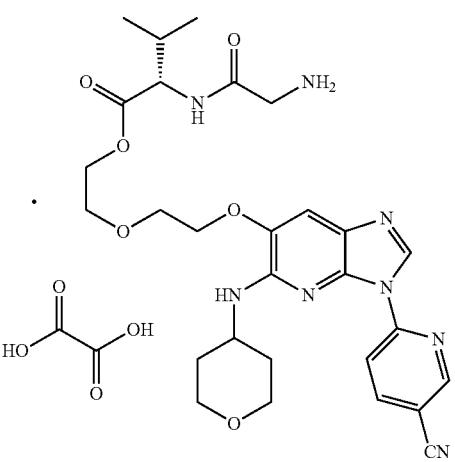 [SMILES: O=C(O)C(=O)O ; CC(C)[C@H](NC(=O)CN)C(=O)OCCOCCOc1cc2ncn(-c3ccc(C#N)cn3)c2nc1NC1CCOCC1] | 2-[2-[3-(5-cyano-2-pyridyl)-5-(tetrahydropyran-4-ylamino)imidazo[4,5-b]pyridin-6-yl]oxyethoxy]ethyl (2S)-2-[(2-aminoacetyl)amino]-3-methyl-butanoate oxalic acid salt | Cpd 19 | G | 670.6 | ES+ 581.4 |
| 30 | 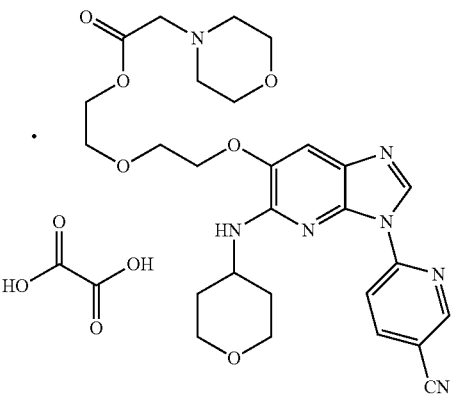 [SMILES: O=C(O)C(=O)O ; N#Cc1ccc(-n2cnc3cc(OCCOCCOC(=O)CN4CCOCC4)c(NC4CCOCC4)nc32)nc1] | 2-[2-[3-(5-cyano-2-pyridyl)-5-(tetrahydropyran-4-ylamino)imidazo[4,5-b]pyridin-6-yl]oxyethoxy]ethyl 2-morpholinoacetate oxalic acid salt | Cpd 20 | G | 641.6 | ES+ 510.3 |
| 31 | 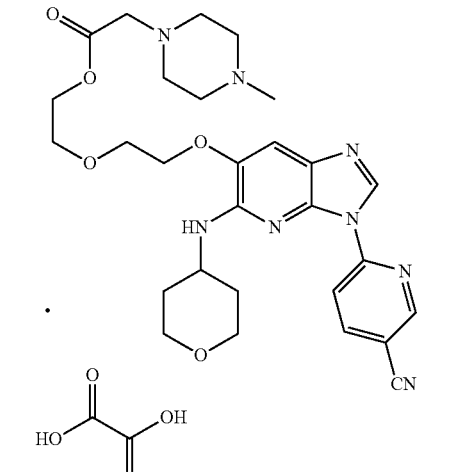 | 2-[2-[3-(5-cyano-2-pyridyl)-5-(tetrahydropyran-4-ylamino)imidazo[4,5-b]pyridin-6-yl]oxyethoxy]ethyl 2-(4-methylpiperazin-1-yl)acetate oxalic acid salt | Cpd 21 | G | 654.6 | ES+ 565.6 |

TABLE III-continued

Illustrative compounds of the invention.

| Cpd # | Structure | Name | SM | Method | MW | MS Mes'd |
|---|---|---|---|---|---|---|
| 32 | 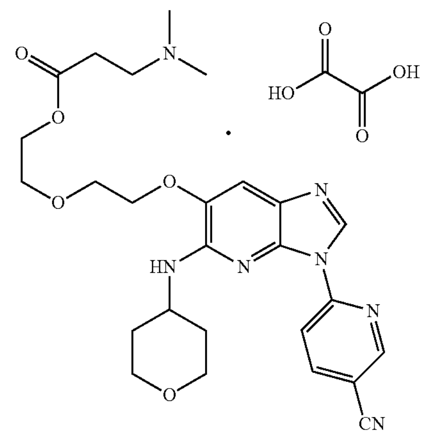 [SMILES: CN(C)CCC(=O)OCCOCCOc1cc2ncn(-c3ccc(C#N)cn3)c2nc1NC1CCOCC1 ; O=C(O)C(=O)O] | 2-[2-[3-(5-cyano-2-pyridyl)-5-(tetrahydropyran-4-ylamino)imidazo[4,5-b]pyridin-6-yl]oxyethoxy]ethyl 3-(dimethylamino)propanoate oxalic acid salt | Cpd 22 | G | 613.6 | ES+ 524.4 |
| 33 | 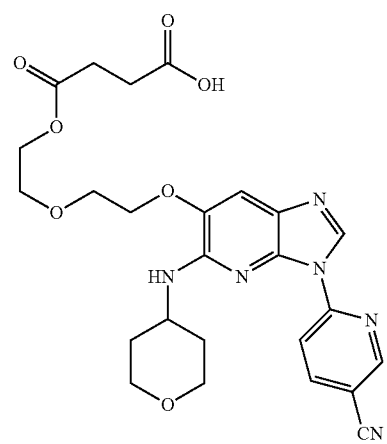 [SMILES: N#Cc1ccc(-n2cnc3cc(OCCOCCOC(=O)CCC(=O)O)c(NC4CCOCC4)nc32)nc1] | 4-[2-[2-[3-(5-cyano-2-pyridyl)-5-(tetrahydropyran-4-ylamino)imidazo[4,5-b]pyridin-6-yl]oxyethoxy]ethoxy]-4-oxo-butanoic acid | Int 37 | Example 2.10 | 524.5 | ES+ 525.3 |

SM = Starting Material,
Mtd = Method,
MS Mes'd = Mesured mass

TABLE IV

NMR data of representative compounds of the invention.

| Cpd # | NMR Data |
|---|---|
| 1 | $^1$H NMR (400 MHz, DMSO-d$_6$) δ 9.00 (1H, dd), 8.89-8.95 (1H, m), 8.75 (1H, s), 8.62 (1H, dd), 7.59 (1H, s), 6.04 (1H, d), 4.61-4.69 (1H, m), 4.22 (2H, dd), 4.05-4.17 (1H, m), 3.90-3.98 (2H, m), 3.83 (2H, dd), 3.50-3.60 (6H, m), 1.98-2.01 (2H, m), 1.55-1.70 (2H, m) |
| 2 | $^1$H NMR (400 MHz, DMSO-d$_6$) δ 8.87-9.06 (2H, m), 8.63 (1H), 7.65 (1H, br s), 6.38 (1H, d), 4.64 (1H, br s), 4.17-4.30 (3H, m), 3.80-3.88 (2H, m), 3.50-3.60 (4H, m), 3.40-3.48 (2H, m), 3.09-3.19 (3H, m), 2.15-2.35 (4H, m) |
| 3 | $^1$H NMR (400 MHz, DMSO-d$_6$) δ 8.98-9.03 (1H, m), 8.94 (1H), 8.87 (1H, s), 8.58 (1H, dd), 7.66 (1H, s), 4.58-4.70 (1H, m), 4.13-4.22 (2H, m), 4.08 (1H, s), 3.85-3.96 (1H, m), 3.80 (2H, dd), 3.46-3.58 (4H, m), 2.93 (3H, s), 1.91-2.07 (2H, m), 1.62 (2H, d), 1.50 (2H, d), 1.35-1.45 (2H, m), 1.13 (3H, s) |
| 4 | $^1$H NMR (300 MHz, CDCl$_3$) δ 9.02-9.11 (1H, m), 8.93 (1H, s), 8.75 (1H, d), 8.13 (1H, dd), 7.51 (1H, s), 4.16-4.29 (3H, m), 4.09 (2H, dd), 3.85-3.97 (2H, m), 3.67-3.74 (2H, m), 3.55-3.63 (2H, m), 3.41-3.55 (2H, m), 3.40 (3H, s), 3.00 (3H, s), 2.01 (2H, qd), 1.76 (2H, dd) |
| 5 | $^1$H NMR (400 MHz, DMSO-d$_6$) δ 9.00 (1H, dd), 8.92 (1H, dd), 8.76 (1H, s), 8.62 (1H, dd), 7.60 (1H, s), 6.00 (1H), 4.21 (2H, dd), 4.06-4.17 (1H, m), 3.90-3.97 (2H, m), 3.80-3.84 (2H, m), 3.61-3.66 (2H, m), 3.54 (2H, td), 3.47-3.51 (2H, m), 3.27 (3H, s), 1.99 (2H, dd), 1.54-1.67 (2H, m) |

TABLE IV-continued

NMR data of representative compounds of the invention.

| Cpd # | NMR Data |
|---|---|
| 6 | $^1$H NMR (400 MHz, DMSO-$d_6$) δ 8.99 (1H, d), 8.93 (1H, d), 8.74 (1H, s), 8.58 (1H, dd), 7.55 (1H, s), 6.19 (1H, d), 4.72 (1H, d), 4.61-4.68 (1H, m), 4.15-4.23 (2H, m), 3.89-4.02 (1H, m), 3.77-3.87 (2H, m), 3.67 (1H, td), 3.50-3.57 (4H, m), 2.17 (1H, d), 1.87-1.96 (1H, m), 1.71-1.86 (2H, m), 1.14-1.45 (4H, m) |
| 7 | $^1$H NMR (400 MHz, DMSO-$d_6$) δ 8.86-9.07 (2H, m), 8.76 (1H, br s), 8.63 (1H, d), 7.58 (1H, br s), 6.13 (1H, d), 4.51-4.76 (1H, m), 4.13-4.26 (2H, m), 3.72-3.94 (2H, m), 3.47-3.63 (5H, m), 2.09 (8H, m) |
| 8 | $^1$H NMR (300 MHz, CD$_3$OD) δ 9.03 (1H, d), 8.88-8.95 (1H, br s), 8.84 (1H, d), 8.41 (1H, dd), 7.46 (1H, br s), 4.14-4.36 (5H, m), 3.95-4.12 (4H, m), 3.86 (2H, dd), 3.60-3.76 (2H, m), 2.12 (2H, d), 1.64-1.85 (2H, m) |
| 9 | $^1$H NMR (400 MHz, CDCl$_3$) δ 9.02 (1H, d), 8.83 (1H, s), 8.76 (1H, br s), 8.13 (1H, d), 7.42 (1H, br s), 5.31 (1H, d), 4.36 (2H, br s), 4.24 (2H, br s), 4.18 (1H, br s), 4.08 (2H, d), 3.91 (2H, br s), 3.81 (2H, d), 3.62 (2H, t), 3.36 (1H, d), 2.16 (2H, d), 2.05 (1H, d), 1.26 (2H, br s), 0.98 (3H, d), 0.91 (3H, d) |
| 10 | $^1$H NMR (400 MHz, DMSO-$d_6$) δ 9.02 (1H, dd), 8.93 (1H, dd), 8.78 (1H, s), 8.64 (1H, dd), 7.60 (1H, s), 6.00 (1H, d), 4.40-4.46 (1H, m), 4.21-4.31 (3H, m), 4.09-4.18 (1H, m), 3.91-3.99 (2H, m), 3.85-3.90 (2H, m), 3.83 (1H, s), 3.75-3.80 (2H, m), 3.51-3.60 (2H, m), 2.04-2.15 (1H, m), 1.96-2.04 (2H, m), 1.58-1.68 (2H, m), 0.89-0.98 (6H, m) |
| 11 | $^1$H NMR (500 MHz, DMSO-$d_6$) δ 9.00 (1H, d), 8.84 (1H, d), 8.76 (1H, s), 8.59 (1H, dd), 7.60 (1H, s), 5.80 (1H, d), 5.25 (1H, br s), 4.65 (1H, br s), 4.20-4.27 (2H, m), 4.16 (1H, tt), 4.02-4.10 (1H, m), 3.79-3.84 (2H, m), 3.66-3.75 (2H, m), 3.56-3.62 (2H, m), 3.54 (4H, s), 1.82-1.94 (1H, m), 1.65-1.76 (1H, m) |
| 12 | $^1$H NMR (600 MHz, DMSO-$d_6$) δ 8.86-8.99 (2H, m), 8.69 (1H, s), 8.49-8.58 (1H, m), 7.50 (1H, s), 5.82 (1H, d), 4.58-4.71 (1H, m), 4.17 (2H, d), 4.11 (1H, s), 3.81 (2H, d), 3.68-3.77 (1H, m), 3.53 (4H, s), 1.71-1.86 (4H, m), 1.62 (2H, d), 1.44-1.53 (2H, m), 1.17 (3H, s) |
| 13 | $^1$H NMR (500 MHz, DMSO-$d_6$) δ 9.00 (1H, d), 8.93 (1H, d), 8.87 (1H, s), 8.58 (1H, dd), 7.65 (1H, s), 4.11-4.21 (2H, m), 4.08 (1H, s), 3.89 (1H, tt), 3.72-3.82 (2H, m), 3.55-3.62 (2H, m), 3.44-3.50 (2H, m), 3.25 (3H, s), 2.93 (3H, s), 1.99 (2H, qd), 1.62 (2H, d), 1.50 (2H, d), 1.40 (2H, td), 1.12 (3H, s) |
| 14 | $^1$H NMR (300 MHz, DMSO-$d_6$) δ 8.92-8.99 (2H, m), 8.73 (1H, s), 8.59 (1H, dd), 7.54 (1H, s), 5.79 (1H, d), 4.18 (2H, t), 4.08 (1H, br s), 3.80 (2H, t), 3.72-3.82 (1H, m), 3.60-3.68 (2H, m), 3.45-3.52 (2H, m), 3.26 (3H, s), 1.72-1.83 (4H, m), 1.57-1.68 (2H, m), 1.43-1.56 (2H, m), 1.17 (3H, s) |
| 15 | $^1$H NMR (400 MHz, CDCl$_3$) δ 9.03 (1H, dd), 8.83 (1H, s), 8.76 (1H, dd), 8.14 (1H, dd), 7.40 (1H, s), 5.42 (1H, d), 4.37-4.39 (2H, m), 4.07-4.26 (5H, m), 3.93-3.95 (2H, m), 3.82-3.84 (2H, m), 3.61-3.67 (2H, m), 3.24 (2H, s), 2.37 (6H, s), 2.14-2.24 (2H, m), 1.66-1.76 (2H, m) |
| 16 | $^1$H NMR (400 MHz, CDCl$_3$) δ 9.05 (1H, d), 8.85 (1H, s), 8.79 (1H, d), 8.16 (1H, dd), 7.44 (1H, s), 5.34 (1H, d), 4.38-4.40 (2H, m), 4.08-4.28 (5H, m), 3.94-3.96 (2H, m), 3.83-3.85 (2H, m), 3.62-3.68 (2H, m), 3.52 (2H, s), 2.37 (6H, s), 2.15-2.22 (2H, m), 1.65-1.75 (2H, m) |
| 17 | $^1$H NMR (400 MHz, CDCl$_3$) δ 9.05 (1H, dd), 8.85 (1H, s), 8.79 (1H, dd), 8.16 (1H, dd), 7.43 (1H, s), 5.36 (1H, d), 4.38-4.41 (2H, m), 4.08-4.28 (5H, m), 3.94-3.96 (2H, m), 3.83-3.85 (2H, m), 3.62-3.68 (2H, m), 3.45 (2H, s), 2.48 (3H, s), 2.15-2.22 (2H, m), 1.68-1.76 (2H, m) |
| 18 | $^1$H NMR (400 MHz, CDCl$_3$) δ 9.05 (1H, d), 8.85 (1H, s), 8.79 (1H, d), 8.16 (1H, dd), 7.43 (1H, s), 5.38 (1H, d), 4.37-4.40 (2H, m), 4.08-4.27 (5H, m), 3.94-3.96 (2H, m), 3.82-3.86 (3H, m), 3.62-3.68 (2H, m), 3.08-3.14 (1H, m), 2.91-2.97 (1H, m), 2.12-2.21 (3H, m), 1.86-1.95 (1H, m), 1.60-1.82 (4H, m) |
| 19 | $^1$H NMR (400 MHz, DMSO-$d_6$) δ 9.02 (1H, d), 8.93 (1H, d), 8.77 (1H, d), 8.64 (1H, dd), 8.30 (1H, br s), 7.61 (1H, s), 6.03 (1H, d), 5.14 (2H, br s), 4.09-4.35 (6H, m), 3.91-3.98 (2H, m), 3.85-3.87 (2H, m), 3.74-3.76 (2H, m), 3.52-3.59 (2H, m), 3.35 (2H, br s), 1.96-2.10 (3H, m), 1.58-1.68 (2H, m), 0.85-0.88 (6H, m) |
| 20 | $^1$H NMR (400 MHz, CDCl$_3$) δ 9.03 (1H, d), 8.83 (1H, s), 8.77 (1H, d), 8.14 (1H, dd), 7.42 (1H, s), 5.34 (1H, d), 4.36-4.39 (2H, m), 4.07-4.26 (5H, m), 3.93-3.95 (2H, m), 3.81-3.84 (2H, m), 3.74-3.77 (4H, m), 3.61-3.67 (2H, m), 3.28 (2H, s), 2.59-2.61 (4H, m), 2.16-2.20 (2H, m), 1.65-1.75 (2H, m) |
| 22 | $^1$H NMR (400 MHz, CDCl$_3$) δ 9.04 (1H, dd), 8.84 (1H, s), 8.77 (1H, dd), 8.14 (1H, dd), 7.42 (1H, s), 5.35 (1H, d), 4.33-4.36 (2H, m), 4.07-4.27 (5H, m), 3.94-3.96 (2H, m), 3.81-3.83 (2H, m), 3.61-3.68 (4H, m), 2.54-2.68 (4H, m), 2.27 (6H, s), 2.16-2.20 (2H, m), 1.66-1.76 (2H, m) |
| 23 | $^1$H NMR (400 MHz, DMSO-$d_6$) δ 9.00 (1H, dd), 8.92 (1H, dd), 8.77 (1H, s), 8.63 (1H, dd), 7.60 (1H, s), 6.02 (1H, d), 4.21-4.27 (4H, m), 4.06-4.18 (1H, m), 3.91-3.95 (2H, m), 3.84-3.86 (2H, m), 3.73-3.76 (2H, m), 3.62-3.68 (2H, br s), 3.51-3.57 (2H, m), 2.5 (6H, s), 1.96-2.01 (2H, m), 1.57-1.67 (2H, m) |
| 24 | $^1$H NMR (400 MHz, DMSO-$d_6$) δ 9.02 (1H, dd), 8.93 (1H, dd), 8.78 (1H, s), 8.64 (1H, dd), 7.62 (1H, s), 6.04 (1H, d), 4.32-4.35 (2H, m), 4.24-4.26 (2H, m), 4.09-4.18 (1H, m), 3.92-3.97 (2H, m), 3.86-3.89 (2H, m), 3.84 (2H, s), 3.77-3.79 (2H, m), 3.53-3.59 (2H, m), 1.98-2.02 (2H, m), 1.58-1.68 (2H, m) |
| 25 | $^1$H NMR (400 MHz, DMSO-$d_6$) δ 9.02 (1H, dd), 8.93 (1H, dd), 8.78 (1H, s), 8.64 (1H, dd), 7.62 (1H, s), 6.04 (1H, d), 4.33-4.35 (2H, m), 4.23-4.26 (2H, m), 4.09-4.18 (1H, m), 3.92-3.98 (4H, m), 3.86-3.89 (2H, m), 3.76-3.79 (2H, m), 3.52-3.59 (2H, m), 2.58 (3H, s), 1.96-2.04 (2H, m), 1.58-1.68 (2H, m) |
| 26 | $^1$H NMR (400 MHz, DMSO-$d_6$) δ 9.02 (1H, dd), 8.93 (1H, dd), 8.78 (1H, s), 8.64 (1H, dd), 7.62 (1H, s), 6.04 (1H, d), 4.29-4.42 (3H, m), 4.23-4.26 (2H, m), 4.10-4.18 (1H, |

TABLE IV-continued

NMR data of representative compounds of the invention.

| Cpd # | NMR Data |
|---|---|
|  | m), 3.92-3.97 (2H, m), 3.87-3.89 (2H, m), 3.77-3.80 (2H, m), 3.53-3.59 (2H, m), 3.12-3.25 (4H, m), 2.19-2.27 (1H, m), 1.92-2.03 (3H, m), 1.81-1.89 (2H, m), 1.58-1.68 (2H, m) |
| 28 | $^1$H NMR (400 MHz, DMSO-$d_6$) δ 9.04 (1H, dd), 8.92-8.94 (H, m), 8.78 (1H, s), 8.66 (1H, dd), 8.54 (3H, br s), 7.59 (1H, s), 4.38-4.43 (1H, m), 4.24-4.34 (3H, m), 4.08-4.17 (2H, m), 3.87-3.97 (4H, m), 3.77-3.80 (2H, m), 3.51-3.56 (2H, m), 2.37-2.54 (2H, m), 1.97-2.06 (4H, m), 1.59-1.69 (2H, m) |
| 30 | $^1$H NMR (400 MHz, DMSO-$d_6$) δ 9.01 (1H, dd), 8.93 (1H, d), 8.77 (1H, s), 8.63 (1H, dd), 7.61 (1H, s), 6.03 (1H, d), 4.21-4.27 (4H, m), 4.08-4.18 (1H, m), 3.91-3.98 (2H, m), 3.84-3.88 (2H, m), 3.72-3.76 (2H, m), 3.52-3.60 (6H, m), 3.32 (2H, s), 2.53-2.57 (4H, m), 1.96-2.04 (2H, m), 1.58-1.68 (2H, m) |
| 31 | $^1$H NMR (400 MHz, DMSO-$d_6$) δ 9.02 (1H, dd), 8.93 (1H, d), 8.78 (1H, s), 8.64 (1H, dd), 7.62 (1H, s), 6.03 (1H, d), 4.08-4.26 (5H, m), 3.92-3.98 (2H, m), 3.84-3.88 (2H, m), 3.72-3.76 (2H, m), 3.52-3.59 (2H, m), 3.36 (2H, s), 2.60-3.15 (11H, m), 1.96-2.04 (2H, m), 1.58-1.68 (2H, m) |
| 32 | $^1$H NMR (400 MHz, DMSO-$d_6$) δ 9.01 (1H, dd), 8.93 (1H, dd), 8.78 (1H, s), 8.63 (1H, dd), 7.62 (1H, s), 6.04 (1H, d), 4.21-4.27 (4H, m), 4.09-4.18 (1H, m), 3.91-3.98 (2H, m), 3.84-3.89 (2H, m), 3.73-3.78 (2H, m), 3.52-3.59 (2H, m), 3.24-3.28 (2H, t), 2.82-2.86 (2H, t), 2.73 (6H, s), 1.96-2.04 (2H, m), 1.57-1.67 (2H, m) |
| 33 | $^1$H NMR (400 MHz, DMSO-$d_6$) δ 12.19 (1H, br s), 9.02 (1H, dd), 8.94 (1H, dd), 8.77 (1H, s), 8.64 (1H, dd), 7.61 (1H, s), 6.03 (1H, d), 4.08-4.25 (5H, m), 3.91-3.97 (2H, m), 3.84-3.88 (2H, m), 3.70-3.75 (2H, m), 3.51-3.59 (2H, m), 2.45-2.55 (4H, m), 1.96-2.03 (2H, m), 1.58-1.68 (2H, m) |

Biological Examples

Example 3. In Vitro Assays 3.1. $IC_{50}$ Determination for Human IRAK-4

The $IC_{50}$ value for IRAK-4 is determined in a radioactive filter plate assay. The principle of the assay consists in the measurement of incorporated $^{33}$P into the RIP140 substrate upon phosphorylation by the enzyme IRAK-4 using [γ-$^{33}$P] ATP and ATP. Unincorporated $^{33}$P is removed by loading the samples on a filter plate (using a harvester, PerkinElmer) and 6 subsequent washing steps. Incorporated $^{33}$P in RIP140 is measured by a scintillation counter (Topcount, PerkinElmer) after addition of MicroScint™-20 (PerkinElmer, 6013621) to the filter plates.

5 µL of a water dilution series of test compound (starting from 20 µM or 6.6 µM highest concentration), from a 100% DMSO stock solution, 1/5 dilution, is added to the wells (final DMSO concentration of 1% in reaction assay). IRAK-4 (Carna Biosciences, 09-145) and RIP140 (SEQ ID1, cf. Table VII) are used at a final concentration of 10 ng/mL and 4 µM, respectively. The enzyme and substrate are diluted in 25 mM Tris pH 7.5, 0.025% Triton X-100, 5 mM MnCl$_2$, and 2 mM DTT to a total volume of 11 µL. The reaction is started by addition of 9 µL of 1 µM ATP (Sigma, A6419-5G)+0.25 µCi [γ-$^{33}$P]ATP (PerkinElmer, NEG602K001MC), diluted in the same buffer as enzyme and substrate. The mixture is incubated at 30° C. for 45 min. The reaction is terminated by adding 25 µL of 150 mM phosphoric acid (VWR, 1.00573.1000). Samples are transferred to filter plates and incorporated radioactivity is measured using a scintillation counter.

10 µM staurosporine (1% DMSO) is used as positive control (100% inhibition); vehicle (water+1% DMSO) as negative control (0% inhibition).

TABLE V

In vitro human IRAK-4 $IC_{50}$ of the compounds of the invention

| Cpd# | hIRAK-4 $IC_{50}$ (nM) |
|---|---|
| 1 | 6.35 |
| 2 | 25.4 |
| 3 | 21.7 |
| 4 | 523 |
| 5 | 13.8 |
| 6 | 4.85 |
| 7 | 14.3 |
| 8 | 51.4 |
| 9 | 13.5 |
| 11 | 14.3 |
| 12 | 0.95 |
| 13 | 39.1 |
| 14 | 3.45 |

3.2. Kinase Selectivity Profiling (Broad Panel)

Inhibition of human kinases is determined in radiometric kinase assays at REACTION BIOLOGY (Reaction Biology Corp., 1 Great Valley Parkway, Suite 2 Malvern, Pa. 19355, USA).

To determine its $IC_{50}$, a compound is tested at 10 doses starting from 10 µM (highest concentration), with 3-fold serial dilutions. $IC_{50}$ values are derived by fitting dose-response curves of % Remaining Enzyme Activity (relative to DMSO controls).

3.3. Kinase Selectivity Profiling (Focused Panel)

The purpose of this assay is to determine the activity and selectivity of a compound of the invention on a selected range of human kinases which may result in undesirable side-effects when inhibited (Dy & Adjei 2013; Force & Kolaja 2011).

3.3.1. Assay Protocol

The $IC_{50}$ value for off-target kinases is determined in radioactive filter plate assays. The principle of the assays consists in the measurement of incorporated $^{33}$P into a peptide substrate upon phosphorylation by the kinase enzyme using [γ-$^{33}$P]ATP and ATP. Unincorporated $^{33}$P is removed by loading the samples on a filter plate (using a harvester, PerkinElmer) and 6 subsequent washing steps. Incorporated $^{33}$P in the peptide substrate is measured by a scintillation counter (Topcount, PerkinElmer) after addition of MicroScint™-20 (PerkinElmer, 6013621) to the filter plates.

5 µL of a water dilution series of test compound (starting from 20 µM or 6.6 µM highest concentration), from a 100% DMSO stock solution, 1/5 dilution, is added to the wells (final DMSO concentration of 1% in reaction assay). Enzyme and peptide substrate are used at optimized concentrations (cf. Table VI). The enzyme and substrate are diluted in assay buffer to a total volume of 11 µL. The reaction is started by addition of 9 µL of ATP+[γ-$^{33}$P]ATP, diluted in the same buffer as enzyme and substrate. The mixture is incubated at 30° C. The reaction is terminated by adding 25 µL of 150 mM phosphoric acid. Samples are transferred to filter plates and incorporated radioactivity is measured using a scintillation counter.

The incubation time, assay buffer composition, and concentrations of ATP, enzyme and substrate are reported in Table VI for example kinase off-target assays.

10 µM staurosporine (1% DMSO) is used as positive control (100% inhibition); vehicle (water+1% DMSO) as negative control (0% inhibition).

TABLE VI

Conditions for human kinase off-targets inhibition assays

| Kinase, [Kinase] | Substrate, [Substrate] | ATP | Assay buffer | Incubation time |
|---|---|---|---|---|
| ABL (Life Technologies, P3049), 40 ng/mL | PolyGT (Sigma-Aldrich, P0275), 5 µg/mL | 0.5 µM ATP + 0.25 µCi/25 µL [γ-$^{33}$P]ATP | 50 mM Tris pH 7.7 0.03% Triton X-100 1 mM DTT 25 mM MgCl$_2$ | 60 min |
| Aurora B (Carna BioSciences, 05-102), 10 ng/mL | Histone H3 peptide (SEQ ID2), 0.5 µM | 1.3 µM ATP + 0.25 µCi/25 µL [γ-$^{33}$P]ATP | 25 mM Tris pH 7.7 0.01% Triton X-100 5 mM MgCl$_2$ 5 mM DTT | 90 min |
| CDK2 (Carna Biosciences, 04-103), 30 ng/mL | Histone H1-derived peptide (SEQ ID3), 0.36 µM | 0.1 µM ATP + 0.25 µCi/25 µL [γ-$^{33}$P]ATP | 8 mM MOPS pH 7.0 0.01% Brij-35 1 mM DTT 5 mM MnCl$_2$ | 60 min |
| CDK9 (Millipore, 14-685), 230 ng/mL | PDKtide (SEQ ID4), 0.5 µM | 0.25 µM ATP + 0.125 µCi/25 µL [γ-$^{33}$P]ATP | 20 mM MOPS pH 7.0 0.01% Triton X-100 5 mM MnCl$_2$ | 60 min |
| c-KIT (Millipore, 14-559), 0.01 mU/µL | PolyGT (Sigma-Aldrich, P0275), 0.1 mg/mL | 3 µM ATP + 0.25 µCi/25 µL [γ-$^{33}$P]ATP | 16 mM Tris pH 7.0 500 µM EDTA 0.01% Triton X-100 10 mM MnCl$_2$ 1 mM DTT 10 mM MgOAc | 90 min |
| GSK3b (Carna Biosciences, 04-141), 20 ng/mL | Phospho glycogen synthase peptide2 (Millipore, 12-241), 1.25 µM | 1.5 µM ATP + 0.25 µCi/25 µL [γ-$^{33}$P]ATP | 50 mM Tris pH 8.0 0.01% Brij-35 1 mM DTT 5 mM MgOAc | 90 min |
| c-SRC (Carna Biosciences, 08-173), 8 ng/mL | PolyGT (Sigma-Aldrich, P0275), 2 µg/mL | 0.25 µM ATP + 0.125 µCi/25 µL [γ-$^{33}$P]ATP | 25 mM MOPS pH 7.0 10 mM MnCl$_2$ 2.5 mM DTT 0.01% Brij35 | 60 min |

TABLE VII

Peptide substrates used in human kinase off-targets inhibition assays

| Substrate | SEQ ID No. | Sequence | Provider |
|---|---|---|---|
| RIP140 peptide | 1 | CYGVASSHLKTLLKKSKVKDQ | Almac Group Ltd. 20 Seagoe Industrial Estate Craigavon BT63 5QD UK |
| Histone H3 peptide | 2 | ARTKQTARKSTGGKAPRKQLC | AnaSpec Inc. 34801 Campus Drive Fremont, CA 94555 USA |
| Histone H1-derived peptide | 3 | GGGPATPKKAKKL | AnaSpec Inc. 34801 Campus Drive Fremont, CA 94555 USA |

TABLE VII-continued

Peptide substrates used in human kinase off-targets inhibition assays

| Substrate | SEQ ID No. | Sequence | Provider |
|---|---|---|---|
| PDKtide | 4 | KTFCGTPEYLAPEVRREPRILSEEEQE MFRDFDYIADWC | Thermo Fisher Scientific Inc. 81 Wyman St. Waltham, MA 02451 USA |

TABLE VIII

In vitro human kinase off-targets $IC_{50}$ of illustrative compounds of the invention

| Cpd# | ABL $IC_{50}$ (nM) | Aurora B $IC_{50}$ (nM) | CDK2 $IC_{50}$ (nM) | CDK9 $IC_{50}$ (nM) | GSK3b $IC_{50}$ (nM) | c-SRC $IC_{50}$ (nM) |
|---|---|---|---|---|---|---|
| 1 | — | — | >6670 | >1330 | >6670 | >1330 |
| 2 | — | — | >1330 | 712 | >1330 | >1330 |
| 5 | 2690 | — | >4000 | 2290 | >4000 | >2940 |
| 6 | 656 | — | 2670 | 1030 | >4000 | 754 |
| 9 | 633 | — | >4000 | 639 | 3250 | 286 |
| 11 | — | — | >1330 | 834 | >1330 | >1330 |
| 12 | 138 | >1880 | 944 | 1150 | >1330 | 477 |
| 14 | — | — | 1380 | 1390 | 2240 | 319 |

3.3.2. Conclusion

The data of Table VIII, in relation to those of Table V, show the lower inhibitory potency of compounds of the invention in kinase off-targets versus in IRAK-4. These data confirm the selectivity of compounds of the invention towards IRAK-4, thus limiting the risk of side effects associated with kinase off-targets inhibition.

3.4. Cellular Assay: CL097 Activated TNFα Release Inhibition in PBMCs

The compounds of the invention are tested in a cellular assay using primary isolated human peripheral blood mononuclear cells (PBMCs) to measure the secretion of the inflammatory cytokine TNFα upon TLR activation using the specific TLR7/8 agonist, CL097. The release of TNF protein in the cell culture supernatant is quantified by a human TNFα enzyme-linked immunosorbent assay (ELISA) protocol.

3.4.1. Isolation of Human Primary PBMCs from Human Buffy Coat

A human buffy coat (provided by the Croatian Institute for Transfusion Medicine) is kept overnight at 4° C. and processed the next day for isolation of PBMCs. PBMCs are isolated by density gradient centrifugation using Ficoll-Paque™ PLUS (GE HealthCare, 17-1440-02). Equal volumes of a buffy coat are diluted 1:4 with sterile PBS (1×) and 35 mL is carefully layered on top of 15 mL Ficoll-Paque PLUS in appropriate 50 mL Falcon® tubes. The tubes are centrifuged for 35 min at 1500 rpm at r.t. without acceleration or break. After centrifugation, the upper plasma layer is removed and the mononuclear cell ring is carefully isolated and transferred to a fresh Falcon® tube. The isolated cell suspension is diluted in PBS up to 50 mL followed by a centrifugation step at 1300 rpm for 10 min at r.t. After 2 additional washing steps in PBS and cell pooling, the remaining erythrocytes are lysed by resuspension of the cell pellet in 50 mL of AKL lysis buffer (150 mM $NH_4Cl$, 10 mM $NaHCO_3$, 1 mM $Na_2EDTA$, pH 7.4) followed by gentle mixture. The 50 mL suspension is then centrifuged at 1300 rpm for 10 min at r.t. followed by removal of supernatant and resuspension of the cell pellet in culture medium (RPMI 1640 (Gibco, 21875)+10% fetal bovine serum (FBS, Biowest, S1810) heat inactivated for 30 min at 56° C.+Pen/Strep (Gibco, 15240)).

3.4.2. Compound Treatment and Triggering in PBMC Assay

Cells are counted using a hematologic analyzer (Sysmex XS-500i) and plated at a density of $4.0 \times 10^5$ cells per well in 160 μL culture medium in 96-well culture plates. Subsequently, PBMCs are pre-incubated with test compound by addition of 20 μL of 10× concentrated compound solution for 1 hour at 37° C. and 5% $CO_2$. The compounds are tested at different concentrations and prepared by 3-fold serial dilutions from the 10 mM stock solution in DMSO followed by a 1:50 dilution step in 2× M199 medium (Gibco, 21157-029) supplemented with 1% FBS and 1% Pen/Strep. Final test concentrations in the assay start from 20 μM, with subsequent 3-fold serial dilutions and equal final DMSO concentrations of 0.2%. After the compound pre-incubation step, the PBMCs are triggered by adding 20 μL of a 10 μg/mL CL097 solution (InvivoGen, tlrl-c97-5) to the wells with final assay volume of 200 μL per well and 1 μg/mL final CL097 trigger concentration. Negative controls are adjusted with equal DMSO concentrations without CL097 trigger. The assay plates are then incubated for 4 h in a humidified incubator at 37° C. and 5% $CO_2$. Cell supernatants are then harvested by transferring the cell medium into a 384 deep well plate and immediately transferred to the ELISA plate for quantification of human TNFα.

3.4.3. Quantification of TNFα by ELISA

The levels of secreted TNFα in the cell supernatants are quantified in an antibody capture activity assay (ELISA). A white Greiner Lumitrac™ 384-well plate is coated with 40 μL per well of a 1 μg/mL anti-human TNFα antibody solution (MAb1; BD Biosciences, 551220) diluted in PBS for an overnight incubation at 4° C. After washing the wells with 100 μL PBS, the remaining binding sites are blocked with 100 μL of blocking buffer (PBS+1% bovine serum albumin+5% sucrose) and incubated for 4 h at r.t. Subsequent to the blocking step, the wells are washed once with PBS with Tween 20 (PBST), followed by addition of samples and standards. Samples containing TNFα are diluted 1/3 in dilution buffer and 40 μL is added for an overnight incubation at 4° C. The wells are then washed 3 times, twice with PBST and once with PBS, following addition of 35 μL of secondary biotinylated anti-TNFα detection antibody (MAb11; BD Biosciences, 554511) in a 1/2000 diluted format at final concentration of 250 ng/mL. After 2 hours of incubation at r.t. and appropriate washing steps (2×PBST, 1×PBS), the wells are incubated with 35 µL of a 1/4000 diluted horseradish peroxidase-conjugated streptavidin solution (Life Technologies, SNN2004), followed by a 45 min incubation step at r.t. in the dark. The wells are then washed 3 times (2×PBST, 1×PBS), followed by 5 min incubation with 50 µL of Chemiluminescence ELISA Substrate solution (Roche, 11582950001). The converted substrate luminescent signal is measured in a PerkinElmer EnVision 2104 Multilabel Plate Reader.

3.4.4. Data Analysis

All controls are measured within the linear range of the human TNFα standard curve of the ELISA. All data are checked for validity against the assay quality parameters (signal/background>2 and Z'>0.3).

Unstimulated samples (no trigger/vehicle (0.2% DMSO)) are used as positive control (100% inhibition). As negative control (0% inhibition), the stimulated samples (trigger/vehicle (0.2% DMSO)) are used. The positive and negative controls are used to calculate Z' and percent inhibition (PIN) values, according to the following formula:

$$PIN = \frac{RCLU \text{ trigger/vehicule} - RCLU \text{ test compound}}{RCLU \text{ trigger/vehicule} - RCLU \text{ no trigger/vehicule}} \times 100;$$

with RCLU = Relative Chemiluminescent Light Units.

PIN values are plotted for compounds tested in concentration-response mode, and $IC_{50}$ values are derived using the GraphPad Prism® software applying a non-linear regression (sigmoidal) curve fitting.

3.5. Cellular Assay: Cancer Cell Assays

3.5.1. Cell Lines

Human lymphoma cells from the OCI-Ly3, OCI-Ly10, OCI-Ly7, and OCI-Ly19 cell lines (from DSMZ, Germany or ATTC, US) are cultured in IMDM (Gibco®, 21980-032) supplemented with 10% fetal bovine serum (Invitrogen, S7524) or 20% human serum (Invitrogen, 34005100) at 37° C. in 5% $CO_2$.

3.5.2. Cell Growth Assay

Lymphoma cells (2-7×10³) are plated in 96 well plates, and treated with different doses of test compounds from 30 µM (1/3 dilutions, 8 points). The treated cells are incubated for 7 days at 37° C. in 5% $CO_2$. Staurosporin (10 µM) is used as positive control.

Cell growth is determined by incubating the cells with alamarBlue® (Invitrogen, DAL 1025), according to the manufacturer's instructions. Fluorescence is measured using a PerkinElmer EnVision® plate reader. A percentage of growth inhibition is calculated using DMSO vehicle values as 0% inhibition and staurosporin values as 100% inhibition.

3.6. IL-1 and TNFα Response Cellular Assay in SW1353 Cells

The aim of this assay is to evaluate the selectivity of compounds of the invention for the activated TLR/IRAK-4 pathway in an in vitro human cellular assay setting. SW1353 cells are from a chondrocytic cell line and are responsive to both the interleukin 1 (IL-1) and the TNFα cytokine triggers. Both cytokine triggers induce the expression of interleukin 6 (IL-6) and MMP13 by these cells. IL-6 and MMP13 releases are used as readouts in this assay and represent a measure for the level of inhibition of the TLR/IRAK-4 pathway by the tested compound. The IL-1 trigger signals through an IRAK-4 dependent pathway, whereas TNFα does not require IRAK-4 for signaling. Therefore, compounds selectively inhibiting IRAK-4 only impact IL-1 driven expression of MMP13 or IL-6 by SW1353 cells and do not impact TNFα driven expression of these proteins.

3.6.1. Harvesting and Seeding of SW1353 Cells

SW1353 cells are cultured in DMEM supplemented with 10% FBS and 1% Penicillin/Streptomycin. Cells are incubated at 37° C. in a humidified atmosphere of 5% $CO_2$ and subcultured twice a week. During subculturing, trypsin-EDTA is used to detach the cells, followed by a neutralization step with cell culture medium. After centrifugation (1,000 rpm during 5 min), the pellet is resuspended in cell culture medium and cells are counted using an automated cell counter (Invitrogen Countess™).

Cells are used at passage 16 and plated at a density of 15,000 cells per well in 120 µL cell culture medium in 96-well culture plates. Cells are allowed to attach during overnight incubation.

3.6.2. Compound Treatment and Triggering in SW1353 Assay

SW1353 cells are pre-incubated with test compound by addition of 15 µL of 10× concentrated compound solution for 2 h at 37° C. and 5% $CO_2$. The compounds are tested at different concentrations and prepared by 3-fold serial dilutions from the 10 mM stock solution in DMSO followed by a 1/50 dilution step in cell culture medium. Final test concentrations in the assay start from 20 µM, with subsequent 3-fold serial dilutions with equal final DMSO concentrations of 0.2%. After the compound pre-incubation step, the SW1353 cells are triggered by addition of 15 µL of 10× concentrated IL-1f (Peprotech, 200-01B) or TNFα trigger (Peprotech, 300-01A) to the wells with final assay volume of 150 µL per well and final trigger concentration of 1 ng/mL and 10 ng/mL, respectively. Negative controls are adjusted with equal DMSO concentrations without trigger. The assay plates are then incubated in a humidified incubator at 37° C. and 5% $CO_2$. Cell supernatants are harvested 24 h and 48 h later by transferring the cell medium into a V-bottom polypropylene 96-well plate and stored at −80° C. until ELISA readout.

3.6.3. Quantification of IL-6 by ELISA

The levels of secreted IL-6 in the cell supernatants are quantified in an enzyme-linked immunosorbent assay (ELISA). A white Lumitrac™ 384-well plate is coated overnight with 40 µL per well of a 1 µg/mL anti-human IL-6 mouse antibody (R&D Systems, MAB206) solution diluted in PBS at 4° C. After washing the wells twice with 100 µL PBST and once with PBS, the remaining binding sites are blocked with 100 µL of blocking buffer (1% BSA and 5% sucrose in PBS) and incubated for 4 h at r.t. Subsequent to the blocking step, the wells are washed once with PBST followed by addition of either samples or recombinant human IL-6 (R&D Systems, 206-IL-050) as standard. Samples are diluted 1/20 in dilution buffer and 40 μL is added for an overnight incubation at 4° C. The wells are then washed 3 times, twice with PBST and once with PBS, following addition of 35 μL of secondary biotinylated anti-IL-6 detection antibody (human IL-6 biotinylated goat polyclonal antibody (R&D Systems, BAF206)) at a final concentration of 50 ng/mL. After 2 h of incubation at r.t. and appropriate washing steps (twice with PBST and once with PBS), the wells are incubated with 35 μL of a 1/2,000 diluted streptavidin-HRP solution (Invitrogen, SNN2004), followed by a 45 min incubation at r.t. in the dark. The wells are then washed 3 times (twice with PBST and once with PBS), followed by 5 min incubation with a 50 μL of chemiluminescence ELISA substrate solution (Roche, 11 582 950 001). Luminescence of the converted substrate is measured with a Luminoskan™ Ascent luminometer.

3.6.4. Quantification of MMP13 by ELISA

The levels of secreted MMP13 in the cell supernatants are quantified in an antibody capture activity assay. For this purpose, black Nunc® MaxiSorp™ 384-well plates are coated with 35 μL of a 1.5 μg/mL anti-human MMP13 antibody solution overnight at 4° C. After washing the wells twice with PBST, the remaining binding sites are blocked with 100 μL 5% non-fat dried milk in PBS for 24 h at 4° C. Subsequent to the blocking step, the wells are washed twice with PBST followed by addition of samples and standards. Samples are 1/5 diluted in dilution buffer and 35 μL is added for 4 h at r.t. The wells are then washed twice with PBST. Subsequently, the MMP13 protein is fully activated by addition of 35 μL of a 1.5 mM APMA solution (Sigma-Aldrich, A9563) and incubated at 37° C. for 1 h. The wells are then washed twice with PBST and 35 μL MMP13 substrate (OMNIMMP® fluorogenic substrate (BIOMOL, P-126)) is added. After incubation for 1 h at 37° C., fluorescence of the converted substrate is measured with a PerkinElmer EnVision® (excitation wavelength: 320 nm, emission wavelength: 405 nm).

3.6.5. Data Analysis and Calculation

All controls are measured within the linear range of the human IL-6 and MMP13 standard curve of the ELISA. All data generated are validated against the assay quality parameters (signal/background>2 and Z'>0.3).

Unstimulated samples (no trigger/vehicle (0.2% DMSO)) are used as positive control (100% inhibition). As a negative control (0% inhibition), the stimulated samples (trigger/vehicle (0.2% DMSO)) are used. The positive and negative controls are used to calculate Z' and percent inhibition (PIN) values.

Percentage inhibition (PIN)=((RUtrigger/veh−RUtest compound)/(RUtrigger/veh−RUno trigger/veh)*100); with RU meaning relative chemiluminescent light units or relative fluorescence units for IL-6 and MMP13 ELISA, respectively. PIN values are plotted for test compounds tested in concentration-response and $IC_{50}$ values are derived using the GraphPad Prism® software applying non-linear regression (sigmoidal) curve fitting.

TABLE IX

SW1353 cellular selectivity assay results of illustrative compounds of the invention

| | IL-1β trigger | | TNFα trigger | |
|---|---|---|---|---|
| Cpd# | IL-6 $IC_{50}$ (nM) [PIN at 20 μM] | MMP13 $IC_{50}$ (nM) [PIN at 20 μM] | IL-6 $IC_{50}$ (nM) [PIN at 20 μM] | MMP13 $IC_{50}$ (nM) [PIN at 20 μM] |
| 1 | 54 [89%] | 36 [81%] | >20000 [54%] | >20000 [26%] |
| 12 | 40 [80%] | 29 [75%] | >20000 [22%] | >20000 [36%] |

3.6.6. Conclusion

The data of Table IX show that compounds of the invention potently inhibit IL-6 and MMP13 expression in SW1352 cells triggered by IL-1β, whereas the effect of such compounds on TNFα triggered events is limited, both in terms of potency and maximal amplitude. These data confirm the selectivity of compounds of the invention towards IRAK-4 driven pathways, with very limited impact on TNFα signaling, which may in turn limit the occurrence of treatment-associated side effects such as neutropenia and infection.

Example 4. ADME Assays

4.1. Kinetic Solubility

Starting from a 3.3 mM DMSO stock solution of compound, a serial dilution of the compound is prepared in DMSO by performing 1/2 dilutions: 3.3, 1.6, 0.83, 0.41 and 0.21 mM. This dilution series is transferred to a clear V-bottom 96 well plate (Greiner, 651201) and further diluted 1/33.5 in 0.1 M phosphate buffer pH 7.4 or 0.1 M citrate buffer pH 3.0. Final compound concentrations are 99.5, 49.7, 24.9, 12.4 and 6.22 μM. The final DMSO concentration does not exceed 3%. As a positive control for precipitation, pyrene (30 mM) is added to the corner wells of each 96 well plate. The assay plates are sealed and incubated for 1 h at 37° C. while shaking at 230 rpm. The plates are then scanned under a white light microscope, yielding individual pictures (50× magnification) of the precipitate per concentration. Each well is analyzed by image analysis software, and the highest concentration at which the compound appears completely dissolved is reported.

4.2. Microsomal Stability

A 10 mM stock solution of compound in DMSO is diluted three-fold in DMSO. This pre-diluted compound solution is then diluted to 2 μM in a 105 mM phosphate buffer (pH 7.4) in a 96 deep well plate (Nunc, 278752) and pre-warmed at 37° C.

A glucose-6-phosphate-dehydrogenase (G6PDH, Roche, 10127671001) working stock solution of 700 U/mL is diluted with a factor 1:700 in a 105 mM phosphate buffer, pH 7.4. A co-factor mix containing 0.528 M MgCl$_2$.6H$_2$O (Sigma, M2670), 0.528 M D-glucose-6-phosphate (Sigma, G7879) and 0.208 M NADP+(Sigma, N0505) is diluted with a factor 1:8 in a 105 mM phosphate buffer, pH 7.4.

A working solution is made containing 1 mg/mL liver microsomes (Tebu-bio) of the species of interest (e.g., human, mouse, rat, dog), 1.2 U/mL G6PDH and co-factor mix (6.6 mM MgCl$_2$, 6.6 mM glucose-6-phosphate, 2.6 mM NADP+). This mix is pre-incubated for 15 min, but never more than 20 min, at r.t.

After pre-incubation, the compound dilution and the mix containing the microsomes, are added together in equal amount and incubated for 30 min at 300 rpm. For the 0 min time point, two volumes of MeCN are added to the compound dilution before the microsome mix is added. The final concentrations during incubation are: 1 µM test compound or control compound, 0.2% DMSO, 0.5 mg/mL microsomes, 0.6 U/mL G6PDH, 3.3 mM MgCl$_2$, 3.3 mM glucose-6-phosphate and 1.3 mM NaDP+.

After 30 min of incubation at 37° C., the reaction is stopped with 2 volumes of MeCN.

Samples are mixed, centrifuged and the supernatant is harvested for analysis on LC-MS/MS. The instrument responses (i.e. peak heights) are referenced to the zero time point samples (considered as 100%) in order to determine the percentage of compound remaining. Propranolol and verapamil are included as references in the assay design.

The data on microsomal stability are expressed as a percentage of the total amount of compound remaining after 30 min incubation.

4.3. Metabolic Stability in S9 Subcellular Fraction

The aim of this assay is to assess compound metabolism by aldehyde oxidase by determination of their in vitro metabolic stability in S9 subcellular fraction.

A 10 mM stock solution of compound in DMSO is first diluted in DMSO (40 fold) to obtain 250 µM concentration. This compound solution is further diluted with water (5 fold) to obtain a 50 µM compound working solution (to obtain compound final concentration of 1 µM). Hydralazine (selective inhibitor of aldehyde oxidase) is prepared in water at 5 mM (to obtain final concentration of 100 µM). Incubation mixtures are prepared by adding 10 µL of liver S9 suspension (human, rat, mouse, monkey, BD Gentest™, 20 mg/mL) to 86 µL of 50 mM potassium phosphate buffer, pH 7.4 at 37° C. (final concentration of 2 mg protein/mL). 2 µL of 5 mM hydralazine is added for incubations with the addition of selective inhibitor or 2 µL of water, for incubations without inhibitor. After 5 min pre-warming, the reaction is initiated by the addition of 2 µL of 50 µM test compound to the incubation mixture. After 0, 3, 6, 12, 18 and 30 min of incubation, the reaction (100 µL) is terminated with 300 µL of MeCN:MeOH (2:1) with 1% acetic acid mixture containing 10 ng/mL of warfarin as analytical internal standard. Samples are mixed, centrifuged and the supernatant analyzed by LC-MS/MS. Phtalazine is included as positive control.

The instrument responses (peak area ratios of compound and internal standard) are referenced to the zero time point samples (considered as 100%) in order to determine the percentage of compound remaining. Plots of the % of compound remaining are used to determine the half-life and intrinsic clearance in the S9 incubations using the GraphPad Prism® software. The following formula is used to calculate in vitro intrinsic clearance (µL/min/mg):

$$CL_{int}(\mu L/min/mg)=0.693/t_{1/2}(min)*(mL\ of\ incubation/mg\ protein)*1000$$

Test compounds can be classified as substrates of aldehyde oxidase if clearance by S9 is inhibited by hydralazine. Species specific clearance of test compound may also indicate metabolism by aldehyde oxidase.

4.4. Metabolic Stability in Hepatocytes

A 10 mM stock solution of test compound in DMSO is first diluted in DMSO to 3 mM, and then in modified Krebs-Henseleit buffer (Sigma, K3753) to 5 µM. This compound dilution is added to a suspension of pooled cryopreserved hepatocytes (BioreclamationIVT) at 37° C. under gentle shaking. Final reaction conditions are: 1 µM of test compound, 0.03% DMSO, 0.5 million viable hepatocytes/mL, and 75 µL incubation volume. Testosterone (1 µM) and 7-hydroxycoumarin (1 µM) are used, respectively as phase I and phase II metabolic reaction controls.

After 0, 10, 20, 45, 90, 120 and 180 min of incubation, the reaction is terminated with 225 µL of MeCN:MeOH (2:1) containing 10 ng/mL of warfarin sodium as analytical internal standard. Samples are mixed, centrifuged and the supernatant analyzed by LC-MS/MS.

The instrument responses (ratios of test compound and internal standard peak areas) are referenced to the zero time point samples (considered as 100%) in order to determine the percentage of compound remaining.

Plots of percentage compound remaining are used to determine the half-life and intrinsic clearance in the hepatocyte incubations using the GraphPad Prism® software.

4.5. CYP Inhibition

The inhibitory potential of a test compound for human cytochrome P450 isoenzymes (CYP1A2, 2C9, 2C19, 2D6 and 3A4) is assessed using cDNA-expressed human cytochrome P450 isoenzymes and non-fluorescent substrates which are metabolized to fluorescent metabolites.

Compounds are tested at 3.3 and 10 µM, with a final DMSO concentration of 0.3%. Compounds are incubated for 15 min with enzyme before the cofactor-substrate mix is added. Final reaction concentrations in cofactor mix for the CYP3A4 (BD Biosciences, 456202), CYP2C9 (BD Biosciences, 456258), CYP2C19 (BD Biosciences, 456259) and CYP1A2 (BD Biosciences, 456203) assays are: 0.4 U/mL glucose-6-phophate-dehydrogenase (G6PDH, Roche, 10165875001), 3.3 mM MgCl$_2$ (Sigma, M2670), 3.3 mM D-glucose-6-phosphate (Sigma, G7879) and 1.3 mM NADP+(Sigma, N0505). For CYP2D6 (BD Biosciences, 456217), final reaction concentrations in the assay are 0.4 U/mL G6PDH, 0.41 mM MgCl$_2$, 0.41 mM D-glucose-6-phosphate and 8.2 µM NADP+. The concentrations of enzyme and substrate are reported in Table X. After an incubation period, the reaction is stopped by adding a stop solution. For experiments with DBF as substrate, a 2 N NaOH stop solution is used, while for all other substrates the stop solution is 80% MeCN/20% 0.5 M Tris base.

Fluorescence is read either immediately (for CEC, AMMC, BFC), or after 20 min (for CYP2C9 and CYP3A4 using DBF as substrate) on a PerkinElmer EnVision® reader at the appropriate excitation and emission wavelength (cf. Table X).

The percentage inhibition of CYP by the test compound is then calculated by normalizing the data to blank samples: 100% inhibition is the blank sample stopped before addition of the enzyme/substrate mix, and 0% inhibition is the blank sample stopped after the enzymatic reaction has occurred (50 min).

TABLE X

Inhibition assay conditions used for each CYP450 isoenzyme studied

| | CYP3A4 | CYP3A4 | CYP2C19 | CYP2C9 | CYP1A2 | CYP2D6 |
|---|---|---|---|---|---|---|
| Substrate (µM) | | | | | | |
| DBF | 1 | — | — | 0.5 | — | — |
| CEC | — | — | 35 | — | 4 | — |
| AMMC | — | — | — | — | — | 0.5 |
| BFC | — | 120 | — | — | — | — |
| Phosphate buffer pH 7.4 (mM) | 200 | 90 | 25 | 25 | 25 | 25 |
| Enzyme (pmol/well) | 1 | 1.5 | 6 | 2 | 1.5 | 3 |
| Incubation time (min) | 50 | 50 | 50 | 50 | 50 | 50 |
| Positive control | ketoconazole | ketoconazole | fluvoxamine | sulfaphenazole | fluvoxamine | quinidine |
| Excitation wavelength (nm) | 485 | 400 | 400 | 485 | 400 | 380 |
| Emission wavelength (nm) | 530 | 530 | 460 | 530 | 460 | 460 |

AMMC: aminoethyl-7-methoxy-4-methylcoumarin
BFC: 7-benzyloxy-4-trifluoromethylcoumarin
CEC: 3-cyano-7-ethoxycoumarin
DBF: dibenzylfluorescein

4.6. MDCKII-MDR1 Permeability

MDCKII-MDR1 cells are Madin-Darby canine kidney epithelial cells, overexpressing the human multi-drug resistance (MDR1) gene, coding for P-glycoprotein (P-gp). Cells are obtained from the Netherlands Cancer Institute and used after a 3-4 day culture in 24-well Millicell® cell culture insert plates (Millipore, PSRP010R5). A bi-directional MDCKII-MDR1 permeability assay is performed as described below.

$3 \times 10^5$ cells/mL ($1.2 \times 10^5$ cells/well) are seeded in plating medium consisting of DMEM (Sigma, D5796)+1% Glutamax-100 (Sigma, G8541)+1% antibiotic/antimycotic (Sigma, A5955)+10% FBS (Sigma, F7524; inactivated at 56° C. for 30 min). Cells are left in $CO_2$ incubator for 3-4 days. The medium is changed 24 h after seeding and on the day of experiment.

Test and reference compounds (amprenavir (Moravek Biochemicals, M-1613), diclofenac (Sigma, D6889)) are prepared in Dulbecco's phosphate buffer saline (D-PBS, pH 7.4; Sigma, D8662) and added to either the apical (400 µL) or basolateral (800 µL) chambers of the Millicell cell culture plates assembly at a final concentration of 10 µM (0.5 µM in case of amprenavir) with a final DMSO concentration of 1%. A receiver solution (D-PBS+1% DMSO) is added to the opposite chamber of the Millicell cell culture plate.

100 µM *Lucifer* yellow (Sigma, L0259) is added to all donor buffer solutions, in order to assess integrity of the cell monolayers by monitoring *Lucifer* yellow permeation. *Lucifer* yellow is a fluorescent marker for the paracellular transport pathway and is used as internal control to verify tight junction integrity of every cell monolayer during the assay.

After a 1 h incubation at 37° C. while shaking on an orbital shaker at 150 rpm, 75 µL aliquots are taken from both apical and basal chambers and added to 225 µL of MeCN: water solution (2:1) containing analytical internal standard (10 ng/mL warfarin) in a 96 well plate. Aliquoting is also performed at the beginning of the experiment from donor solutions to obtain initial concentrations.

Concentration of compound in the samples is measured by high performance liquid-chromatography/mass spectroscopy (LC-MS/MS).

Lucifer yellow is measured with a Thermo Scientific Fluoroskan Ascent FL (excitation wavelength: 485 nm, measurement wavelength: 530 nm) in a 96 well plate containing 150 µL of liquid from all receiver wells (basolateral or apical side).

Example 5. Whole Blood Assays

5.1. Ex Vivo Human TNFα Release Inhibition (Whole Blood Assay)

The objective of the assay is to evaluate the activity of compounds of the invention on the activated TLR/IRAK-4 pathway in an ex vivo human whole blood setting. Toll-like receptors (TLRs) are pattern recognition receptors that recognize a wide variety of microbial molecules, called pathogen-associated molecular patterns (PAMPs). Human TLR7 and TLR8 recognize imidazoquinoline compounds (e.g., CL097) and single stranded RNAs as their natural ligands. Activation of TLRs leads to the production of several cytokines (e.g., TNFα, IL-8, IL-6) by the TLR agonist-treated cells. Cytokine release is used as readout in this assay and represents a measure for the level of inhibition of the TLR/IRAK-4 pathway by the tested compound. It should be noted that in the context of the complete organism, other sources for these cytokines exist that are not dependent on the TLR/IRAK-4 pathway, such as e.g., macrophages (upon activation of the Fcγ receptor (Yan et al. 2012)) or T cells (upon activation of the T cell receptor (Brehm et al. 2005)).

5.1.1. Experimental Design

Blood is collected from healthy volunteers into lithium heparin tubes by venipuncture, then gently inverted several times to prevent clotting and incubated for at least 15 min at 37° C. on a rocking mixer shaker. Then, 200 µL of blood is dispensed into 2 mL-microtubes and pre-incubated in duplicate with DMSO 0.3% or test compound at different concentrations (from 10 to 0.01 µM, 3 fold dilutions in RPMI 1640 without glutamine (Life Technologies, 31870)) for 15 min at 37° C. After this pre-incubation, blood is triggered with CL097 (2 µg/mL from 1 mg/mL solution in water; InvivoGen, tlrl-c97) or vehicle (distilled water) for 3 h 30 min at 37° C. Microtubes are centrifuged at 5000×g for 10 min at 4° C. and approximately 80 µL of plasma is collected into a polystyrene 96-well plate. Plasma can be analyzed freshly or frozen at −80° C. shortly after triggering. Finally, the quantification of TNFα is performed by diluting 40 times the plasma using the human TNF-alpha DuoSet ELISA kit (R&D Systems, DY210), according to manufacturer's instructions. The optical density (OD) is determined at 450 nm on a PerkinElmer EnVision 2102 Multilabel plate reader.

5.1.2. Data Analysis

A standard curve is created by plotting the mean absorbance on the y-axis against the concentration on the x-axis and a best fit curve is drawn through the points on the graph. A linear regression analysis is performed to determine the equation (y=ax+b) and the R-squared value. For each blood sample replicate, the TNFα concentration is calculated, taking into account the dilution factor using the formula:

$$\text{TNF}\alpha \text{ concentration}_{sample1} = 40*(\text{OD}_{sample1}-b)/a$$

Data are then expressed as a percentage of inhibition (PIN) for each replicate using the formula:

$$PIN\ sample1 = \frac{\text{mean } TNF\alpha \text{ with } CL097 - TNF\alpha \text{ sample1}}{\text{mean } TNF\alpha \text{ with } CL097 - \text{mean } TNF\alpha \text{ with vehicle}} \times 100,$$

where 'mean TNFα with CL097' is the mean TNFα concentration of replicate samples triggered with CL097; 'TNFα sample1' is the TNFα concentration of sample 1; and 'mean TNFα with vehicle' is the mean TNFα concentration of replicate samples treated with vehicle.
Curve fittings are generated using mean PIN±SEM. Graphs and $IC_{50}$ calculations are derived using the GraphPad Prism® software.

5.2. Ex Vivo Rat TNFα Release Inhibition (Whole Blood Assay)

The objective of the assay is to assess the activity of compounds of the invention on the activated TLR/IRAK-4 pathway in an ex vivo rat whole blood setting. Toll-like receptors (TLRs) are pattern recognition receptors that recognize a wide variety of microbial molecules, called pathogen-associated molecular patterns (PAMPs). While human TLR7 and TLR8 both recognize imidazoquinoline compounds (e.g., CL097) and single stranded RNAs as their natural ligands, rodent TLR8 needs additional factors such as oligodeoxynucleotides (e.g., poly(dT)) for activation.

5.2.1. Experimental Design

Sprague Dawley rats (male, 7-8 weeks old, 200-250 g body weight) are obtained from Janvier Labs (France).

Blood, obtained by exsanguination, is collected from at least 2 rats into lithium heparinate tubes and then pre-incubated for at least 15 min at 37° C. on a rocking mixer shaker. Blood from all rats is mixed into a 50 mL polypropylene tube to get a unique blood batch. Then, 200 µL of blood is dispensed into 2 mL-microtubes and incubated in duplicate with DMSO 0.3% or test compound at different concentrations (from 10 to 0.01 µM, 3 fold dilutions in RPMI 1640 without glutamine (Life Technologies, 31870)) for 15 min at 37° C. After this pre-incubation, blood is triggered with CL097 (10 µg/mL from 1 mg/mL solution in water; InvivoGen, tlrl-c97) and poly(dT) (1 µM from 100 µM solution in water; InvivoGen, tlrl-pt17) or vehicle (distilled water) for 3 h 30 min at 37° C. Microtubes are centrifuged at 5000×g for 10 min at 4° C. and approximately 80 µL of plasma is collected into a polystyrene 96-well plate. Plasma can be analyzed freshly or frozen at −80° C. shortly after triggering. Finally, the quantification of TNFα is performed on plasma (1:3 diluted) using the rat TNF-alpha Quantikine ELISA kit (R&D Systems, SRTA00), according to manufacturer's instructions. The optical density (OD) is determined at 450 nm on a PerkinElmer EnVision 2102 Multilabel plate reader.

5.2.2. Data Analysis

A standard curve is created by plotting the mean absorbance on the y-axis against the concentration on the x-axis and a best fit curve is drawn through the points on the graph. A linear regression analysis is performed to determine the equation (y=ax+b) and the R-squared value. For each blood sample replicate, the TNFα concentration is calculated, taking into account the dilution factor using the formula:

$$\text{TNF}\alpha \text{ concentration}_{sample1} = 40*(\text{OD}_{sample1}-b)/a$$

Data are then expressed as a percentage of inhibition (PIN) for each replicate using the formula:

$$PIN\ sample1 = \frac{\text{mean } TNF\alpha \text{ with } CL097 - TNF\alpha \text{ sample1}}{\text{mean } TNF\alpha \text{ with } CL097 - \text{mean } TNF\alpha \text{ with vehicle}} \times 100,$$

where 'mean TNFα with CL097' is the mean TNFα concentration of replicate samples triggered with CL097+poly (dT); 'TNFα sample1' is the TNFα concentration of sample 1; and 'mean TNFα with vehicle' is the mean TNFα concentration of replicate samples treated with vehicle. Curve fittings are generated using mean PIN±SEM. Graphs and $IC_{50}$ calculations are derived using the GraphPad Prism® software.

Example 6. In Vivo Assays

6.1. Murine Model of Psoriatic-Like Epidermal Hyperplasia Induced by Topical Applications of Imiquimod, a TLR7/8 Agonist

6.1.1. Materials

Aldara® 5% imiquimod cream is obtained from MEDA. Anti-mouse IL-12/IL-23 p40 FG purified antibody (C17.8) is obtained from Affymetrix eBioscience (cat no. 16-7123-85).

6.1.2. Animals

Balb/cJ mice (female, 18-20 g body weight) are obtained from Janvier Labs (France). Mice are kept on a 12 h light/dark cycle (07:00-19:00). Temperature is maintained at 22±2° C., food and water are provided ad libitum.

6.1.3. Study Design

The design of the study is adapted from Van der Fits L. et al. (van der Fits et al. 2009).
On the first day, the mice are shaved around the two ears under light anaesthesia with isoflurane.
30 mg of commercially available imiquimod cream (Aldara 5% cream) are applied on both internal and external surfaces of each ear for 4 consecutive days, translating in a daily dose of 1.5 mg of the active compound. Control animals received the same quantity of vaseline.
From day 1 to day 5, mice are dosed with test compound, 10 or 30 mg/kg, p.o., b.i.d. in methyl cellulose 0.5%, before application of imiquimod (on day 5, the mice are dosed only once, 2 h before euthanasia).
In a positive reference group, the animals receive two intraperitoneal injections of anti-mouse IL-12/IL-23 p40 antibody, 10 mg/kg, on day 1 and 3 days before day 1.

6.1.4. Assessment of Disease

The thickness of both ears is measured daily with a thickness gage (Mitutoyo, Absolute Digimatic, 547-321). Body weight is assessed at initiation of the experiment and at sacrifice. At day 5, 2 h after the last dosing, the mice are sacrificed. The pinnae of the ear are cut, excluding cartilage. The pinnae are weighed and then immersed in a vial containing 1 mL of RNAlater® solution to assess gene expression or in formalin for histology.
There are 14 mice per group. The results are expressed as mean±SEM and statistical analysis is performed using one-way ANOVA followed by Dunnett's post-hoc test versus imiquimod-vehicle group.

6.1.5. Histology

After sacrifice, ears are collected and fixed in 3.7% formaldehyde before embedding in paraffin. 2 μm thick sections are cut and stained with haematoxylin and eosin. Ear epidermis thickness is measured by image analysis (SisNcom software) with 6 images per ear captured at 20× magnification. Data are expressed as mean±SEM and statistical analysis is performed using one-way ANOVA followed by Dunnett's post-hoc test versus imiquimod-vehicle group.

6.1.6. Gene Expression Analysis

Ears are removed from the RNAlater® solution and put in Trizol® after disruption with 1.4 mm ceramic beads in a Precellys device. Total RNA is then purified using NucleoSpin® RNA kit. cDNA is prepared and quantitative PCR is performed with gene-specific primers from Qiagen using SYBR Green technology in a ViiA7 real-time PCR system (Applied Biosystems). Expression levels of each gene (IL17A, IL1B, IL22, LCN2, S100A8 and S100A9) are calculated relative to the cyclophilin A housekeeping gene expression level. Data are expressed as mean±SEM of the relative quantity ($RQ=2^{-\Delta C_T}$, where $\Delta C_T = C_T$ sample $- C_T$ cyclophilin A). The statistical test used is ANOVA analysis of variance with Dunnett's post-hoc test versus imiquimod-vehicle group.

6.2. Murine Model of Psoriatic-Like Epidermal Hyperplasia Induced by Intradermal Injections of IL-23

6.2.1. Materials

Mouse recombinant IL-23, carrier free (14-8231, CF) is provided by e-Bioscience.

6.2.2. Animals

Balb/c mice (female, 18-20 g body weight) are obtained from CERJ (France). Mice are kept on a 12 h light/dark cycle (07:00-19:00). Temperature is maintained at 22° C., food and water are provided ad libitum.

6.2.3. Study Design

The design of the study is adapted from Rizzo H L. et al. (Rizzo et al. 2011).
On the first day (D1), the mice are shaved around the two ears.
For 4 consecutive days (D1 to D4), the mice receive a daily intradermal dose of mouse recombinant IL-23 (1 μg/20 μL in PBS/0.1% BSA) in the right pinna ear and 20 μL of PBS/0.1% BSA in the left pinna ear under anesthesia induced by inhalation of isoflurane.
From D1 to D5, mice are dosed with test-compound (10, 30, or 100 mg/kg, p.o., q.d in methylcellulose 0.5%) or with vehicle, 1 h prior IL-23 injection.

6.2.4. Assessment of Disease

The thickness of both ears is measured daily with an automatic caliper. Body weight is assessed at initiation and at sacrifice. On fifth day, 2 h after the last dosing, the mice are sacrificed. The pinnae of the ear are cut, excluding cartilage. The pinnae are weighed and then, placed in a vial containing 1 mL of RNAlater® solution or in formaldehyde.
At D4, blood samples are also collected from the retro-orbital sinus for PK profiling just before dosing (T0) and 1 h, 3 h, 6 h post-dosing.
There are 8 mice per group. The results are expressed as mean±SEM and statistical analysis is performed using one-way ANOVA followed by Dunnett's post-hoc test versus IL-23 vehicle groups.

6.2.5. Histology

After sacrifice, ears are collected and fixed in 3.7% formaldehyde before embedding in paraffin. 2 μm thick sections are done and stained with hematoxylin and eosin. Ear epidermis thickness is measured by image analysis (Sis'Ncom software) with 6 images per ear captured at magnification ×20. Data are expressed as mean±SEM and statistical analysis is performed using one-way ANOVA followed by Dunnett's post-hoc test versus IL-23 vehicle groups.

6.2.6. Gene Expression Analysis

Half ears are removed from RNAlater® solution and put in Trizol® after disruption with 1.4 mm ceramic beads in a Precellys device. Total RNA is then purified using Nucleo-Spin® RNA kit. cDNA is prepared and quantitative PCR is performed with gene-specific primers from Qiagen using SYBR Green technology in a ViiA7 real-time PCR system (Applied Biosystems). Expression levels of each gene (IL17A, IL1B, IL22, LCN2, S100A8 and S100A9) are calculated relative to the cyclophilin A housekeeping gene expression level. Data are expressed as mean±SEM of the relative quantity ($RQ=2^{-\Delta C_T}$, where $\Delta C_T = C_T$ sample $- C_T$ cyclophilin A). The statistical test used is ANOVA analysis of variance with Dunnett's post-hoc test versus the IL-23 vehicle group.

6.3. PK/PD Model: TNFα Release Induced by CL097, a Specific TLR7/8 Agonist

The aim of this assay is to determine the relationship between the inhibition of an IRAK-4 dependent event in vivo upon administration of a compound of the invention and the circulating concentration levels of this compound.

6.3.1. Materials

CL097 (cat no. tlrl-c97) and poly(dT) (cat no. tlrl-pt17) are obtained from InvivoGen.

AlphaLISA® mouse TNFα kits are obtained from Perkin-Elmer (cat no. AL505C).

6.3.2. Animals

DBA/1J mice (male, 18-20 g body weight) are obtained from Janvier Labs (France). Mice are kept on a 12 h light/dark cycle (07:00-19:00). Temperature is maintained at 22±2° C., food and water are provided ad libitum.

6.3.3. Study Design

The mice receive an oral dose of test-compound. A group of intact animals which does not receive any dosing is used as the t=0 time point.

Two blood samples obtained by intra-cardiac sampling (under isoflurane anesthesia) are collected into lithium heparinate tubes at 30 min, 1 h, 3 h, 8 h or 24 h post-dosing. One is used for pharmacokinetics (PK) analysis and the second for pharmacodynamic (PD) marker quantification.

6.3.4. Quantification of Compound Levels in Plasma

Whole blood samples are centrifuged at 5000 rpm for 10 min and the resulting plasma samples are stored at −20° C. pending analysis. Plasma concentrations of each test compound are determined by an LC-MS/MS method.

6.3.5. Determination of Pharmacokinetic Parameters

Pharmacokinetic parameters are calculated using WinNonlin® (Pharsight®, United States).

6.3.6. Quantification of PD Marker

Each blood sample is stimulated with CL097 and poly (dT) for 2 h at 37° C. Then, plasma is collected and analyzed for TNFα by AlphaLISA according to the manufacturer's instructions.

There are 6 mice per group. The results are expressed as TNFα concentration (pg/mL), or as percentage of inhibition (PIN) relative to the t=0 time point. The data are presented as mean±SEM and statistical analysis is performed using one-way ANOVA followed by Dunnett's post-hoc test versus vehicle group of the corresponding time point.

6.4. Murine Prophylactic Model of Atopic Dermatitis Induced by Topical Application of MC903

6.4.1. Materials

Methylcellulose 0.5% is obtained from VWR (cat no. AX021233). MC903 (calcipotriol) is obtained from Tocris Bioscience (cat no. 2700/50). ProSense® 680 is obtained from PerkinElmer (cat no. NEV10003). RNAlater® is obtained from Ambion (cat no. AM7021). Imalgene® 1000 (Merial) and Rompun 2% (Bayer) are obtained from Centravet (cat no. IMA004-6827812 and ROM001-6835444).

6.4.2. Animals

BALB/cN mice (female, 18-20 g body weight) or CD1/ Swiss mice (female, 24-26 g body weight) are obtained from Janvier Labs (France). Mice are kept on a 12 h light/dark cycle (07:00-19:00). Temperature is maintained at 22±2° C., food and water are provided ad libitum.

6.4.3. Study Design

The design of the study is adapted from Li M. et al. (Li et al. 2006).

On the first day (D1), the mice are anesthetized with an intraperitoneal injection of Imalgene and Rompun (7.5%/ 2.5%; 0.1 mL/10 g) and shaved around the two ears.

As of D1, either 20 μL EtOH or 2 nmol of MC903 (in 20 μL EtOH) are topically applied on both ears of mice for five consecutive days.

From D1 to D8, the mice are dosed with test compound (15 or 30 mg/kg, p.o., b.i.d in methylcellulose 0.5%) or dexamethasone (5 mg/kg, p.o., q.d in methylcellulose 0.5%), or with vehicle.

6.4.4. Quantification of Compound Levels in Plasma

Plasma concentrations of each test compound are determined by an LC-MS/MS method in which the mass spectrometer is operated in positive or negative electrospray mode.

6.4.5. Determination of Pharmacokinetic Parameters

Pharmacokinetic parameters are calculated using Phoenix® WinNonlin® (Pharsight®, United States).

6.4.6. Assessment of Disease

The thickness of both ears is measured (after anaesthesia induced by isoflurane inhalation) at initiation of the study, every other day and at sacrifice using a thickness gage (Mitutoyo, Absolute Digimatic, 547-321).

Body weight is assessed at initiation of the study, every other day and at sacrifice.

On D4, mice from all groups receive ProSense® 680 probe (0.8 nmol/10 g, IP). On D5, the mice are anesthetized with an intraperitoneal injection of Imalgene and Rompun (7.5%/2.5%; 0.1 mL/10 g). Granulocyte infiltration is measured using in vivo molecular imaging (Bruker In-Vivo Xtreme imaging system, excitation wavelength: 630 nm, emission wavelength: 700 nm, acquisition time: 5 seconds).

On D8, 2 h after the last dosing, mice are sacrificed and total blood is collected on EDTA-coated tubes and plasma is frozen for further measurements (including circulating compound). A sample of blood is also collected in heparin-coated tubes.

The pinnae of the ears are collected and weighed. One ear is cut longitudinally into 2 halves. One half is fixed in formaldehyde buffer 4% for histology; the other one is immersed in RNAlater® to assess gene expression.

There are 8 mice per group. The results are expressed as mean±SEM and statistical analysis is performed using one-way ANOVA followed by Dunnett's post-hoc test versus MC903 vehicle groups for ear thickness and weight, versus EtOH vehicle group for body weight.

6.4.7. Histology

After sacrifice, half ears are collected and fixed in 3.7% formaldehyde before embedding in paraffin. 4 µm thick sections are immunostained by immunohistochemistry with specific cell marker antibody: CD3 for T cells and EPX for eosinophils. The immunostained cell areas from a whole section per mouse are measured by image analysis (CaloPix software, TRIBVN Healthcare). Data are expressed as mean±SEM and statistical analysis is performed using one-way ANOVA followed by Dunnett's post-hoc test versus MC903 vehicle groups.

6.4.8. Gene Expression Analysis

Ears are removed from RNAlater® solution and placed in Trizol® after disruption with 1.4 mm ceramic beads in a Bertin Instruments Precellys® homogenizer. Total RNA is then extracted using a phenol/chloroform protocol and purified with a QIAcube using an RNeasy® 96 QIAcube® HT Kit (Qiagen, cat no. 74171). cDNA is prepared and quantitative PCR performed with gene-specific primers from Qiagen using SYBR Green technology in a ViiA 7 real-time PCR system (Applied Biosystems). Expression levels of each gene (IL4, IL5, IL13, TSLP, IL33, ST2, IL25, IL31, IFNγ, IL6, IL10, LCN2, S100A8 and S100A9) are calculated relative to the HPRT, GAPDH and β-actin housekeeping gene expression levels. Data are expressed as mean±SEM of the relative quantity ($RQ=2^{-\Delta C_T}$, where $\Delta C_T=C_T$ sample−average ($C_T$ HPRT, $C_T$ GAPDH, $C_T$ β-actin). The statistical test used is ANOVA analysis of variance with Dunnett's post-hoc test versus the EtOH/MC903 vehicle group.

6.5. Murine Therapeutic Model of Atopic Dermatitis Induced by Topical Application of MC903

6.5.1. Materials

Methylcellulose 0.5% is obtained from VWR (cat no. AX021233). MC903 (calcipotriol) is obtained from Tocris Bioscience (cat no. 2700/50). ProSense® 680 is obtained from PerkinElmer (cat no. NEV10003). RNAlater® is obtained from Ambion (cat no. AM7021). Imalgene® 1000 (Merial) and Rompun 2% (Bayer) are obtained from Centravet (cat no. IMA004-6827812 and ROM001-6835444).

6.5.2. Animals

BALB/cN mice (female, 18-20 g body weight) or CD1/Swiss mice (female, 24-26 g body weight) are obtained from Janvier Labs (France). Mice are kept on a 12 h light/dark cycle (07:00-19:00). Temperature is maintained at 22±2° C., food and water are provided ad libitum.

6.5.3. Study Design

The design of the study is adapted from Li M. et al. (Li et al. 2006).

On the first day (D1), the mice are anesthetized with an intraperitoneal injection of Imalgene and Rompun (7.5%/2.5%; 0.1 mL/10 g) and shaved around the two ears.

As of D1, either 20 µL EtOH or 2 nmol of MC903 (in 20 µL EtOH) are topically applied on both ears of mice up to D9, D11 or D15 (except during the weekend).

From D5, the mice are dosed with test compound (15 or 30 mg/kg, p.o., b.i.d in methylcellulose 0.5%) or dexamethasone (5 mg/kg, p.o., q.d in methylcellulose 0.5%), or with vehicle, until D10, D12, or D16.

6.5.4. Quantification of Compound Levels in Plasma

Plasma concentrations of each test compound are determined by an LC-MS/MS method in which the mass spectrometer is operated in positive or negative electrospray mode.

6.5.5. Determination of Pharmacokinetic Parameters

Pharmacokinetic parameters are calculated using Phoenix® WinNonlin® (Pharsight®, United States).

6.5.6. Assessment of Disease

The thickness of both ears is measured (after anaesthesia induced by isoflurane inhalation), prior to application of MC903, at initiation of the study, three times a week and at sacrifice using a thickness gage (Mitutoyo, Absolute Digimatic, 547-321).

Body weight is assessed at initiation of the study, three times a week and at sacrifice.

On D8, D10 or D11, mice from all groups receive ProSense® 680 probe (0.8 nmol/10 g, IP). On the next day (D9, D11 or D12), the mice are anesthetized with an intraperitoneal injection of Imalgene and Rompun (7.5%/ 2.5%; 0.1 mL/10 g). Granulocyte infiltration is then measured using in vivo molecular imaging (Bruker In-Vivo Xtreme imaging system, excitation wavelength: 630 nm, emission wavelength: 700 nm, acquisition time: 5 seconds).

On D10, D12, or D16, 2 h after the last dosing, the mice are sacrificed; total blood is collected on EDTA-coated tubes and plasma is frozen for further measurements (including circulating compound).

The pinnae of the ears are collected. One ear is cut longitudinally into 2 halves. One half is fixed in formaldehyde buffer 4% for histology; the other one is immersed in RNAlater® to assess gene expression.

There are 8 mice per group. The results are expressed as mean±SEM and statistical analysis is performed using one-way ANOVA followed by Dunnett's post-hoc test versus MC903 vehicle groups for ear thickness and weight, versus EtOH vehicle group for body weight.

6.5.7. Histology

After sacrifice, half ears are collected and fixed in 3.7% formaldehyde before embedding in paraffin. 4 µm thick sections are immunostained by immunohistochemistry with anti-CD3 antibody. The immunostained cell areas from a whole section per mouse are measured by image analysis (CaloPix software, TRIBVN Healthcare). Data are expressed as mean±SEM and statistical analysis is performed using one-way ANOVA followed by Dunnett's post-hoc test versus MC903 vehicle groups.

6.5.8. Gene Expression Analysis

Ears are removed from RNAlater® solution and placed in Trizol® after disruption with 1.4 mm ceramic beads in a Bertin Instruments Precellys® homogenizer. Total RNA is then extracted using a phenol/chloroform protocol and purified with a QIAcube using an RNeasy® 96 QIAcube® HT Kit (Qiagen, cat no. 74171). cDNA is prepared and quantitative PCR performed with gene-specific primers from Qiagen using SYBR Green technology in a ViiA 7 real-time PCR system (Applied Biosystems). Expression levels of each gene of interest (GOI=IL4, IL5, IL13, TSLP, IL33, ST2, IL25, IL31, IFNγ, IL6, IL10, LCN2, S100A8 and S100A9) are calculated relative to the HPRT, GAPDH and β-actin housekeeping gene expression levels.

All qPCR data are expressed as mean±SEM of the normalized relative quantity (NRQ=$2^{\wedge}(\Delta Cq\ GOI)$/Geomean ($2^{\wedge}(\Delta Cq\ HPRT)$, $2^{\wedge}(\Delta Cq\ GAPDH)$, $2^{\wedge}(\Delta Cq\ \beta\text{-actin})$)) where $\Delta Cq=Cq$ average–Cq sample. The statistical test used is ANOVA analysis of variance with Dunnett's post-hoc test versus the EtOH/MC903 vehicle group.

6.6 Murine Model of Systemic Lupus Erythematosus Induced by Epicutaneous Applications of Imiquimod

6.6.1. Materials

Aldara® 5% imiquimod cream is obtained from MEDA.
Mouse anti-double-stranded DNA antibodies ELISA kits are obtained from Alpha Diagnostic International (cat no. 5120). Mouse urinary albumin ELISA kits are obtained from Abcam (cat no. ab108792). Urine creatinine assay kits are obtained from Abnova (cat no. KA4344).

6.62. Animals

BALB/cJ mice (female, 18-20 g body weight) are obtained from Janvier Labs (France). Mice are kept on a 12 h light/dark cycle (07:00-19:00). Temperature is maintained at 22±2° C., food and water are provided ad libitum.

6.63. Study Design

The design of the study is adapted from Yokogawa M. et al. (Yokogawa et al. 2014).

On the first day (D1), the mice are shaved around the right ears.

The mice receive an epicutaneous application of 1.25 mg of imiquimod 3 times per week on the right pinna ear for 12 consecutive weeks (D1 to D86). The control group receives the same quantity of vaseline.

From D1 to D86, mice are dosed with test compound (30 mg/kg, p.o., q.d. in methylcellulose 0.5%) or with vehicle (10 mL/kg).

6.64. Assessment of Disease

The thickness of the ears is measured once a week with an automatic gage (Mitutoyo, Absolute Digimatic, 547-321).

Body weight is assessed at initiation and once a week until sacrifice. At necropsy, the spleen weight is also measured. The mice are sacrificed 2 h after the last dosing.

At different time points (e.g., on days D28, D56 and D84), the mice are individually placed in a metabolic cage to perform urinalysis and assess proteinuria (albumin to creatinine ratio).

Serums are collected at different time points (e.g., on D28, D56 and D86) to assess anti-double stranded-DNA IgG levels.

At D13, blood samples are also collected from the retro-orbital sinus for PK profiling just before dosing (T0) and 1 h, 3 h, 6 h post-dosing.

There are 8-19 mice per group. The results are expressed as mean±SEM and statistical analysis is performed using one-way ANOVA followed by Dunnett's post-hoc test versus imiquimod vehicle groups.

6.65. Quantification of Compound Levels in Plasma

Plasma concentrations of each test compound are determined by an LC-MS/MS method in which the mass spectrometer is operated in positive or negative electrospray mode.

6.6.6 Determination of Pharmacokinetic Parameters

Pharmacokinetic parameters are calculated using Phoenix® WinNonlin® (Pharsight®, United States).

6.7. Histology

After sacrifice, left kidneys are collected and cut longitudinally into 2 parts. One part is fixed in 3.7% formaldehyde before embedding in paraffin. 4 µm thick sections are made and stained with Period acid-Schiff (PAS) or immunostained with CD3 (T cells), CD20 (B cells) and F4/80 (macrophages).

6.67.1. Histopathology

In each glomerulus, 4 different readouts including mesangioproliferation, endocapillary proliferation, mesangial matrix expansion and segmental sclerosis are graded on a scale of 0 to 2 and then summed. For each kidney, about 50 glomeruli are scored and then averaged giving one glomerular lesion score (Yokogawa et al. 2014). Data are expressed as mean±SEM and statistical analysis is performed using the Kruskal-Wallis test followed by Dunn's post-hoc test versus imiquimod vehicle group.

6.6.7.2. Cellular Quantifications

For each cell type, immunohistochemical analysis is performed using image analysis (CaloPix software, TRIBVN Healthcare) on the whole tissue section at a magnification of ×20. Data are expressed as mean±SEM and statistical analysis is performed using one-way ANOVA followed by Dunnett's post-hoc test versus imiquimod vehicle group.

6.6.8. Gene Expression Analysis

At sacrifice, the second part of the left kidneys is placed in tubes containing 1.4 mm ceramic beads and disrupted in 1% DTT RLT lysis buffer (Qiagen, cat no. 79216) with a Bertin Instruments Precellys® homogenizer. Total RNA is then purified with a QIAcube using an RNeasy® 96 QIAcube® HT Kit (Qiagen, cat no. 74171). cDNA is prepared and quantitative PCR performed with gene-specific primers from Qiagen using SYBR Green technology in a ViiA 7 real-time PCR system (Applied Biosystems). Expression levels of each gene of interest (GOI=CD3, CD68, CD20, OAS1, Mx1, IFIT1, CXCL11 and Usp18) are calculated relative to the cyclophilin, GAPDH and β-actin housekeeping gene expression levels.

At sacrifice, one-third of the spleen is placed into tubes containing 1.4 mm ceramic beads and disrupted in Trizol® with a Bertin Instruments Precellys® homogenizer. Total RNA is extracted using a phenol/chloroform process and then purified with a QIAcube using an RNeasy® 96 QIAcube® HT Kit (Qiagen, cat no. 74171). cDNA is prepared and quantitative PCR performed with gene-specific primers from Qiagen using SYBR Green technology in a ViiA 7 real-time PCR system (Applied Biosystems). Expression levels of each gene of interest (GOI=CD20, IRF7, OAS1, Mx1, IFIT1, CXCL11, Usp18, BCL6, CXCL13, CXCR5, MAF, ICOSL, PDCD1, SH2D1a) are calculated relative to the cyclophilin, GAPDH and β-actin housekeeping gene expression levels.

All qPCR data are expressed as mean±SEM of the normalized relative quantity (NRQ=$2^{(\Delta Cq\ GOI)}$/Geomean ($2^{(\Delta Cq\ cyclophilin)}$, $2^{(\Delta Cq\ GAPDH)}$, $2^{(\Delta Cq\ \beta\text{-actin})}$)) where $\Delta Cq$=Cq average−Cq sample. The statistical test used is ANOVA analysis of variance with Dunnett's post-hoc test versus imiquimod vehicle group.

6.7. Murine Model of Psoriatic Arthritis Induced by Overexpression of IL-23

6.7.1. Materials

Mouse IL-23 enhanced episomal expression vector (EEV) is obtained from System Biosciences (cat no. EEV651A-1). Ringers solution tablets are obtained from Sigma-Aldrich (cat no. 96724-100TAB). Mouse IL-23 Quantikine ELISA Kits are obtained from R&D Systems (cat no. M2300). ProSense® 680 and OsteoSense® 750EX are obtained from PerkinElmer (cat no. NEV10003 and NEV10053EX). RNAlater® is obtained from Ambion (cat no. AM7021). Imalgene® 1000 (Merial) and Rompun® 2% (Bayer) are obtained from Centravet (cat no. IMA004-6827812 and ROM001-6835444).

6.7.2. Animals

B10.RIII mice (male, 8-week old) are obtained from Charles River (France). Mice are kept on a 12 h light/dark cycle (07:00-19:00). Temperature is maintained at 22±2° C., food and water are provided ad libitum.

6.7.3. Study Design

The design of the study is adapted from Sherlock J P. et al. (Sherlock et al. 2012).

On the first day (D1), the mice undergo a hydrodynamic injection of Ringer or IL-23 EEV in Ringer into the tail vein (3 µg/2.1 mL, IV injected over a period of 4-6 sec).

As of D5, twice a week, the mice are scored for clinical symptoms until the end of the experiment.

On D5, blood is collected by puncture in the submandibular vein to assess the serum IL-23 concentration.

On D9, mice from all groups receive ProSense® 680 probe (0.8 nmol/10 g, IP). On D10, the mice are anesthetized with an intraperitoneal injection of Imalgene and Rompun (7.5%/2.5%; 0.1 mL/10 g). Granulocyte infiltration is then measured using in vivo molecular imaging (Bruker In-Vivo Xtreme imaging system, excitation wavelength: 630 nm, emission wavelength: 700 nm, acquisition time: 5 seconds).

On D11, randomization is performed according to ProSense® 680 molecular imaging and scoring.

As of D12, mice are dosed with test compound (30 mg/kg, p.o., b.i.d in methylcellulose 0.5%) or with vehicle.

On D19, blood is sampled at time T0, T1h, T3h and T6h after last dosing. Plasma is separated and kept at 20° C. until bioanalysis.

On D36, mice from all groups are sacrificed 2 h after last administration of compound. The following is collected:

Heels around enthesis (without skin) of the left hindlimb are immediately snap frozen in Precellys tubes. Fingers are collected in tubes containing RNAlater®. The right hindlimb is immediately fixed in formaldehyde buffer 4% for histology evaluation. X-ray measurement is performed 48 h after fixation.

One ear is collected in tube containing RNAlater® for transcript analysis.

Total blood is collected in a serum blood tube and mixed by gentle inversion 8-10 times. After clotting, blood samples are centrifuged 10 min at 1800×g. After centrifugation, serum is stored at −80° C.

Part of the colon (1 cm distal colon) is immediately snap frozen in Precellys tube for transcript analysis. Another part (1 cm distal colon) is immediately fixed in formaldehyde buffer 4% for further histology analysis.

6.7.4. Assessment of Disease

Body weight is assessed at initiation of the study, then twice a week and at sacrifice.

Twice weekly, clinical signs of inflammation are scored: 0 for normal paw; 1 if swelling of one digit; 2 if swelling of two or more digits; 3 if swelling of the entire paw. The scores of all limbs are summed up to produce a global score.

On D23, mice from all groups receive ProSense® 680 probe (0.8 nmol/10 g, IP). On D24, the mice are anesthetized with an intraperitoneal injection of Imalgene and Rompun (7.5%/2.5%; 0.1 mL/10 g). Granulocyte infiltration is then measured using in vivo molecular imaging (Bruker In-Vivo Xtreme imaging system, excitation wavelength: 630 nm, emission wavelength: 700 nm, acquisition time: 5 seconds).

On D32, mice from all groups receive ProSense® 680 probe (0.8 nmol/10 g, IP) and OsteoSense® 750EX probe (0.8 nmol/10 g, IP). On D33, the mice are anesthetized with an intraperitoneal injection of Imalgene and Rompun (7.5%/2.5%; 0.1 mL/10 g). Granulocyte infiltration and bone remodelling are measured using in vivo molecular imaging (Bruker In-Vivo Xtreme imaging system; excitation wavelength: 630 nm, emission wavelength: 700 nm, acquisition time: 5 seconds for ProSense® 680 probe; excitation wavelength: 720 nm, emission wavelength: 790 nm, acquisition time: 5 seconds for OsteoSense® 750EX probe).

There are 10 mice per group. The results are expressed as mean±SEM and statistical analysis is performed using one-way ANOVA followed by Dunnett's post-hoc test versus diseased vehicle group for scoring and imaging analysis, versus sham vehicle group for body weight.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by OpenEye Scientific Software, Inc. and the Autonom Software tool sold by MDL Information Systems, Inc. In the instance where the indicated chemical name and the depicted structure differ, the depicted structure will control.

REFERENCES

Bain J et al. 2003. The specificities of protein kinase inhibitors: an update. *Biochem. J.* 371, 199-204.

Brehm M A, Daniels K A, Welsh R M. 2005. Rapid Production of TNF-α following TCR Engagement of Naive CD8 T Cells. *J. Immunol.* 175, 5043-5049.

Broekman F, Giovannetti E, Peters G J. 2011. Tyrosine kinase inhibitors: Multi-targeted or single-targeted? *World J. Clin. Oncol.* 2, 80-93.

Bundgaard H. 1985. *Design of prodrugs*, Elsevier.

Carmi Y et al. 2013. The Role of IL-1f in the Early Tumor Cell-Induced Angiogenic Response. *J. Immunol.* 190, 3500-3509.

Chiang E Y, Yu X, Grogan J L. 2011. Immune Complex-Mediated Cell Activation from Systemic Lupus Erythematosus and Rheumatoid Arthritis Patients Elaborate Different Requirements for IRAK1/4 Kinase Activity across Human Cell Types. *J. Immunol.* 186, 1279-1288.

Cohen P. 2009. Targeting protein kinases for the development of anti-inflammatory drugs. *Curr. Opin. Cell Biol.* 21, 317-324.

Dinarello C A, Simon A, van der Meer J W M. 2012. Treating inflammation by blocking interleukin-1 in a broad spectrum of diseases. *Nat. Rev. Drug Discov.* 11, 633-652.

Dy G K, Adjei A A. 2013. Understanding, recognizing, and managing toxicities of targeted anticancer therapies. *C A. Cancer J. Clin.* 63, 249-279.

Fabian M A et al. 2005. A small molecule-kinase interaction map for clinical kinase inhibitors. *Nat. Biotechnol.* 23, 329-336.

van der Fits L et al. 2009. Imiquimod-Induced Psoriasis-Like Skin Inflammation in Mice Is Mediated via the IL-23/IL-17 Axis. *J. Immunol.* 182, 5836-5845.

Force T, Kolaja K L. 2011. Cardiotoxicity of kinase inhibitors: the prediction and translation of preclinical models to clinical outcomes. *Nat. Rev. Drug Discov.* 10, 111-126.

Koziczak-Holbro M et al. 2009. The critical role of kinase activity of interleukin-1 receptor-associated kinase 4 in animal models of joint inflammation. *Arthritis Rheum.* 60, 1661-1671.

Kroeger K M, Sullivan B M, Locksley R M. 2009. IL-18 and IL-33 elicit Th2 cytokines from basophils via a MyD88- and p38α-dependent pathway. *J. Leukoc. Biol.* 86, 769-778.

Li D et al. 2014. IL-33 promotes ST2-dependent lung fibrosis by the induction of alternatively activated macrophages and innate lymphoid cells in mice. *J. Allergy Clin. Immunol.* 134, 1422-1432.e11.

Li M et al. 2006. Topical vitamin D3 and low-calcemic analogs induce thymic stromal lymphopoietin in mouse keratinocytes and trigger an atopic dermatitis. *Proc. Natl. Acad. Sci.* 103, 11736-11741.

Li S et al. 2002. IRAK-4: A novel member of the IRAK family with the properties of an IRAK-kinase. *Proc. Natl. Acad. Sci. U.S.A* 99, 5567-5572.

Li Z et al. 2015. Inhibition of IRAK1/4 sensitizes T cell acute lymphoblastic leukemia to chemotherapies. *J. Clin. Invest.* 125, 1081-1097.

McHedlidze T et al. 2013. Interleukin-33-dependent innate lymphoid cells mediate hepatic fibrosis. *Immunity* 39, 357-371.

Nabe T. 2014. Interleukin (IL)-33: New Therapeutic Target for Atopic Diseases. *J. Pharmacol. Sci.* 126, 85-91.

Ngo V N et al. 2011. Oncogenically active MYD88 mutations in human lymphoma. *Nature* 470, 115-119.

Rankin A L et al. 2010. IL-33 Induces IL-13-Dependent Cutaneous Fibrosis. *J. Immunol.* 184, 1526-1535.

Rhyasen G W, Starczynowski D T. 2015. IRAK signalling in cancer. *Br. J. Cancer* 112, 232-237.

Ringwood L, Li L. 2008. The involvement of the interleukin-1 Receptor-Associated Kinases (IRAKs) in cellular signaling networks controlling inflammation. *Cytokine* 42, 1-7.

Rizzo H L et al. 2011. IL-23-Mediated Psoriasis-Like Epidermal Hyperplasia Is Dependent on IL-17A. *J. Immunol.* 186, 1495-1502.

Salimi M et al. 2013. A role for IL-25 and IL-33-driven type-2 innate lymphoid cells in atopic dermatitis. *J. Exp. Med.* 210, 2939-2950.

Sherlock J P et al. 2012. IL-23 induces spondyloarthropathy by acting on ROR-γt+CD3+CD4-CD8-entheseal resident T cells. *Nat. Med.* 18, 1069-1076.

Staschke K A et al. 2009. IRAK4 Kinase Activity Is Required for Th17 Differentiation and Th17-Mediated Disease. *J. Immunol.* 183, 568-577.

Sundberg T B et al. 2014. Small-molecule control of cytokine function: new opportunities for treating immune disorders. *Curr. Opin. Chem. Biol.* 23, 23-30.

Treon S P et al. 2012. MYD88 L265P Somatic Mutation in Waldenstrom's Macroglobulinemia. *N. Engl. J. Med.* 367, 826-833.

Vidal-Vanaclocha F et al. 2000. IL-18 regulates IL-1β-dependent hepatic melanoma metastasis via vascular cell adhesion molecule-1. *Proc. Natl. Acad. Sci.* 97, 734-739.

Wang Z et al. 2009. IRAK-4 Inhibitors for Inflammation. *Curr. Top. Med. Chem.* 9, 724-737.

Wuts P G M, Greene T W. 2006. *Greene's Protective Groups in Organic Synthesis* 4th ed., Wiley-Interscience.

Yan C et al. 2012. C5a-regulated CCAAT/Enhancer-binding Proteins β and δ Are Essential in Fcγ Receptor-mediated Inflammatory Cytokine and Chemokine Production in Macrophages. *J. Biol. Chem.* 287, 3217-3230.

Yokogawa M et al. 2014. Epicutaneous Application of Toll-like Receptor 7 Agonists Leads to Systemic Auto-immunity in Wild-Type Mice: A New Model of Systemic Lupus Erythematosus. *Arthritis Rheumatol.* 66, 694-706.

---

The invention claimed is:
1. A compound according to Formula I:

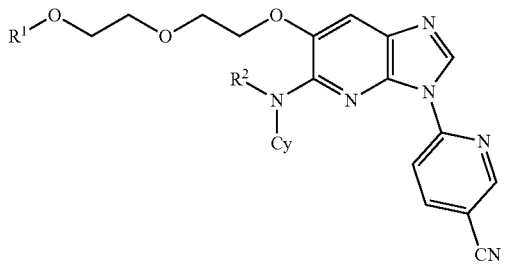

wherein
Cy is
  monocyclic $C_{3-7}$ cycloalkyl optionally substituted with one or more independently selected $R^3$, or
  4-7 membered monocyclic heterocycloalkyl comprising one or two heteroatoms independently selected from N, S, or O, optionally substituted with one or more independently selected $R^3$;
$R^1$ is
  H,
  —$SO_3H$,
  —$P(=O)(OH)_2$,
  $C_{1-4}$ alkyl,
  —C(=O)-(4-7 membered monocyclic heterocycloalkyl comprising one or two heteroatoms independently selected from N, S, or O), or
  —C(=O)$C_{1-6}$ alkyl, which $C_{1-6}$ alkyl is optionally substituted with one or more independently selected $R^4$ groups;
$R^2$ is H or $C_{1-4}$ alkyl;
each $R^3$ is independently selected from:
  OH,
  =O,
  halo, or
  $C_{1-4}$ alkyl;
each $R^4$ is independently selected from:
  —$NR^{5a}R^{5b}$,
  —C(=O)OH,
  4-7 membered monocyclic heterocycloalkyl comprising one or two heteroatoms independently selected from N, S, or O, optionally substituted with one or more independently selected $C_{1-4}$ alkyl, or
  —NHC(=O)—$C_{1-4}$ alkyl-$NH_2$; and
$R^{5a}$ and $R^{5b}$ are independently H or $C_{1-4}$ alkyl;
or a pharmaceutically acceptable salt or a solvate or the salt of a solvate thereof.

2. A compound or pharmaceutically acceptable salt thereof according to claim 1, wherein Cy is monocyclic $C_{3-7}$ cycloalkyl substituted with one or two independently selected $R^3$.

3. A compound or pharmaceutically acceptable salt thereof according to claim 1, wherein Cy is tetrahydropyranyl or tetrahydrothiopyranyl, each of which is optionally substituted with one or two independently selected $R^3$.

4. A compound or pharmaceutically acceptable salt thereof according to claim 1, wherein $R^3$ is selected from OH, =O, F, or —$CH_3$.

5. A compound or pharmaceutically acceptable salt thereof according to claim 1, wherein the compound is according to Formula IIa, IIb, IIc, IId, IIe or IIf:

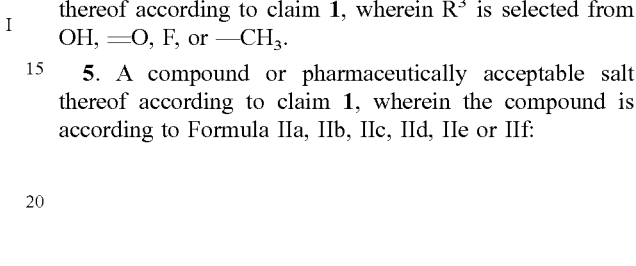

IIa

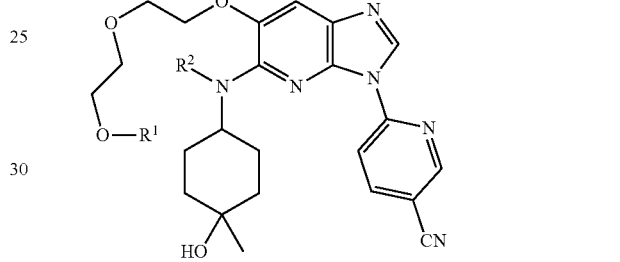

IIb

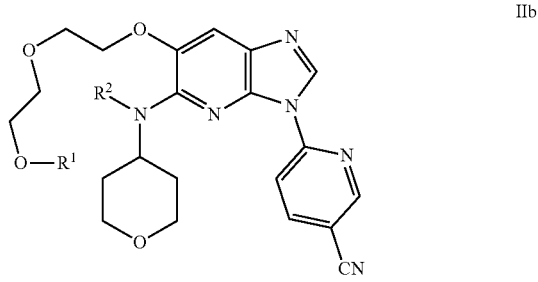

IIc

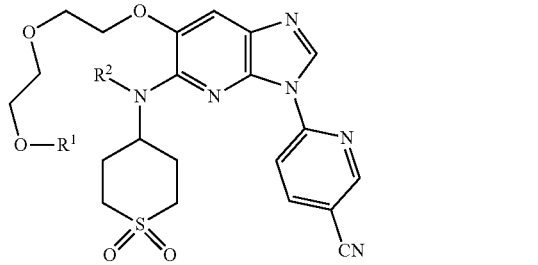

IId

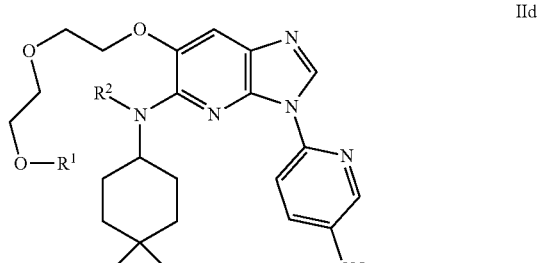

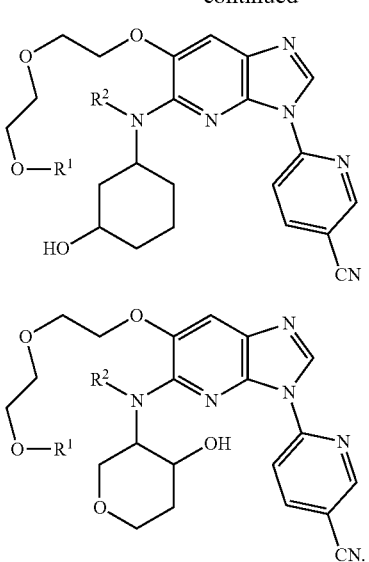

6. A compound or pharmaceutically acceptable salt thereof according to claim 1, wherein $R^4$ is H, —$CH_3$, —$SO_3H$, or —P(=O)(OH)$_2$.

7. A compound or pharmaceutically acceptable salt thereof according to claim 1, wherein $R^4$ is —C(=O)$C_{1-6}$ alkyl, which $C_{1-6}$ alkyl is substituted with one or two independently selected $R^4$.

8. A compound or pharmaceutically acceptable salt thereof according to claim 1, wherein $R^4$ is —C(=O)$C_{1-6}$ alkyl, which $C_{1-6}$ alkyl is substituted with one or two independently selected —C(=O)OH, —$NH_2$, —$NHCH_3$, or —$N(CH_3)_2$.

9. A compound or pharmaceutically acceptable salt thereof according to claim 1, wherein $R^2$ is H or —$CH_3$.

10. A compound or pharmaceutically acceptable salt thereof according to claim 1, wherein the compound is
6-[6-[2-(2-hydroxy-ethoxy)-ethoxy]-5-(tetrahydro-pyran-4-ylamino)-imidazo[4,5-b]pyridin-3-yl]-nicotinonitrile, or
(S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]-ethoxy}-ethyl ester.

11. A pharmaceutical composition comprising a pharmaceutically acceptable carrier and a pharmaceutically effective amount of a compound or pharmaceutically acceptable salt thereof, according to claim 1.

12. A pharmaceutical composition according to claim 11 comprising a further therapeutic agent.

13. The pharmaceutical composition according to claim 12, wherein the further therapeutic agent is an agent for the treatment of rheumatoid arthritis.

14. A method for treatment of rheumatoid arthritis in a human comprising administering an effective amount of the compound of claim 1 to the human.

15. A method for treatment of rheumatoid arthritis in a human comprising administering an effective amount of 6-[6-[2-(2-hydroxy-ethoxy)-ethoxy]-5-(tetrahydro-pyran-4-ylamino)-imidazo[4,5-b]pyridin-3-yl]-nicotinonitrile or (S)-2-amino-3-methyl-butyric acid 2-{2-[3-(5-cyano-pyridin-2-yl)-5-(tetrahydro-pyran-4-ylamino)-3H-imidazo[4,5-b]pyridin-6-yloxy]ethoxy}-ethyl ester to the human.

* * * * *

SEQUENCE LISTING

```
<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<223> OTHER INFORMATION: RIP140 peptide

<400> SEQUENCE: 1

Cys Tyr Gly Val Ala Ser Ser His Leu Lys Thr Leu Leu Lys Lys Ser
1               5                   10                  15

Lys Val Lys Asp Gln
            20

<210> SEQ ID NO 2
<211> LENGTH: 21
<212> TYPE: PRT
<213> ORGANISM: Artificial Sequence
<220> FEATURE:
<223> OTHER INFORMATION: Histone H3 peptide

<400> SEQUENCE: 2

Ala Arg Thr Lys Gln Thr Ala Arg Lys Ser Thr Gly Gly Lys Ala Pro
1               5                   10                  15

Arg Lys Gln Leu Cys
            20

<210> SEQ ID NO 3
<211> LENGTH: 13
<212> TYPE: PRT
<213> ORGANISM: Artificial Sequence
<220> FEATURE:
<223> OTHER INFORMATION: Histone H1-derived peptide

<400> SEQUENCE: 3

Gly Gly Gly Pro Ala Thr Pro Lys Lys Ala Lys Lys Leu
1               5                   10

<210> SEQ ID NO 4
<211> LENGTH: 39
<212> TYPE: PRT
<213> ORGANISM: Artificial Sequence
<220> FEATURE:
<223> OTHER INFORMATION: PDKtide

<400> SEQUENCE: 4

Lys Thr Phe Cys Gly Thr Pro Glu Tyr Leu Ala Pro Glu Val Arg Arg
1               5                   10                  15
```

```
Glu Pro Arg Ile Leu Ser Glu Glu Glu Gln Glu Met Phe Arg Asp Phe
            20                  25                  30
Asp Tyr Ile Ala Asp Trp Cys
            35
```